(12) United States Patent
Kormann et al.

(10) Patent No.: US 11,332,726 B2
(45) Date of Patent: May 17, 2022

(54) PERMANENT GENE CORRECTION BY MEANS OF NUCLEOTIDE-MODIFIED MESSENGER RNA

(71) Applicants: Eberhard Karls Universität Tübingen Medizinische Fakultät, Tübingen (DE); Helmholtz-Zentrum für Infektionsforschung GmbH für das Helmholtz-Institut für Pharmazeutische Forschung Saarland (HIPS), Saarbrücken (DE)

(72) Inventors: Michael Kormann, Weil im Schönbuch (DE); Lauren Mays Weddle, Newport, KY (US); Claus-Michael Lehr, Saarbrücken-Dudweiler (DE); Brigitta Loretz, Saarbrücken (DE); Emad Malaeksefat, Heidelberg (DE)

(73) Assignees: EBERHARD KARLS UNIVERSITÄT TÜBINGEN MEDIZINISCHE FAKULTÄT, Tübingen (DE); HELMHOLTZ-ZENTRUM FÜR INFEKTIONSFORSCHUNG GMBH FÜR DAS HELMHOLTZ-INSTITUT FÜR PHARMAZEUTISCHE FORSCHUNG SAARLAND (HIPS), Saarbrücken (DE)

( * ) Notice: Subject to any disclaimer, the term of this patent is extended or adjusted under 35 U.S.C. 154(b) by 0 days.

(21) Appl. No.: 16/399,708

(22) Filed: Apr. 30, 2019

(65) Prior Publication Data
US 2019/0376051 A1 Dec. 12, 2019

Related U.S. Application Data

(63) Continuation of application No. 15/094,926, filed on Apr. 8, 2016, now abandoned, which is a continuation of application No. PCT/EP2014/071343, filed on Oct. 6, 2014.

(30) Foreign Application Priority Data

Oct. 8, 2013 (DE) .................... 10 2013 111 099.1

(51) Int. Cl.
| | |
|---|---|
| C12N 9/22 | (2006.01) |
| C12N 15/11 | (2006.01) |
| C12N 15/115 | (2010.01) |
| C07K 14/47 | (2006.01) |
| C07K 14/785 | (2006.01) |

(52) U.S. Cl.
CPC .............. *C12N 9/22* (2013.01); *C12N 15/111* (2013.01); *C12N 15/115* (2013.01); *C07K 14/4712* (2013.01); *C07K 14/785* (2013.01); *C12N 2310/16* (2013.01); *C12N 2310/335* (2013.01); *C12N 2310/3341* (2013.01); *C12N 2310/3519* (2013.01)

(58) Field of Classification Search
CPC ....... C12N 9/22; C12N 15/111; C12N 15/115; C12N 2310/20; C12N 2310/16
See application file for complete search history.

(56) References Cited

U.S. PATENT DOCUMENTS

| | | | |
|---|---|---|---|
| 2012/0195936 A1 | 8/2012 | Rudolph et al. | |
| 2013/0117870 A1 | 5/2013 | Fahrenkruq et al. | |
| 2013/0137104 A1 | 5/2013 | Cost et al. | |
| 2014/0141068 A1 | 5/2014 | Bancel et al. | |
| 2015/0056705 A1 | 2/2015 | Conway et al. | |
| 2015/0152436 A1* | 6/2015 | Musunuru ................ | C12N 9/22 424/93.21 |

FOREIGN PATENT DOCUMENTS

| | | |
|---|---|---|
| WO | 2007/024708 A2 | 3/2007 |
| WO | 2011/012316 A2 | 2/2011 |

OTHER PUBLICATIONS

Beerli et al., "Positive and negative regulation of endogenous genes by designed transcription factors," Proc Natl Acad Sci USA (2000) 97(4):1495-1500.
Carlson et al., "Targeting DNA with fingers and TALENs," Mol Therapy-nucleic Acid (2012) 1, e3.
Cong et al., "Multiplex genome engineering using CRISPR/Cas systems," Science (2013) 339(6121):819-823.
Doyon et al., "Heritable targeted gene disruption in zebrafish using designed zinc-finger nucleases," Nat Biotechnol (2008) 26(6):702-708.
Gaj et al., "ZFN, TALEN, and CRISPR/Cas-based methods for genome engineering," Trends in Biotechnology (2013) 31(7):397-405.
Examination report for DE 10 2013 111 099.1, dated Jul. 16, 2014, 12 pages (with English translation).
International Search Report and Written Opinion for PCT/EP2014/071343, dated Jan. 9, 2015, 14 pages.

(Continued)

*Primary Examiner* — Antonio Galisteo Gonzalez
(74) *Attorney, Agent, or Firm* — Rimon, P.C.

(57) ABSTRACT

The present invention relates to a nucleotide-modified messenger RNA for the permanent correction of a genetic alteration on a DNA. The invention further relates to a nucleotide-modified messenger RNA in combination with a repair template. It also relates to a pharmaceutical composition. It finally relates to methods for the correction of a genetic alteration on a DNA.

27 Claims, 29 Drawing Sheets
Specification includes a Sequence Listing.

(56) References Cited

OTHER PUBLICATIONS

International Search Report and Written Opinion for PCT/US2014/59497, dated Jan. 16, 2015, 13 pages.
Kariko et al., "Increased erythropoiesis in mice injected with submicrogram guantities of pseudouridine-containina mRNA encodina erythropoietin," Mol Ther (2012) 20(5):948-953.
Kariko et al., "Incorporation of Pseudouridine into mRNA yields superior nonimmunogenic vector with increased translational capacity and biological stability," Mol Therapy (2008) 16(11):1833-1840.
Kormann et al., "Expression of therapeutic proteins after delivery of chemically modified mRNA in mice," Nat Biotechnol (2011) 29(2):154-157.
Kormann, "Gene therapies for pulmonary disease are close to final development," Biopro (2014) pp. 1-6 Retrieved from the Internet: URL: http://www.bio-pro.de/magazin/index.html?lang=en&artikelid=/artikel/10062/index.html. Retrieved on Dec. 19, 2014.
Mali et al., "RNA-guided human genome engineering via Cas9," Science (2013) 339(6121):823-826.
McCaffrey et al., "The buzz on the cut: from dream to reality," (2013) pp. 1-15 Retrieved from the Internet: URL: http://zon.trilinkbiotech.com/2013/07/01 /the-buzz-on-the-cut-from-dream-to-reality. Retrieved on Dec. 18, 2014.
McLvor et al., "Therapeutic delivery of mRNA: The medium is the message," Molecular Therapy (2011) 19(5):822-823.
Meader et al., "Rapid "Open-source" engineering of customized zinc-finger nucleases for hiahly efficient aene modification," Molecular Cell (2008) 31 (2)294-301.
Nafee et al., "Chitosan-coated PLGA nanoparticles for DNA/RNA delivery: effect of the formulation parameters on complexation and transfection of antisense oligonucleotides," Nanomedicine: Nanotechnology, Biology and Medicine (2007) 3(3):173-183.
Sahin et al., "mRNA-based therapeutics-developing a new class of drugs," Nature Reviews Drua Discovery (2014) 13(10):759-780.
Schwank et al., "Functional repair of CFTR by CRISPR/Cas9 in Intestinal stem cell oraanoids of cystic fibrosis patients," Cell Stem Cell (2013) 13(6):653-658.
Tsai et al., "Dimeric CRISPR RNA-guided FokI nucleases for highly specific genome editing," Nature Biotechnoloay (2014) 32:569-576.
Urnov et al., "Genome editing with engineered zinc finger nucleases," Nature Reviews Genet (2010) 11 (9):636-646.
Urnov et al., "Highly efficient endogenous human gene correction using designed zinc-finder nucleases," Nature (2005) 435:646-651.
Yamamoto et al., "Current prospects for mRNA gene delivery," European Journal of Pharmaceutics and Biopharmaceutics (2009) 71 (3):484-489.
Requirement for Restriction for U.S. Appl. No. 15/094,926, dated Jul. 28, 2017, 8 pages.
Response to Requirement for Restriction for U.S. Appl. No. 15/094,926, dated Sep. 28, 2017, 6 pages.
Non-Final Office Action for U.S. Appl. No. 15/094,926, dated Dec. 21, 2017, 11 pages.
Response to Non-Final Office Action for U.S. Appl. No. 15/094,926, dated Jun. 21, 2018, 10 pages.
Final Rejection for U.S. Appl. No. 15/094,926, dated Nov. 1, 2018, 13 pages.
Notice of Abandonment for U.S. Appl. No. 15/094,926, dated May 16, 2019, 2 pages.

* cited by examiner

Fig. 4
A  Tag 1: Introduce TALENs and Donor
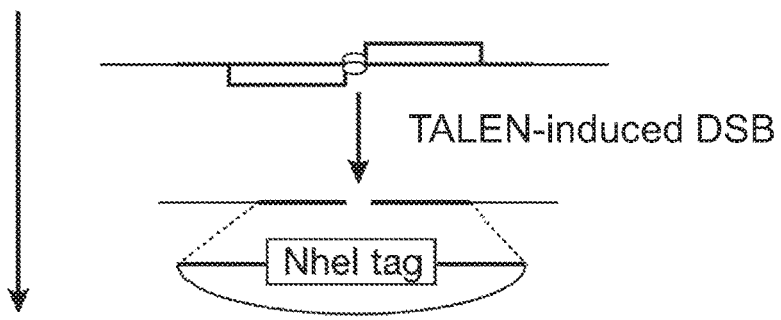
Tag 4: Harvest DNA, analyse tag frequency
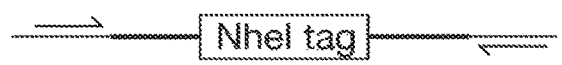
B
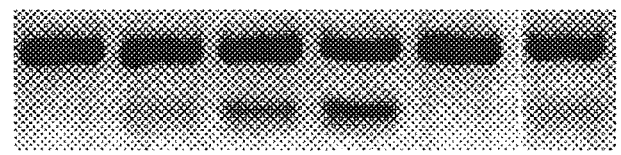

Fig. 6
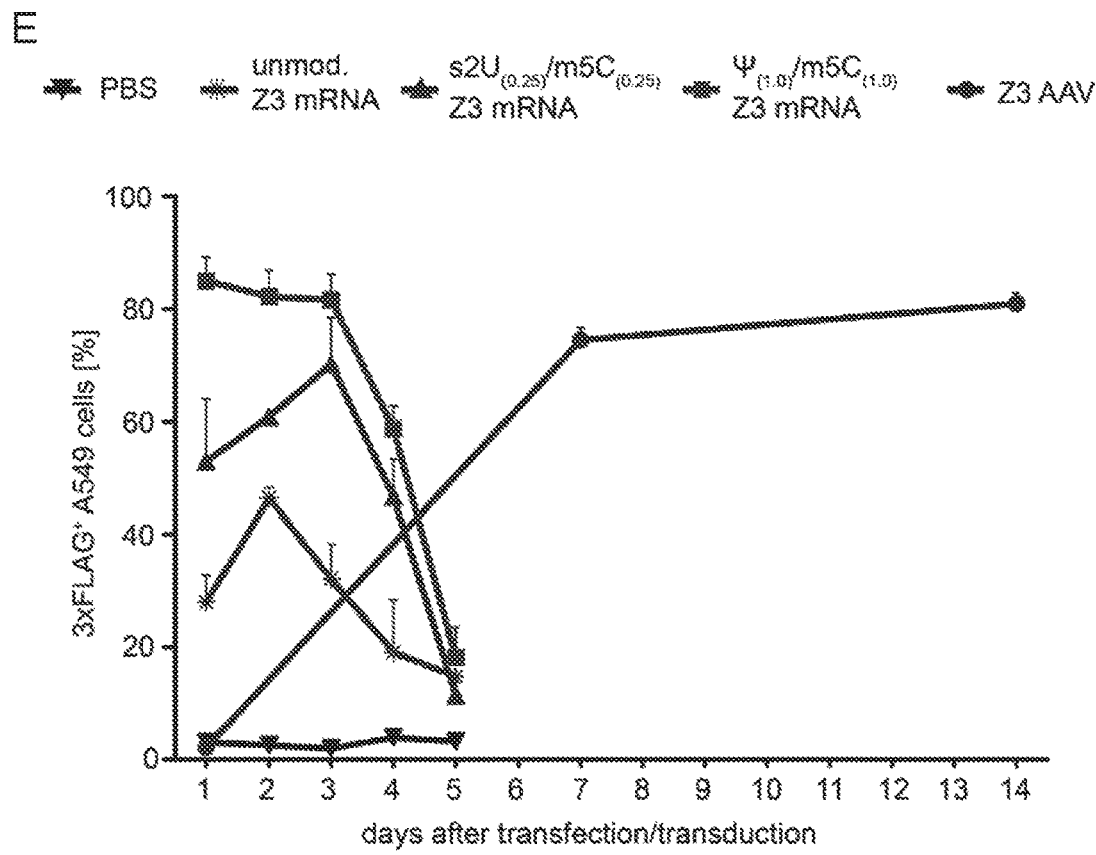
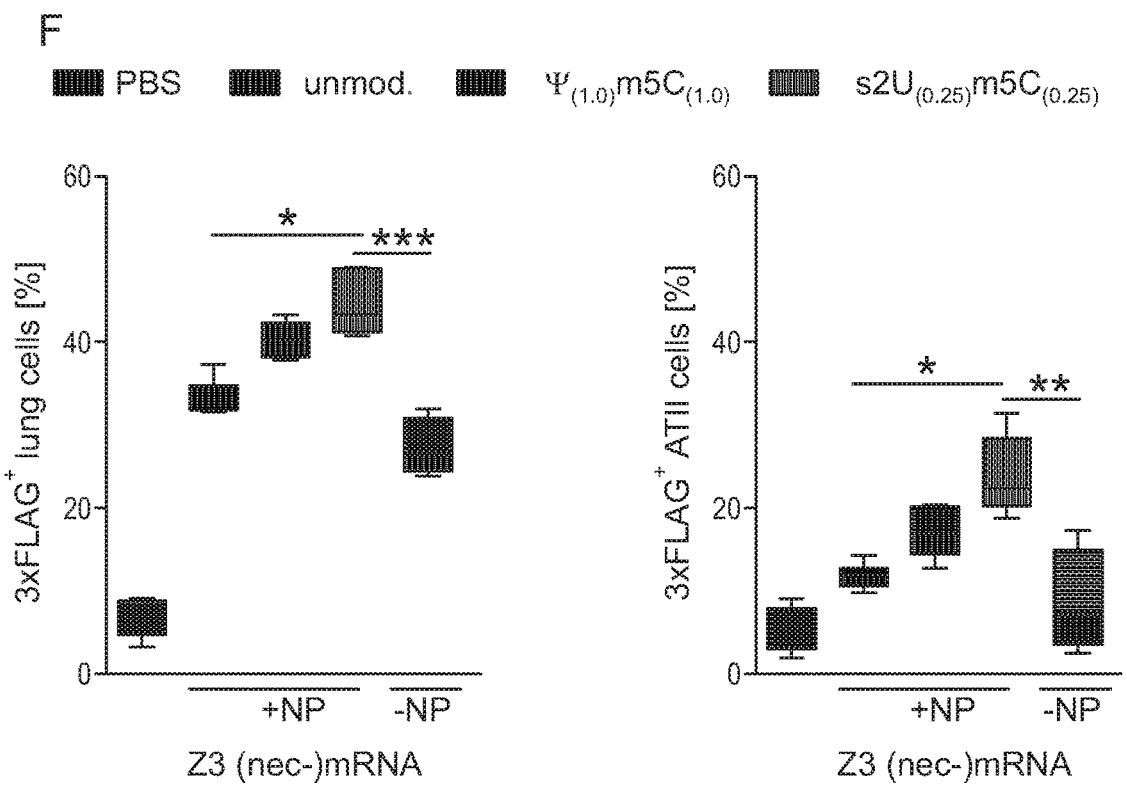

Fig. 9

Fig. 13
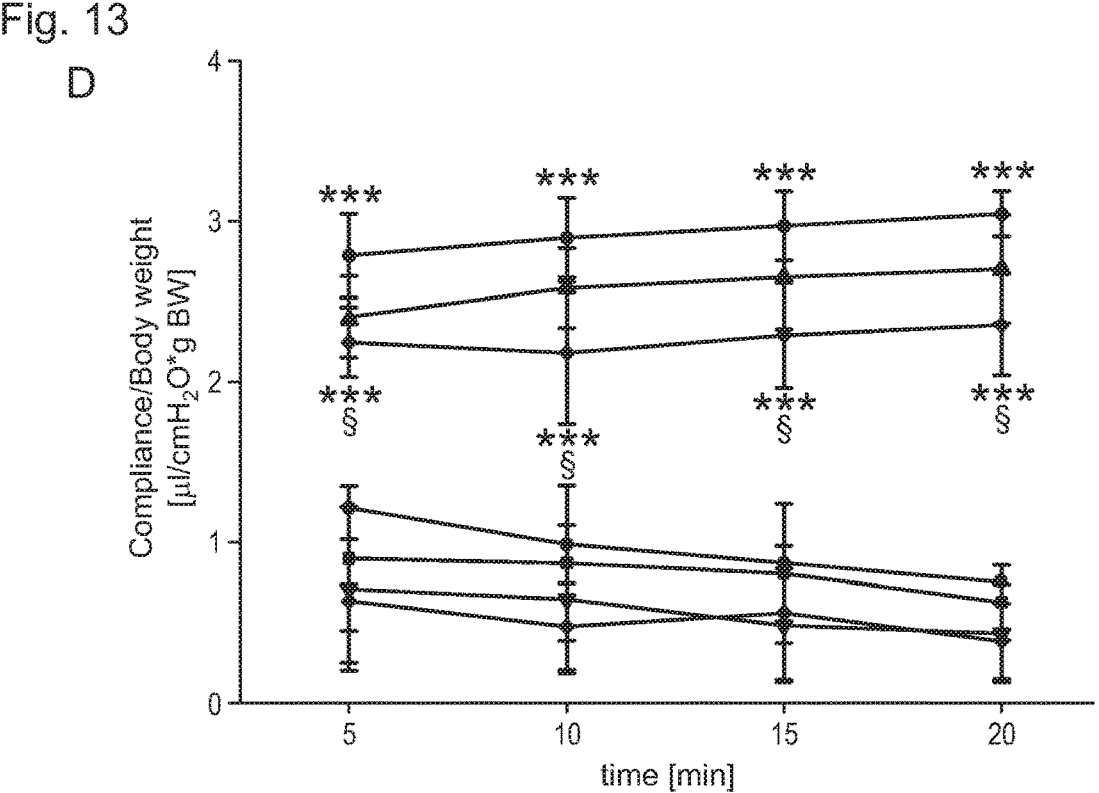
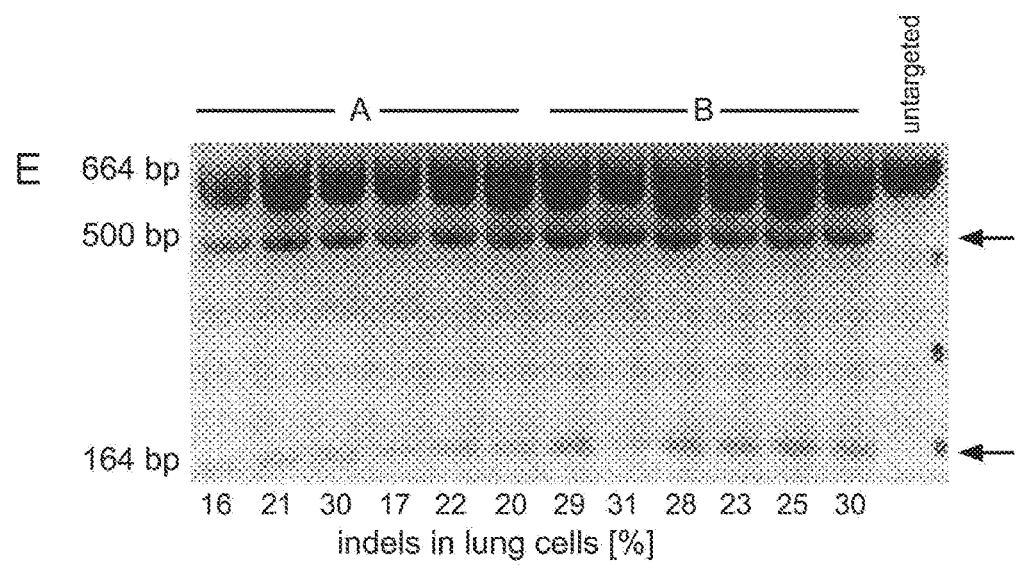
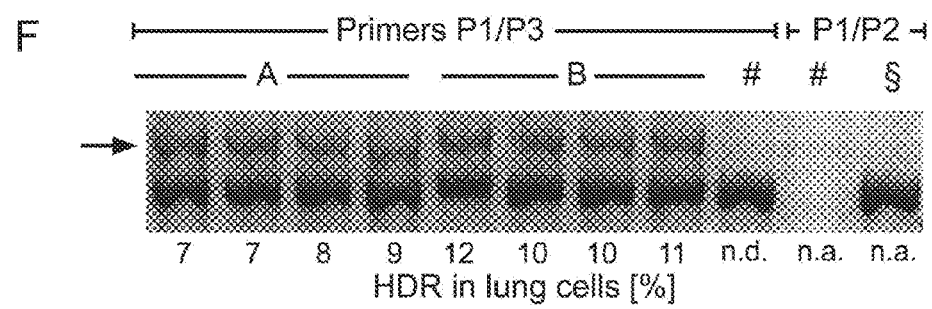

Fig. 13
G
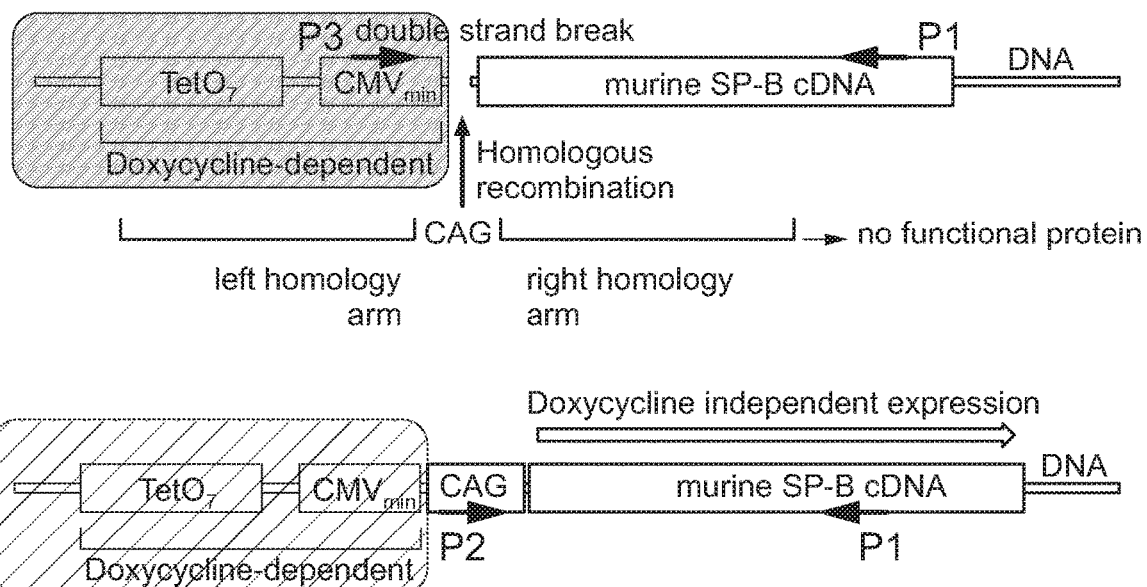
H
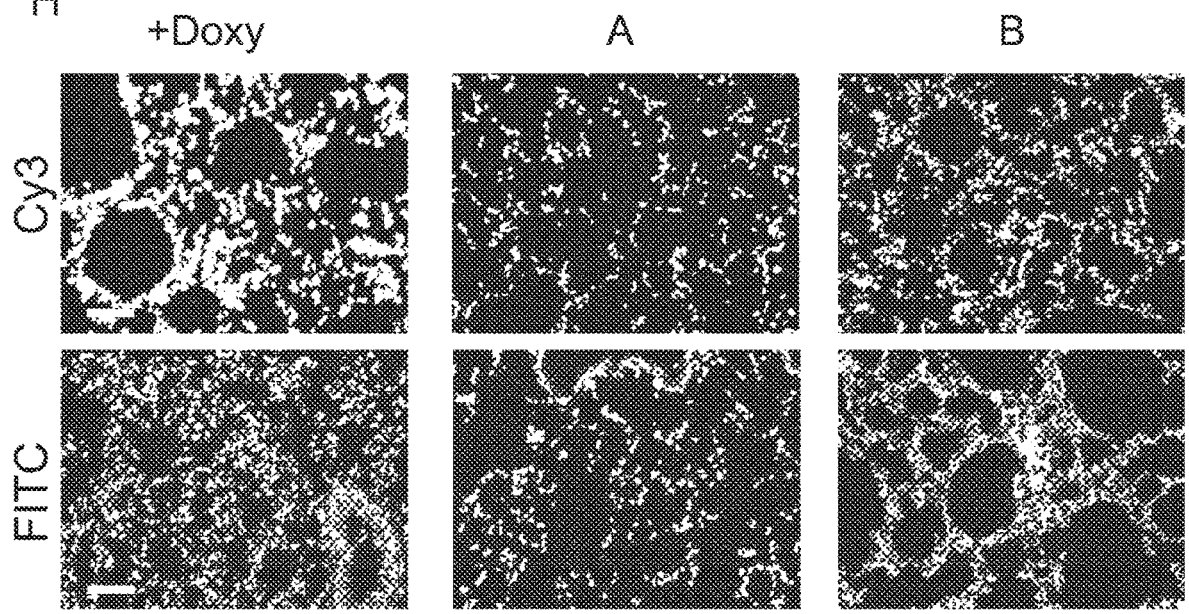

Fig. 14
A
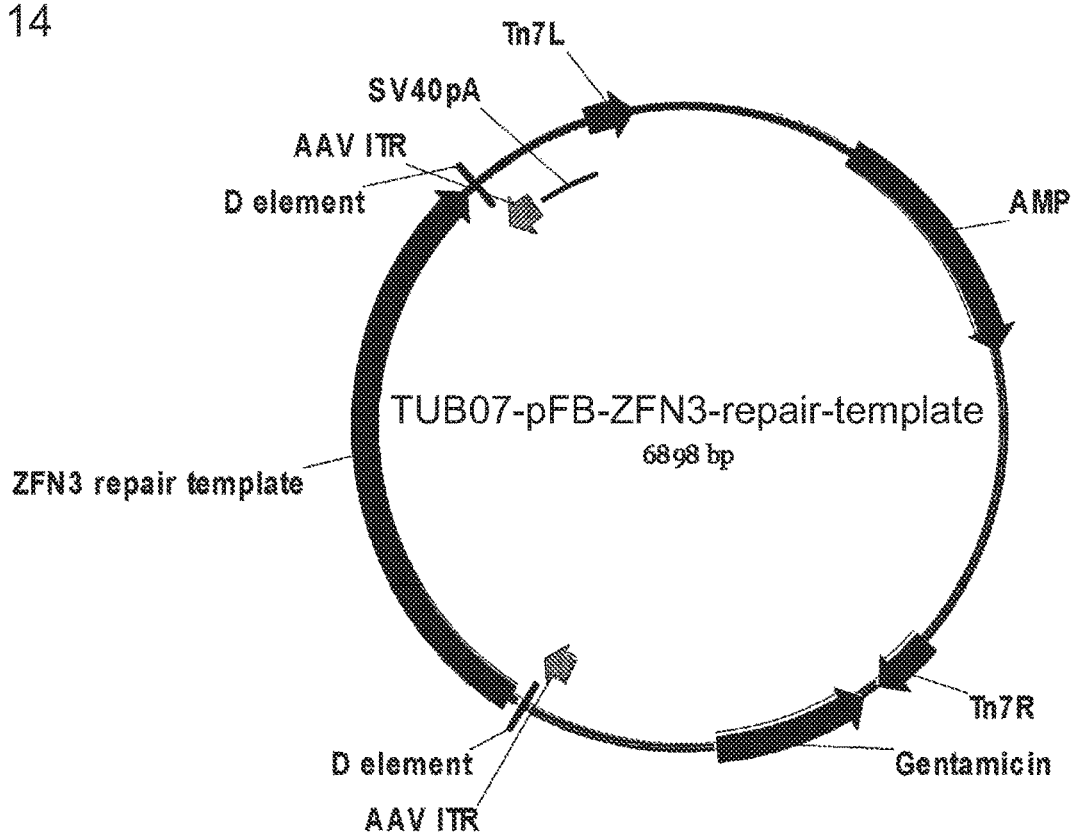
B
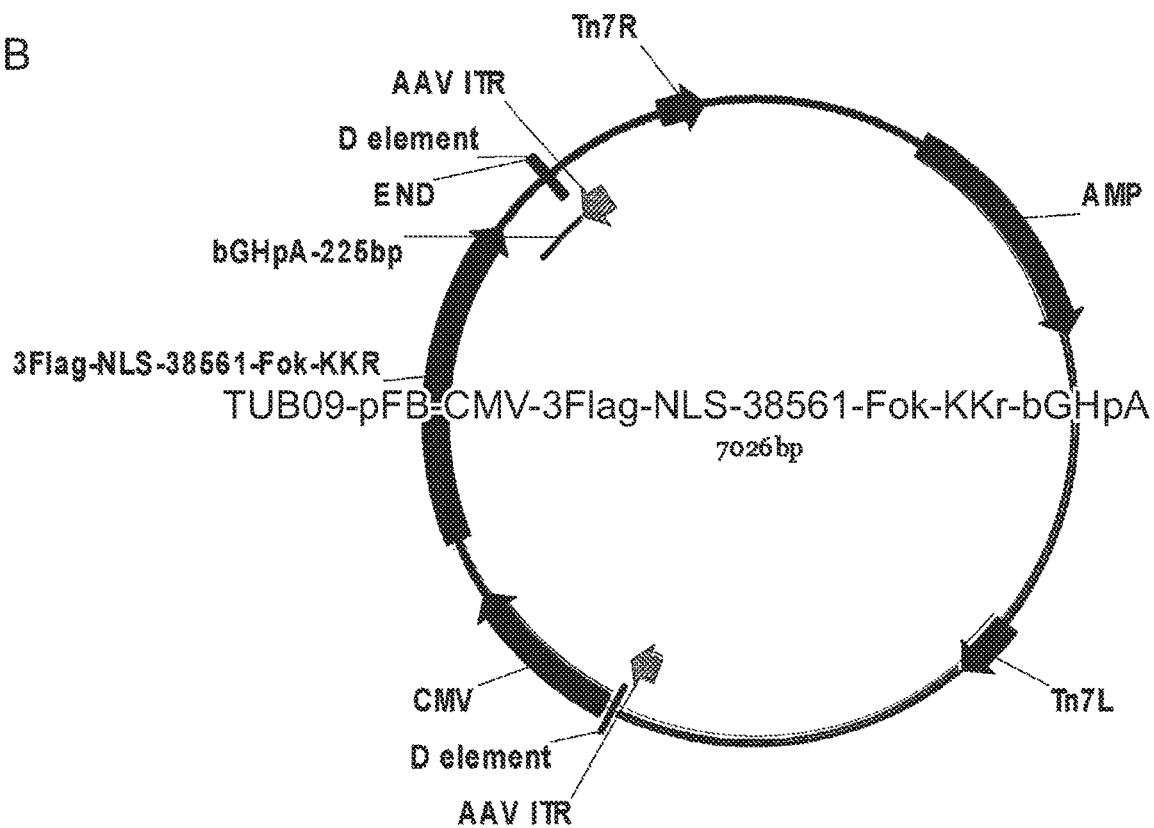

C

Fig. 19
+Doxy
before perfusion
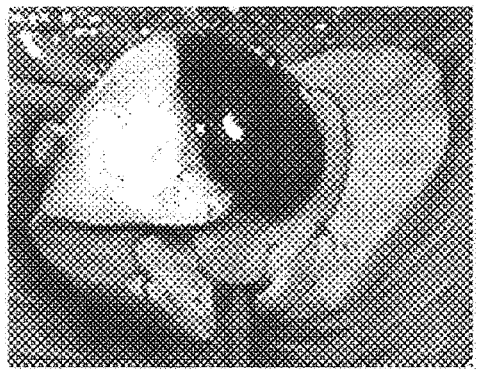
after perfusion
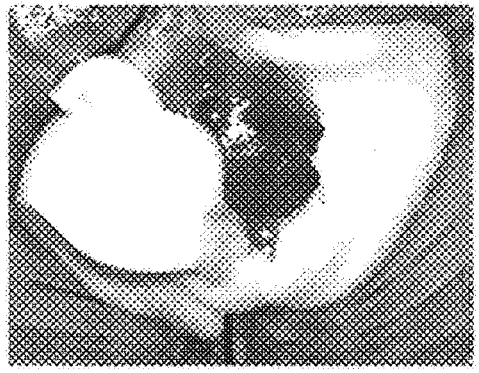
Group A (donor AAV, Z3 nec-mRNA, -Doxy)
before perfusion
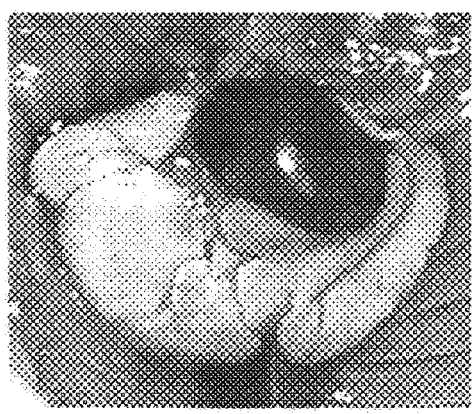
after perfusion
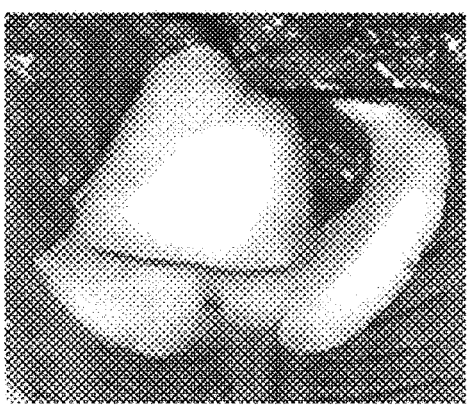
Group B (donor AAV, Z3 AAV, -Doxy)
before perfusion
after perfusion
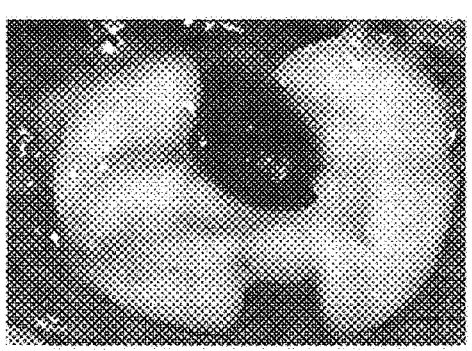

Fig. 20

Group C (donor AAV, mock-mRNA, -Doxy)

before perfusion

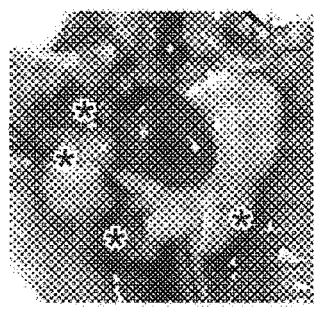

Asterisks indicate:
- right lung hemorr-
  hagic (esp. *cran-
  ialis/29medialis*)
- left lung hemorr-
  hagic spot after perfusion

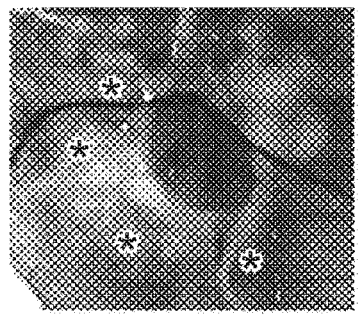

Asterisks indicate:
- right lung hemorr-
  hagic (esp. *cran-
  ialis/29medialis*)
- left lung hemorr-
  hagic spot

Group D (mock AAV, Z3 nec-mRNA, -Doxy)

before perfusion

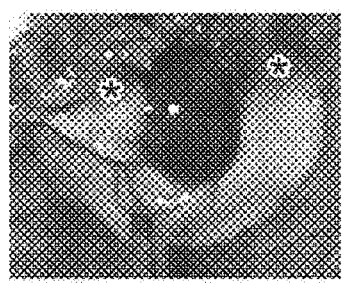

Asterisks indicate:
- left lung hemorr-
  hagic (cran-
  ialis section)
- right lung hemorr-
  hagic (esp. *cran-
  ialis*)

after perfusion

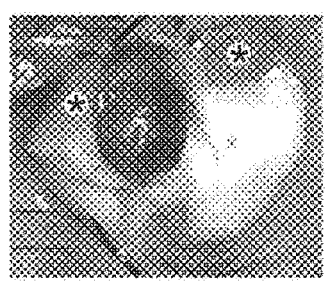

Asterisks indicate:
- left lung hemorr-
  hagic (cran-
  ialis section)
- right lung hemorr-
  hagic (esp. *cran-
  ialis*)

Group E (mock AAV, -Doxy)

before perfusion

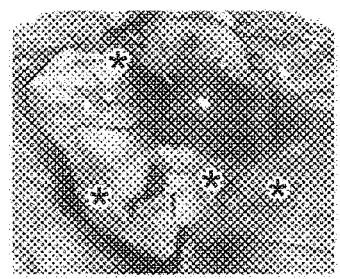

Asterisks indicate:
- left lung hemorr-
  hagic after perfusion

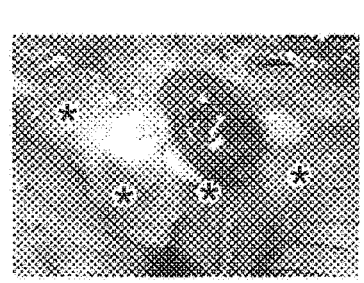

Asterisks indicate:
- left lung hemorr-
  hagic

Group F (no treatment, -Doxy)

before perfusion

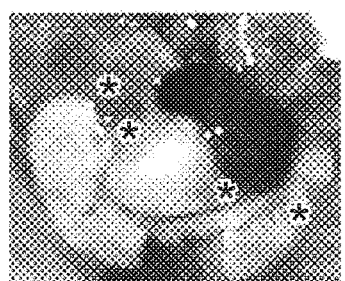

Asterisks indicate:
- *lobus caudalis*
  caudal left lung
  hemorrhagic after perfusion

Asterisks indicate:
- development of
  edemas arising
  from the hemorr-
  hagic areas

SEQUENCE LISTING

```
<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
gtaggcgtgt acggtgggag                                               20

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
cagcagaggg taggaagcag c                                             21

<210> SEQ ID NO 3
<211> LENGTH: 19
<212> TYPE: DNA
```

```
<213> ORGANISM: Artificial Sequence
<220> FEATURE:
<223> OTHER INFORMATION: PCR primer

<400> SEQUENCE: 3
tgtacggtgg gaggcctat                                                    19

<210> SEQ ID NO 4
<211> LENGTH: 17
<212> TYPE: DNA
<213> ORGANISM: Artificial Sequence
<220> FEATURE:
<223> OTHER INFORMATION: PCR primer

<400> SEQUENCE: 4
cctggcaggt gatgtgg                                                      17

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
gcaagtttgg cgtcgctcca                                                   20

<210> SEQ ID NO 6
<211> LENGTH: 18
<212> TYPE: DNA
<213> ORGANISM: Artificial Sequence
<220> FEATURE:
<223> OTHER INFORMATION: PCR primer

<400> SEQUENCE: 6
agaggaaggc gcggcagg                                                     18

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7
ttcttgctcc agtgactctc tta                                               23

<210> SEQ ID NO 8
<211> LENGTH: 24
<212> TYPE: DNA
<213> ORGANISM: Artificial Sequence
<220> FEATURE:
<223> OTHER INFORMATION: PCR primer

<400> SEQUENCE: 8
agcctagtaa agacaacact agtg                                              24

<210> SEQ ID NO 9
<211> LENGTH: 18
<212> TYPE: DNA
<213> ORGANISM: Artificial Sequence
<220> FEATURE:
<223> OTHER INFORMATION: PCR primer

<400> SEQUENCE: 9
caacgtgacc tgcgagcg                                                     18
```

<210> SEQ ID NO 10
<211> LENGTH: 19
<212> TYPE: DNA
<213> ORGANISM: Artificial Sequence
<220> FEATURE:
<223> OTHER INFORMATION: PCR primer

<400> SEQUENCE: 10
gtgcacgctc cacttctcg                                                   19

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
ctggagatgc atccttgtct gt                                               22

<210> SEQ ID NO 12
<211> LENGTH: 22
<212> TYPE: DNA
<213> ORGANISM: Artificial Sequence
<220> FEATURE:
<223> OTHER INFORMATION: PCR primer

<400> SEQUENCE: 12
gagggtgaag acttttggag ct                                               22

<210> SEQ ID NO 13
<211> LENGTH: 22
<212> TYPE: DNA
<213> ORGANISM: Artificial Sequence
<220> FEATURE:
<223> OTHER INFORMATION: PCR primer

<400> SEQUENCE: 13
cagcaccaga tgttccctgt ta                                               22

<210> SEQ ID NO 14
<211> LENGTH: 24
<212> TYPE: DNA
<213> ORGANISM: Artificial Sequence
<220> FEATURE:
<223> OTHER INFORMATION: PCR primer

<400> SEQUENCE: 14
tggaaagcaa tagttctagg atga                                             24

<210> SEQ ID NO 15
<211> LENGTH: 17
<212> TYPE: DNA
<213> ORGANISM: Artificial Sequence
<220> FEATURE:
<223> OTHER INFORMATION: PCR primer

<400> SEQUENCE: 15
cctggcaggt gatgtgg                                                     17

<210> SEQ ID NO 16
<211> LENGTH: 19
<212> TYPE: DNA
<213> ORGANISM: Artificial Sequence
<220> FEATURE:

<223> OTHER INFORMATION: PCR primer

<400> SEQUENCE: 16
tgtacggtgg gaggcctat                                           19

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
aggcactggg caggtaagta                                          20

<210> SEQ ID NO 18
<211> LENGTH: 18
<212> TYPE: DNA
<213> ORGANISM: Artificial Sequence
<220> FEATURE:
<223> OTHER INFORMATION: PCR primer

<400> SEQUENCE: 18
gtaaaacgac ggccagtg                                            18

<210> SEQ ID NO 19
<211> LENGTH: 21
<212> TYPE: DNA
<213> ORGANISM: Artificial Sequence
<220> FEATURE:
<223> OTHER INFORMATION: PCR primer

<400> SEQUENCE: 19
caggaaacag ctatgaccat g                                        21

<210> SEQ ID NO 20
<211> LENGTH: 18
<212> TYPE: DNA
<213> ORGANISM: Artificial Sequence
<220> FEATURE:
<223> OTHER INFORMATION: PCR primer

<400> SEQUENCE: 20
tgtacggcta caggggaa                                            18

<210> SEQ ID NO 21
<211> LENGTH: 18
<212> TYPE: DNA
<213> ORGANISM: Artificial Sequence
<220> FEATURE:
<223> OTHER INFORMATION: PCR primer

<400> SEQUENCE: 21
gccgataggc agattgta                                            18

<210> SEQ ID NO 22
<211> LENGTH: 17
<212> TYPE: DNA
<213> ORGANISM: Artificial Sequence
<220> FEATURE:
<223> OTHER INFORMATION: PCR primer

<400> SEQUENCE: 22
taggcaccag ggtgatg                                             17

```
<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
gccatgttca atggggtact                                                      20

<210> SEQ ID NO 24
<211> LENGTH: 1665
<212> TYPE: DNA
<213> ORGANISM: Artificial Sequence
<220> FEATURE:
<223> OTHER INFORMATION: Synthetic
<220> FEATURE:
<223> OTHER INFORMATION: Transgenic SP-B cassette (before gene
      manipulation)
<220> FEATURE:
<221> NAME/KEY: misc_feature
<222> LOCATION: (1628)..(1632)
<220> FEATURE:
<221> NAME/KEY: misc_feature
<222> LOCATION: (1628)..(1632)
<223> OTHER INFORMATION: n is a, c, g, or t

<400> SEQUENCE: 24
cctcgagttt accactccct atcagtgata gagaaaagtg aaagtcgagt ttaccactcc          60
ctatcagtga tagagaaaag tgaaagtcga gtttaccact ccctatcagt gatagagaaa         120
agtgaaagtc gagtttacca ctccctatca gtgatagaga aaagtgaaag tcgagtttac         180
cactccctat cagtgataga gaaaagtgaa agtcgagttt accactccct atcagtgata         240
gagaaaagtg aaagtcgagt ttaccactcc ctatcagtga tagagaaaag tgaaagtcga         300
gctcggtacc cgggtcgagg taggcgtgta cggtgggagg cctatataag cagagctcgt         360
ttagtgaacc gtcagatcgc ctggagacgc catccacgct gttttgacct ccatagaaga         420
caccgggacc gatccagcct ccgcggcccc gaattctgca gatatccagc acagtggcgg         480
ccgctaggca gccatggcca agtcgcacct actgcagtgg ctactgctgc ttcctaccct         540
ctgctgccca ggtgcagcta tcacgtcggc ctcatccctg gagtgtgcac aaggccctca         600
attctggtgc caaagcctgg agcatgcagt gcagtgcaga gccctggggc actgcctgca         660
ggaagtctgg gggcatgcag gagctaatga cctgtgccaa gagtgtgagg atattgtcca         720
cctcctcaca aagatgacca aggaagatgc tttccaggaa gcaatccgga agttcctgga         780
acaagaatgt gatatccttc ccttgaagct gcttgtgccc cggtgtcgcc aagtgcttga         840
tgtctacctg cccctggtta ttgactactt ccagagccag attaacccca agccatctg          900 caatcatgtg ggcctgtgcc acgtgggca ggctaagcca aacagaatc cagggatgcc           960 ggatgccgtt ccaaaccctc tgctggacaa gctggtcctc cctgtgctgc caggagccct        1020
cttggcaagg cctgggcctc acactcagga cttctctgag caacagctcc ccattcccct        1080 gccctttctgc tggctttgca gaactctgat caagcgggtt caagccgtga tccccaaggg        1140
tgtgctggct gtggctgtgt cccaggtgtg ccacgtggta cccctggtgg tgggtggcat        1200
ctgccagtgc ctggctgagc gctacacagt tctcctgcta gacgcactgc tgggccgtgt        1260
ggtgccccag ctagtctgtg gccttgtcct ccgatgttcc actgaggatg ccatgggccc        1320
tgccctccct gctgtggagc ctctgataga agaatggcca ctacaggaca ctgagtgcca        1380
tttctgcaag tctgtgatca accaggcctg gaacaccagt gaacaggcta tgccacaggc        1440
```

```
aatgcaccag gcctgccttc gcttctggct agacaggcaa aagtgtgaac agtttgtgga    1500
acagcacatg ccccagctgc tggccctggt gcctaggagc caggatgccc acatcacctg    1560
ccaggccctt ggcgtatgtg aggccccggc tagccctctg cagtcgttcc aaaccccaca    1620
cctctgannn nntctagagg gcccgtttaa acccgctgat cagcc                    1665
```

<210> SEQ ID NO 25
<211> LENGTH: 2640
<212> TYPE: DNA
<213> ORGANISM: Artificial Sequence
<220> FEATURE:
<223> OTHER INFORMATION: Synthetic
<220> FEATURE:
<223> OTHER INFORMATION: Transgenic SP-B cassette (after gene
      manipulation)
<220> FEATURE:
<221> NAME/KEY: misc_feature
<222> LOCATION: (2603)..(2607)
<220> FEATURE:
<221> NAME/KEY: misc_feature
<222> LOCATION: (2603)..(2607)
<223> OTHER INFORMATION: n is a, c, g, or t

<400> SEQUENCE: 25

```
cctcgagttt accactccct atcagtgata gagaaaagtg aaagtcgagt ttaccactcc     60
ctatcagtga tagagaaaag tgaaagtcga gtttaccact ccctatcagt gatagagaaa    120
agtgaaagtc gagtttacca ctccctatca gtgatagaga aaagtgaaag tcgagtttac    180
cactccctat cagtgataga gaaagtgaa agtcgagttt accactccct atcagtgata    240
gagaaaagtg aaagtcgagt ttaccactcc ctatcagtga tagagaaaag tgaaagtcga    300
gctcggtacc cgggtcgagg taggcgtgta cggtgggagg cctatataag cagagctcgt    360
ttagtgaacc gtcagatcgc ctggagacgc catccacgct gttttgacct ccatagaaga    420
caccgggcta gcggatcctc tagaactata gctagtcgac attgattatt gactagttat    480
taatagtaat caattacggg gtcattagtt catagcccat atatggagtt ccgcgttaca    540
taacttacgg taaatggccc gcctggctga ccgcccaacg acccccgccc attgacgtca    600
ataatgacgt atgttcccat agtaacgcca tagggactt tccattgacg tcaatgggtg    660
gactatttac ggtaaactgc ccacttggca gtacatcaag tgtatcatat gccaagtacg    720
ccccctattg acgtcaatga cggtaaatgg cccgcctggc attatgccca gtacatgacc    780
ttatgggact ttcctacttg gcagtacatc tacgtattag tcatcgctat taccatgtcg    840
aggccacgtt ctgcttcact ctccccatct ccccccctc cccaccccca ttttgtatt    900 tatttatttt ttaattattt tgtgcagcga tggggcggg ggggggggc gcgcgccagg    960 cggggcgggg cggggcgagg ggcggggcgg ggcgaggcgg agaggtgcgg cggcagccaa   1020
tcagagcggc gcgctccgaa agtttccttt tatggcgagg cggcggcggc ggcggccta    1080 taaaaagcga agcgcgcggc gggcgggagc aagctttatt gcggtagttt atcacagtta   1140
aattgctaac gcagtcagtg cttctgacac aacagtctcg aacttaagct gcagaagttg    1200
gtcgtgaggc actgggcagg taagtatcaa ggttacaaga caggtttaag gagaccaata    1260
gaaactgggc ttgtcgagac agagaagact cttgcgttc tgataggcac ctattggtct    1320
tactgacatc cactttgcct ttctctccac aggtgtccac tcccagttca attacagctc    1380
ttaaggctag agtacttaat acgactcact ataggctagc ctcgagaatt ctgcagatat    1440
ccagcacagt ggcggccgct aggcagccat ggccaagtcg cacctactgc agtggcact    1500 gctgcttcct accctctgct gcccaggtgc agctatcacg tcggcctcat ccctggagtg   1560
```

| | | | |
|---|---|---|---|
| tgcacaaggc | cctcaattct | ggtgccaaag | cctggagcat gcagtgcagt gcagagccct | 1620 |
| ggggcactgc | ctgcaggaag | tctgggggca | tgcaggagct aatgacctgt gccaagagtg | 1680 |
| tgaggatatt | gtccacctcc | tcacaaagat | gaccaaggaa gatgctttcc aggaagcaat | 1740 |
| ccggaagttc | ctggaacaag | aatgtgtatc | cttcccttg aagctgcttg tgccccggtg | 1800 |
| tcgccaagtg | cttgatgtct | acctgccct | ggttattgac tacttccaga gccagattaa | 1860 |
| ccccaaagcc | atctgcaatc | atgtgggcct | gtgcccacgt gggcaggcta agccagaaca | 1920 |
| gaatccaggg | atgccggatg | ccgttccaaa | ccctctgctg gacaagctgg tcctccctgt | 1980 |
| gctgccagga | gccctcttgg | caaggcctgg | gcctcacact caggacttct ctgagcaaca | 2040 |
| gctccccatt | ccctgccct | tctgctggct | ttgcagaact ctgatcaagc gggttcaagc | 2100 |
| cgtgatcccc | aagggtgtgc | tggctgtggc | tgtgtcccag gtgtgccacg tggtacccct | 2160 |
| ggtggtgggt | ggcatctgcc | agtgcctggc | tgagcgctac acagttctcc tgctagacgc | 2220 |
| actgctgggc | cgtgtggtgc | cccagctagt | ctgtggcctt gtcctccgat gttccactga | 2280 |
| ggatgccatg | ggccctgccc | tccctgctgt | ggagcctctg atagaagaat ggccactaca | 2340 |
| ggacactgag | tgccatttct | gcaagtctgt | gatcaaccag gcctgaaaca ccagtgaaca | 2400 |
| ggctatgcca | caggcaatgc | accaggcctg | ccttcgcttc tggctagaca ggcaaaagtg | 2460 |
| tgaacagttt | gtggaacagc | acatgcccca | gctgctggcc ctggtgccta ggagccagga | 2520 |
| tgcccacatc | acctgccagg | cccttggcgt | atgtgaggcc ccggctagcc ctctgcagtc | 2580 |
| gttccaaacc | ccacacctct | gannnnntct | agagggcccg tttaaacccg ctgatcagcc | 2640 |

<210> SEQ ID NO 26
<211> LENGTH: 6122
<212> TYPE: DNA
<213> ORGANISM: Artificial Sequence
<220> FEATURE:
<223> OTHER INFORMATION: Synthetic
<220> FEATURE:
<223> OTHER INFORMATION: pVAX1 A120 TALEN 1 LEFT

<400> SEQUENCE: 26

| | | | |
|---|---|---|---|
| gactcttcgc | gatgtacggg | ccagatatac | gcgttgacat tgattattga ctagttatta | 60 |
| atagtaatca | attacggggt | cattagttca | tagcccatat atggagttcc gcgttacata | 120 |
| acttacggta | aatggcccgc | ctggctgacc | gcccaacgac ccccgcccat tgacgtcaat | 180 |
| aatgacgtat | gttcccatag | taacgccaat | agggactttc cattgacgtc aatgggtgga | 240 |
| ctatttacgg | taaactgccc | acttggcagt | acatcaagtg tatcatatgc caagtacgcc | 300 |
| ccctattgac | gtcaatgacg | gtaaatggcc | cgcctggcat tatgcccagt acatgacctt | 360 |
| atgggacttt | cctacttggc | agtacatcta | cgtattagtc atcgctatta ccatggtgat | 420 |
| gcggttttgg | cagtacatca | atgggcgtgg | atagcggttt gactcacggg gatttccaag | 480 |
| tctccacccc | attgacgtca | atgggagttt | gttttggcac caaaatcaac gggactttcc | 540 |
| aaaatgtcgt | aacaactccg | ccccattgac | gcaaatgggc ggtaggcgtg tacggtggga | 600 |
| ggtctatata | agcagagctc | tctggctaac | tagagaaccc actgcttact ggcttatcga | 660 |
| aattaatacg | actcactata | gggagaccca | agctggctag cgtttaaact taagcttggt | 720 |
| accgagctcg | gatccactag | tccagtgtgg | tggaattagc tctctggcta actagagaac | 780 |
| ccactgctta | ctggcttatc | gaaattaata | cgactcacta gggagagc caagctgact | 840 |
| agcgtttaaa | cttaagctga | tccactagtc | cagtgtggtg gaattcgcca tggactacaa | 900 |

```
agaccatgac ggtgattata aagatcatga catcgattac aaggatgacg atgacaagat    960
ggccccccaag aagaagagga aggtcggcat ccacggggta cctatggtgg acttgaggac   1020
actcggttat tcgcaacagc aacaggagaa aatcaagcct aaggtcagga gcaccgtcgc   1080
gcaacaccac gaggcgcttg tggggcatgg cttcactcat gcgcatattg tcgcgctttc   1140
acagcaccct gcggcgcttg ggacggtggc tgtcaaatac aagatatga ttgcggccct   1200
gcccgaagcc acgcacgagg caattgtagg ggtcggtaaa cagtggtcgg agcgcgagc   1260
acttgaggcg ctgctgactg tggcgggtga gcttagggg cctccgctcc agctcgacac   1320
cgggcagctg ctgaagatcg cgaagagagg gggagtaaca gcggtagagg cagtgcacgc   1380
ctggcgcaat gcgctcaccg ggccccctt gaacctgacc ccagaccagg tagtcgcaat   1440
cgcgtcgaat ggcgggggaa agcaagccct ggaaaccgtg caaaggttgt tgccggtcct   1500
ttgtcaagac cacggcctta caccggatca agtcgtggcc attgcaaata ataacggtgg   1560
caaacaggct cttgagacgg ttcagagact tctcccagtt ctctgtcaag cccacgggct   1620
gactcccgat caagttgtag cgattgcgag caacatcgga gggaaacaag cattggagac   1680
tgtccaacgg ctccttcccg tgttgtgtca agcccacggt ttgacgcctg cacaagtggt   1740
cgccatcgcc tcccacgacg gcggtaagca ggcgctggaa acagtacagc gcctgctgcc   1800
tgtactgtgc caggatcatg gactcacccc agaccaggta gtcgcaatcg cgtcgcatga   1860
cgggggaaag caagccctgg aaaccgtgca aaggttgttg ccggtccttt gtcaagacca   1920
cggccttaca ccggagcaag tcgtggccat tgcatcaaac ggaggtggca aacaggctct   1980
tgagacggtt cagagacttc tcccagttct ctgtcaagcc cacggctga ctcccgatca   2040
agttgtagcg attgcgagcc atgatggagg gaaacaagca ttggagactg tccaacggct   2100
ccttcccgtg ttgtgtcaag cccacggttt gacgcctgca caagtggtcg ccatcgactc   2160
ccacgacggc ggtaagcagg cgctggaaac agtacagcgc ctgctgcctg tactgtgcca   2220
ggatcatggg ctgaccccag accaggtagt cgcaatcgcg tcgaacattg ggggaaagca   2280
agccctggaa accgtgcaaa ggttgttgcc ggtcctttgt caagaccacg ccttacacc   2340
ggagcaagtc gtggccattg catcaaacgg aggtggcaaa caggctcttg agacggttca   2400
gagacttctc ccagttctct gtcaagccca cgggctgact cccgatcaag ttgtagcgat   2460
tgcgagcaac atcggaggga acaagcatt ggagactgtc caacggctcc ttcccgtgtt   2520
gtgtcaagcc cacggtttga cgcctgcaca agtggtcgcc atcgcaaca caacggcgg   2580
taagcaggcg ctggaaacag tacagcgcct gctgcctgta ctgtgccagg atcatggttt   2640
gaccccagac caggtagtcg caatcgcgtc gaacattggg ggaaagcaag ccctggaaac   2700
cgtgcaaagg ttgttgccgg tcctttgtca agaccacggc cttacaccgg agcaagtcgt   2760
ggccattgca tcaaatatcg gtggcaaaca ggctcttgag acggttcaga cttctccc    2820
agttctctgt caagcccacg ggctgactcc cgatcaagtt gtagcgattg cgaataacaa   2880
tggagggaaa caagcattgg agactgtcca acggctcctt cccgtgttgt gtcaagccca   2940
cggtttgacg cctgcacaag tggtcgccat cgcctccaat attggcggta agcaggcgct   3000
ggaaacagta cagcgcctgc tgcctgtact gtgccaggat catggcctga cccgaaca   3060
ggtggtcgcc attgctagcc acgatggagg acggccagcc ttggagtcca tcgtagccca   3120
attgtccagg cccgatcccg cgttggctgc gttaacggga tcccagctgg tgaagagcga   3180
gctgaggag aagaagtccg agctgcggca caagctgaag tacgtgcccc acgagtacat   3240
cgagctgatc gagatcgcca ggaacagcac ccaggaccgc atcctggaga tgaaggtgat   3300
```

```
ggagttcttc atgaaggtgt acggctacag gggaaagcac ctgggcggaa gcagaaagcc    3360
tgacggcgcc atctatacag tgggcagccc catcgattac ggcgtgatcg tggacacaaa    3420
ggcctacagc ggcggctaca atctgcctat cggccaggcc gacgagatgg agagatacgt    3480
ggaggagaac cagacccggg ataagcacct caaccccaac gagtggtgga aggtgtaccc    3540
tagcagcgtg accgagttca agttcctgtt cgtgagcggc cacttcaagg gcaactacaa    3600
ggcccagctg accaggctga accacatcac caactgcaat ggcgccgtgc tgagcgtgga    3660
ggagctgctg atcggcggcg agatgatcaa agccggcacc ctgacactgg aggaggtgcg    3720
gcgcaagttc aacaacggcg agatcaactt cagatcttga taactcgagc taattctgca    3780
gaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
agcggccgct cgagtctaga gggcccgttt aaacccgctg atcagcctcg actgtgcctt    3960
ctagttgcca gccatctgtt gtttgcccct cccccgtgcc ttccttgacc ctggaaggtg    4020
ccactcccac tgtcctttcc taataaaatg aggaaattgc atcgcattgt ctgagtaggt    4080
gtcattctat tctggggggt ggggtggggc aggacagcaa ggggggaggat tgggaagaca    4140
atagcaggca tgctggggat gcggtgggct ctatggcttc tactgggcgg ttttatggac    4200
agcaagcgaa ccggaattgc cagctggggc gccctctggt aaggttggga agccctgcaa    4260
agtaaactgg atggctttct cgccgccaag gatctgatgg cgcagggat caagctctga    4320
tcaagagaca ggatgaggat cgtttcgcat gattgaacaa gatggattgc acgcaggttc    4380
tccggccgct tgggtggaga ggctattcgg ctatgactgg gcacaacaga caatcggctg    4440
ctctgatgcc gccgtgttcc ggctgtcagc gcaggggcgc ccggttcttt ttgtcaagac    4500
cgacctgtcc ggtgccctga tgaactgca agacgaggca gcgcggctat cgtggctggc    4560
cacgacgggc gttccttgcg cagctgtgct cgacgttgtc actgaagcgg gaagggactg    4620
gctgctattg ggcgaagtgc cggggcagga tctcctgtca tctcaccttg ctcctgccga    4680
gaaagtatcc atcatggctg atgcaatgcg gcggctgcat acgcttgatc cggctacctg    4740
cccattcgac caccaagcga aacatcgcat cgagcgagca cgtactcgga tggaagccgg    4800
tcttgtcgat caggatgatc tggacgaaga gcatcagggg ctcgcgccag ccgaactgtt    4860
cgccaggctc aaggcgagca tgcccgacgg cgaggatctc gtcgtgaccc atggcgatgc    4920
ctgcttgccg aatatcatgg tggaaaatgg ccgcttttct ggattcatcg actgtggccg    4980
gctgggtgtg gcggaccgct atcaggacat agcgttggct acccgtgata ttgctgaaga    5040
gcttggcggc gaatgggctg accgcttcct cgtgctttac ggtatcgccg ctcccgattc    5100
gcagcgcatc gccttctatc gccttcttga cgagttcttc tgaattatta acgcttacaa    5160
tttcctgatg cggtattttc tccttacgca tctgtgcggt atttcacacc gcatacaggt    5220
ggcacttttc ggggaaatgt gcgcggaacc cctatttgtt tatttttcta aatacattca    5280
aatatgtatc cgctcatgag acaataaccc tgataaatgc ttcaataata gcacgtgcta    5340
aaacttcatt tttaatttaa aaggatctag gtgaagatcc ttttttgataa tctcatgacc    5400
aaaatccctt aacgtgagtt ttcgttccac tgagcgtcag accccgtaga aaagatcaaa    5460
ggatcttctt gagatccttt ttttctgcgc gtaatctgct gcttgcaaac aaaaaaacca    5520
ccgctaccag cggtggtttg tttgccggat caagagctac caactctttt tccgaaggta    5580
actggcttca gcagagcgca gataccaaat actgtccttc tagtgtagcc gtagttaggc    5640
```

| | | | | |
|---|---|---|---|---|
| caccacttca | agaactctgt | agcaccgcct | acatacctcg ctctgctaat | cctgttacca | 5700 |
| gtggctgctg | ccagtggcga | taagtcgtgt | cttaccgggt tggactcaag | acgatagtta | 5760 |
| ccggataagg | cgcagcggtc | gggctgaacg | ggggttcgt gcacacagcc | cagcttggag | 5820 |
| cgaacgacct | acaccgaact | gagataccta | cagcgtgagc tatgagaaag | cgccacgctt | 5880 |
| cccgaaggga | gaaaggcgga | caggtatccg | gtaagcggca gggtcggaac | aggagagcgc | 5940 |
| acgagggagc | ttccagggggg | aaacgcctgg | tatctttata gtcctgtcgg | gtttcgccac | 6000 |
| ctctgacttg | agcgtcgatt | tttgtgatgc | tcgtcagggg gcggagcct | atggaaaaac | 6060 |
| gccagcaacg | cggcctttt | acggttcctg | gccttttgct ggccttttgc | tcacatgttc | 6120 |
| tt | | | | 6122 |

<210> SEQ ID NO 27
<211> LENGTH: 6194
<212> TYPE: DNA
<213> ORGANISM: Artificial Sequence
<220> FEATURE:
<223> OTHER INFORMATION: Synthetic
<220> FEATURE:
<223> OTHER INFORMATION: pVAX1 A120 TALEN 1 RIGHT

<400> SEQUENCE: 27

| | | | | |
|---|---|---|---|---|
| gactcttcgc | gatgtacggg | ccagatatac | gcgttgacat tgattattga | ctagttatta | 60 |
| atagtaatca | attacggggt | cattagttca | tagcccatat atggagttcc | gcgttacata | 120 |
| acttacggta | aatggcccgc | ctggctgacc | gcccaacgac cccgcccat | tgacgtcaat | 180 |
| aatgacgtat | gttcccatag | taacgccaat | agggactttc cattgacgtc | aatgggtgga | 240 |
| ctatttacgg | taaactgccc | acttggcagt | acatcaagtg tatcatatgc | caagtacgcc | 300 |
| ccctattgac | gtcaatgacg | gtaaatggcc | cgcctggcat tatgcccagt | acatgacctt | 360 |
| atgggacttt | cctacttggc | agtacatcta | cgtattagtc atcgctatta | ccatggtgat | 420 |
| gcggttttgg | cagtacatca | atgggcgtgg | atagcggttt gactcacggg | gatttccaag | 480 |
| tctccacccc | attgacgtca | atgggagttt | gttttggcac caaaatcaac | gggactttcc | 540 |
| aaaatgtcgt | aacaactccg | ccccattgac | gcaaatgggc ggtaggcgtg | tacggtggga | 600 |
| ggtctatata | agcagagctc | tctggctaac | tagagaaccc actgcttact | ggcttatcga | 660 |
| aattaatacg | actcactata | gggagaccca | agctggctag cgtttaaact | taagcttggt | 720 |
| accgagctcg | gatccactag | tccagtgtgg | tggaattagc tctctggcta | actagagaac | 780 |
| ccactgctta | ctggcttatc | gaaattaata | cgactcacta gggagagc | caagctgact | 840 |
| agcgtttaaa | cttaagctga | tccactagtc | cagtgtggtg gaattcgcct | agagatctgg | 900 |
| cggcggagag | ggcagaggaa | gtcttctaac | ctgcggtgac gtggaggaga | atcccggccc | 960 |
| taggaccatg | gactacaaag | accatgacgg | tgattataaa gatcatgaca | tcgattacaa | 1020 |
| ggatgacgat | gacaagatgg | cccccaagaa | gaagaggaag gtcggcattc | atggggtacc | 1080 |
| tatgtggac | ttgaggacac | tcggttattc | gcaacagcaa caggagaaaa | tcaagcctaa | 1140 |
| ggtcaggagc | accgtcgcgc | aacaccacga | ggcgcttgtg gggcatggct | tcactcatgc | 1200 |
| gcatattgtc | gcgctttcac | agcacccctg | ggcgcttggg acgtggctg | tcaaatacca | 1260 |
| agatatgatt | gcggccctgc | ccgaagccac | gcacgaggca attgtagggg | tcggtaaaca | 1320 |
| gtggtcggga | gcgcgagcac | ttgaggcgct | gctgactgtg gcgggtgagc | ttaggggggcc | 1380 |
| tccgctccag | ctcgacaccg | gcagctgct | gaagatcgcg aagagagggg | gagtaacagc | 1440 |
| ggtagaggca | gtgcacgcct | ggcgcaatgc | gctcaccggg gcccccttga | acctgacccc | 1500 |

```
agaccaggta gtcgcaatcg cgtcgcatga cggggggaaag caagccctgg aaaccgtgca    1560
aaggttgttg ccggtccttt gtcaagacca cggccttaca ccggatcaag tcgtggccat    1620
tgcaaataat aacggtggca acaggctct tgagacggtt cagagacttc tcccagttct     1680
ctgtcaagcc cacgggctga ctcccgatca agttgtagcg attgcgaata caatgcgagg    1740
gaaacaagca ttggagactg tccaacggct ccttcccgtg ttgtgtcaag cccacggttt    1800
gacgcctgca caagtggtcg ccatcgccaa caacaacggc ggtaagcagg cgctggaaac    1860
agtacagcgc ctgctgcctg tactgtgcca ggatcatgga ctcaccccag accaggtagt    1920
cgcaatcgcc aacaataacg ggggaaagca agccctggaa accgtgcaaa ggttgttgcc    1980
ggtcctttgt caagaccacg gccttacacc ggagcaagtc gtggccattg catcacatga    2040
cggtggcaaa caggctcttg agacggttca gagacttctc ccagttctct gtcaagccca    2100
cgggctgact cccgatcaag ttgtagcgat tgcgagccat gatggaggga aacaagcatt    2160
ggagactgtc caacggctcc ttcccgtgtt gtgtcaagcc cacggtttga cgcctgcaca    2220
agtggtcgcc atcgccaaca caacggcgg taagcaggcg ctggaaacag tacagcgcct    2280
gctgcctgta ctgtgccagg atcatggggct gaccccagac caggtagtcg caatcgcgtc    2340
gcatgacggg ggaaagcaag ccctggaaac cgtgcaaagg ttgttgccgg tcctttgtca    2400
agaccacggc cttacaccgg atcaagtcgt ggccattgca ataataacg gtggcaaaca    2460 ggctcttgag acggttcaga gacttctccc agttctctgt caagcccacg ggctgactcc    2520
cgatcaagtt gtagcgattg cgaataacaa tggagggaaa caagcattgg agactgtcca    2580
acggctcctt cccgtgttgt gtcaagccca cggtttgacg cctgcacaag tggtcgccat    2640
cgcctccaat attggcggta agcaggcgct ggaaacagta cagcgcctgc tgcctgtact    2700
gtgccaggat catggtttga ccccagacca ggtagtcgca atcgccaaca ataacggggg    2760
aaagcaagcc ctggaaaccg tgcaaaggtt gttgcaggtc ctttgtcaag accacggcct    2820
tacaccggat caagtcgtgg ccattgcaaa taataacggt ggcaaacagg ctcttgagac    2880
ggttcagaga cttctcccag ttctctgtca agcccacggg ctgactcccg atcaagttgt    2940
agcgattgcg agccatgatg gagggaaaca agcattggag actgtccaac ggctccttcc    3000
cgtgttgtgt caagcccacg gtttgacgcc tgcacaagtg tcgccatcg cctccaacgg    3060 tggcggtaag caggcgctgg aaacagtaca gcgcctgctg cctgtactgt gccaggatca    3120
tggcctgaca cccgaacagg tggtcgccat tgctagcaat aaaggaggac ggccagcctt    3180
ggagtccatc gtagcccaat tgtccaggcc cgatcccgcg ttggctgcgt taacgggatc    3240
ccagctggtg aagagcgagc tggaggagaa gaagtccgag ctgcggcaca agctgaagta    3300
cgtgccccac gagtacatcg agctgatcga gatcgccagg aacagcaccc aggaccgcat    3360
cctggagatg aaggtgatgg agttcttcat gaaggtgtac ggctacaggg aaagcaccct    3420
gggcggaagc agaaagcctg acggcgccat ctatacagtg gcagccccca tcgattacgg    3480
cgtgatcgtg gacacaaagg cctacagcgg cggctacaat ctgcctatcg ccaggccga    3540 cgagatgcag agatacgtga aggagaacca gaccccggaat aagcacatca accccaacga    3600
gtggtggaag gtgtacccta gcagcgtgac cgagttcaag ttcctgttcg tgagcggcca    3660
cttcaagggc aactacaagg cccagctgac caggctgaac cgcaaaacca actgcaatgg    3720
cgccgtgctg agcgtggagg agctgctgat cggcggcgag atgatcaaag ccggcacccc    3780
gacactggag gaggtgcggc gcaagttcaa caacggcgag atcaacttct gataactcga    3840
```

```
gctaattctg cagaaaaaaa aaaaaaaaaa aaaaaaaaaa aaaaaaaaaa aaaaaaaaaa      3900
aaaaaaaaaa aaaaaaaaaa aaaaaaaaaa aaaaaaaaaa aaaaaaaaaa aaaaaaaaaa      3960
aaaaaaaaaa aaagcggccg ctcgagtcta gagggcccgt ttaaacccgc tgatcagcct      4020
cgactgtgcc ttctagttgc cagccatctg ttgtttgccc ctcccccgtg ccttccttga      4080
ccctggaagg tgccactccc actgtccttt cctaataaaa tgaggaaatt gcatcgcatt      4140
gtctgagtag gtgtcattct attctggggg gtggggtggg gcaggacagc aaggggagg       4200 attgggaaga caatagcagg catgctgggg atgcggtggg ctctatggct tctactgggc      4260
ggttttatgg acagcaagcg aaccggaatt gccagctggg gcgccctctg gtaaggttgg      4320
gaagccctgc aaagtaaact ggatggcttt ctcgccgcca aggatctgat ggcgcagggg      4380
atcaagctct gatcaagaga caggatgagg atcgtttcgc atgattgaac aagatggatt      4440
gcacgcaggt tctccggccg cttgggtgga gaggctattc ggctatgact gggcacaaca      4500
gacaatcggc tgctctgatg ccgccgtgtt ccggctgtca gcgcaggggc gcccggttct      4560
ttttgtcaag accgacctgt ccggtgccct gaatgaactg caagacgagg cagcgcggct      4620
atcgtggctg gccacgacgg gcgttccttg cgcagctgtg ctcgacgttg tcactgaagc      4680
gggaagggac tggctgctat tgggcgaagt gccggggcag gatctcctgt catctcacct      4740
tgctcctgcc gagaaagtat ccatcatggc tgatgcaatg cggcggctgc atacgcttga      4800
tccggctacc tgcccattcg accaccaagc gaaacatcgc atcgagcgag cacgtactcg      4860
gatggaagcc ggtcttgtcg atcaggatga tctggacgaa gagcatcagg gctcgcgcc       4920 agccgaactg ttcgccaggc tcaaggcgag catgcccgac ggcgaggatc tcgtcgtgac      4980
ccatggcgat gcctgcttgc cgaatatcat ggtggaaaat ggccgctttt ctggattcat      5040
cgactgtggc cggctgggtg tggcggaccg ctatcaggac atagcgttgg ctacccgtga      5100
tattgctgaa gagcttggcg gcgaatgggc tgaccgcttc ctcgtgcttt acggtatcgc      5160
cgctcccgat tcgcagcgca tcgccttcta tcgccttctt gacgagttct tctgaattat      5220
taacgcttac aatttcctga tgcggtattt tctccttacg catctgtgcg gtatttcaca      5280
ccgcatacag gtggcacttt tcggggaaat gtgcgcggaa cccctatttg tttattttc      5340 taaatacatt caaatatgta tccgctcatg agacaataac cctgataaat gcttcaataa      5400
tagcacgtgc taaaacttca ttttaatt aaaaggatct aggtgaagat cctttttgat       5460
aatctcatga ccaaaatccc ttaacgtgag ttttcgttcc actgagcgtc agaccccgta      5520
gaaaagatca aaggatcttc ttgagatcct ttttttctgc gcgtaatctg ctgcttgcaa      5580
acaaaaaaac caccgctacc agcggtggtt tgtttgccgg atcaagagct accaactctt      5640
tttccgaagg taactggctt cagcagagcg cagataccaa atactgtcct tctagtgtag      5700
ccgtagttag gccaccactt caagaactct gtagcaccgc ctacatacct cgctctgcta      5760
atcctgttac cagtggctgc tgccagtggc gataagtcgt gtcttaccgg gttggactca      5820
agacgatagt taccggataa ggcgcagcgg tcgggctgaa cggggggttc gtgcacacag      5880
cccagcttgg agcgaacgac ctacaccgaa ctgagatacc tacagcgtga gctatgagaa      5940
agcgccacgc ttcccgaagg gagaaaggcg gacaggtatc cggtaagcgg cagggtcgga      6000
acaggagagc gcacgaggga gcttccaggg ggaaacgcct ggtatcttta tagtcctgtc      6060
gggtttcgcc acctctgact tgagcgtcga ttttgtgat gctcgtcagg ggggcggagc       6120
ctatggaaaa acgccagcaa cgcggccttt ttacggttcc tgggcttttg ctggcctttt      6180
gctcacatgt tctt                                                        6194
```

<210> SEQ ID NO 28
<211> LENGTH: 4354
<212> TYPE: DNA
<213> ORGANISM: Artificial Sequence
<220> FEATURE:
<223> OTHER INFORMATION: Synthetic
<220> FEATURE:
<223> OTHER INFORMATION: pVAX1 A120 ZFN 3 LEFT

<400> SEQUENCE: 28

```
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccactag tccagtgtgg tggaattaat cgcctagag atctggcggc     780
ggagagggca gaggaagtct tctaacctgc ggtgacgtgg aggagaatcc cggccctagg     840
accatggact acaaagacca tgacggtgat tataaagatc atgacatcga ttacaaggat     900
gacgatgaca gatgccccc caagaagaag aggaaggtcg gcattcatgg ggtacccgcc     960
gctatggctg agaggccctt ccagtgtcga atctgcatgc gtaacttcag tgaccagtcc    1020
aacctgcgcg cccacatccg cacccacacc ggcgagaagc cttttgcctg tgacatttgt    1080
gggaggaaat ttgcccgcaa gtccgaccgc atcaagcata ccaagataca cacgggcagc    1140
caaaagccct tccagtgtcg aatctgcatg cgtaagtttg cccgctccga caacctgtcc    1200
gtgcatacca gatacacac gggcgagaag cccttccagt gtcgaatctg catgcgtaac    1260
ttcagtgagc gcggcaccct ggcccgccac atccgcaccc acaccggcga agccttt     1320
gcctgtgaca tttgtgggag gaaatttgcc cgctccgacg ccctgaccca gcataccaag    1380
atacacctgc gggatcccca gctggtgaag agcgagctgg aggagaagaa gtccgagctg    1440
cggcacaagc tgaagtacgt gccccacgag tacatcgagc tgatcgagat cgccaggaac    1500
agcacccagg accgcatcct ggagatgaag gtgatggagt tcttcatgaa ggtgtacggc    1560
tacaggggaa agcaccctgg gcggaagcaga aagcctgacg cgccatcta cagtgggc    1620
agccccatcg attacggcgt gatcgtggac acaaaggcct acagcggcgg ctacaatctg    1680
cctatcggcc aggccgacga gatgcagaga tacgtgaagg agaaccagac ccggaataag    1740
cacatcaacc ccaacgagtg gtggaaggtg taccctagca gcgtgaccga gttcaagttc    1800
ctgttcgtga gcggccactt caagggcaac tacaaggccc agctgaccag gctgaaccgc    1860
aaaaccaact gcaatggcgc cgtgctgagc gtggaggagc tgctgatcgg cggcgagatg    1920
atcaaagccg gcaccctgac actggaggag gtgcggcgca agttcaacaa cggcgagatc    1980
```

```
aacttctgat aactcgagtc tagaattctg cagaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaagcggccg ctcgagtcta gagggcccgt    2160
ttaaacccgc tgatcagcct cgactgtgcc ttctagttgc cagccatctg ttgtttgccc    2220
ctcccccgtg ccttccttga ccctggaagg tgccactccc actgtccttt cctaataaaa    2280
tgaggaaatt gcatcgcatt gtctgagtag gtgtcattct attctggggg gtggggtggg    2340
gcaggacagc aagggggagg attgggaaga caatagcagg catgctgggg atgcggtggg    2400
ctctatggct tctactgggc ggttttatgg acagcaagcg aaccggaatt gccagctggg    2460
gcgccctctg gtaaggttgg aagccctgc aaagtaaact ggatggcttt ctcgccgcca    2520
aggatctgat ggcgcagggg atcaagctct gatcaagaga caggatgagg atcgtttcgc    2580
atgattgaac aagatggatt gcacgcaggt tctccggccg cttgggtgga gaggctattc    2640
ggctatgact gggcacaaca gacaatcggc tgctctgatg ccgccgtgtt ccggctgtca    2700
gcgcaggggc gcccggttct ttttgtcaag accgacctgt ccggtgccct gaatgaactg    2760
caagacgagg cagcgcggct atcgtggctg gccacgacgg gcgttccttg cgcagctgtg    2820
ctcgacgttg tcactgaagc gggaagggac tggctgctat tgggcgaagt gccggggcag    2880
gatctcctgt catctcacct tgctcctgcc gagaaagtat ccatcatggc tgatgcaatg    2940
cggcggctgc atacgcttga tccggctacc tgcccattcg accaccaagc gaaacatcgc    3000
atcgagcgag cacgtactcg gatggaagcc ggtcttgtcg atcaggatga tctggacgaa    3060
gagcatcagg ggctcgcgcc agccgaactg ttcgccaggc tcaaggcgag catgcccgac    3120
ggcgaggatc tcgtcgtgac ccatggcgat gcctgcttgc cgaatatcat ggtggaaaat    3180
ggccgctttt ctggattcat cgactgtggc cggctgggtg tggcggaccg ctatcaggac    3240
atagcgttgg ctacccgtga tattgctgaa gagcttggcg gcgaatgggc tgaccgcttc    3300
ctcgtgcttt acggtatcgc cgctcccgat tcgcagcgca tcgccttcta tcgccttctt    3360
gacgagttct tctgaattat taacgcttac aatttcctga tgcggtattt tctccttacg    3420
catctgtgcg gtatttcaca ccgcatacag gtggcacttt tcggggaaat gtgcgcggaa    3480
cccctatttg tttatttttc taaatacatt caaatatgta tccgctcatg agacaataac    3540
cctgataaat gcttcaataa tagcacgtgc taaaacttca ttttaatttt aaaaggatct    3600
aggtgaagat cctttttgat aatctcatga ccaaaatccc ttaacgtgag ttttcgttcc    3660
actgagcgtc agaccccgta gaaaagatca aaggatcttc ttgagatcct ttttttctgc    3720
gcgtaatctg ctgcttgcaa acaaaaaaac caccgctacc agcggtggtt tgtttgccgg    3780
atcaagagct accaactctt tttccgaagg taactggctt cagcagagcg cagataccaa    3840
atactgtcct tctagtgtag ccgtagttag gccaccactt caagaactct gtagcaccgc    3900
ctacatacct cgctctgcta atcctgttac cagtggctgc tgccagtggc gataagtcgt    3960
gtcttaccgg gttggactca agacgatagt taccggataa ggcgcagcgg tcgggctgaa    4020
cggggggttc gtgcacacag cccagcttgg agcgaacgac ctacaccgaa ctgagatacc    4080
tacagcgtga gctatgagaa agcgccacgc ttcccgaagg gagaaaggcg gacaggtatc    4140
cggtaagcgg cagggtcgga acaggagagc gcacgaggga gcttccaggg ggaaacgcct    4200
ggtatcttta tagtcctgtc gggtttcgcc acctctgact tgagcgtcga ttttgtgat     4260 gctcgtcagg gggcggagc ctatggaaaa acgccagcaa cgcggccttt ttacggttcc     4320
tgggcttttg ctggcctttt gctcacatgt tctt                                4354
```

<210> SEQ ID NO 29
<211> LENGTH: 4393
<212> TYPE: DNA
<213> ORGANISM: Artificial Sequence
<220> FEATURE:
<223> OTHER INFORMATION: Synthetic
<220> FEATURE:
<223> OTHER INFORMATION: pVAX1 A120 ZFN 3 RIGHT

<400> SEQUENCE: 29

```
gactcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
ctatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccactag tccagtgtgg tggaattaat tcgccatgga ctacaaagac     780
catgacggtg attataaaga tcatgacatc gattacaagg atgacgatga caagatggcc     840
cccaagaaga agaggaaggt cggcatccac ggggtacccg ccgctatggc tgagaggccc     900
ttccagtgtc gaatctgcat gcgtaacttc agtcagtcct ccgacctgtc cgcccacatc     960
cgcacccaca ccggcgagaa gccttttgcc tgtgacattt gtgggaggaa atttgcctgg    1020
cgctcctccc tgcgccagca taccaagata cacacgcatc caggacacc tattcccaag    1080
cccttccagt gtcgaatctg catgcgtaac ttcagtcagt ccggcgacct gacccgccac    1140
atccgcaccc acaccggcga aagcctttt gcctgtgaca tttgtgggag gaaatttgcc    1200
cgccgcgccg accgcgccaa gcataccaag atacacacgc acccgcgcgc ccgatcccg    1260
aagcccttcc agtgtcgaat ctgcatgcgt aacttcagtc gctccgacga cctgacccgc    1320
cacatccgca cccacaccgg cgagaagcct tttgcctgtg acatttgtgg gaggaaattt    1380
gcccagcgct ccaccctgtc ctcccatacc aagatacacc tgcgggatc ccagctggtg    1440
aagagcgagc tggaggagaa gaagtccgag ctgcggcaca gctgaagta cgtgccccac    1500
gagtacatcg agctgatcga gatcgccagg aacagcaccc aggaccgcat cctggagatg    1560
aaggtgatgg agttcttcat gaaggtgtac ggctacaggg gaaagcacct gggcggaagc    1620
agaaagcctg acggcgccat ctatacagtg ggcagcccca tcgattacgg cgtgatcgtg    1680
gacacaaagg cctacagcgg cggctacaat ctgcctatcg ccaggcgga cgagatggag    1740
agatacgtgg aggagaacca gacccgggat aagcacctca ccccaacga gtggtggaag    1800
gtgtacccta gcagcgtgac cgagttcaag ttcctgttcg tgagcggcca cttcaagggc    1860
aactacaagg cccagctgac caggctgaac cacatcacca actgcaatgg cgccgtgctg    1920
agcgtggagg agctgctgat cggcggcgag atgatcaaag ccggcaccct gacactggag    1980
```

```
gaggtgcggc gcaagttcaa caacggcgag atcaacttca gatcttgata actcgagtct    2040
agaattctgc agaaaaaaaa aaaaaaaaaa aaaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa aagcggccgc tcgagtctag agggcccgtt taaacccgct gatcagcctc    2220
gactgtgcct tctagttgcc agccatctgt tgtttgcccc tccccgtgcc ttccttgac     2280 cctggaaggt gccactccca ctgtcctttc ctaataaaat gaggaaattg catcgcattg    2340
tctgagtagg tgtcattcta ttctgggggg tggggtgggg caggacagca agggggagga    2400
ttgggaagac aatagcaggc atgctgggga tgcggtgggc tctatggctt ctactgggcg    2460
gttttatgga cagcaagcga accggaattg ccagctgggg cgccctctgg taaggttggg    2520
aagccctgca aagtaaactg gatggctttc tcgccgccaa ggatctgatg gcgcagggga    2580
tcaagctctg atcaagagac aggatgagga tcgtttcgca tgattgaaca gatggattg     2640 cacgcaggtt ctccggccgc ttgggtggag aggctattcg gctatgactg gcacaacag     2700 acaatcggct gctctgatgc cgccgtgttc cggctgtcag cgcaggggcg cccggttctt    2760
tttgtcaaga ccgacctgtc cggtgccctg aatgaactgc aagacgaggc agcgcggcta    2820
tcgtggctgg ccacgacggg cgttccttgc gcagctgtgc tcgacgttgt cactgaagcg    2880
ggaagggact ggctgctatt gggcgaagtg ccggggcagg atctcctgtc atctcacctt    2940
gctcctgccg agaaagtatc catcatggct gatgcaatgc ggcggctgca tacgcttgat    3000
ccggctacct gcccattcga ccaccaagcg aaacatcgca tcgagcgagc acgtactcgg    3060
atggaagccg tcttgtcga tcaggatgat ctggacgaag agcatcaggg gctcgcgcca    3120
gccgaactgt tcgccaggct caaggcgagc atgcccgacg gcgaggatct cgtcgtgacc    3180
catggcgatg cctgcttgcc gaatatcatg gtggaaaatg gccgcttttc tggattcatc    3240
gactgtggcc ggctgggtgt ggcggaccgc tatcaggaca tagcgttggc tacccgtgat    3300
attgctgaag agcttggcgg cgaatgggct gaccgcttcc tcgtgcttta cggtatcgcc    3360
gctcccgatt cgcagcgcat cgccttctat cgccttcttg acgagttctt ctgaattatt    3420
aacgcttaca atttcctgat gcggtatttt ctccttacgc atctgtgcgg tatttcacac    3480
cgcatacagg tggcactttt cggggaaatg tgcgcggaac ccctatttgt ttatttttct    3540
aaatacattc aaatatgtat ccgctcatga caataaacc ctgataaatg cttcaataat     3600
agcacgtgct aaaacttcat ttttaattta aaaggatcta ggtgaagatc cttttttgata   3660 atctcatgac caaaatccct taacgtgagt tttcgttcca ctgagcgtca gaccccgtag    3720
aaaagatcaa aggatcttct tgagatcctt ttttttctgcg cgtaatctgc tgcttgcaaa    3780
caaaaaaacc accgctacca gcggtggttt gtttgccgga tcaagagcta ccaactcttt    3840
ttccgaaggt aactggcttc agcagagcgc agataccaaa tactgtcctt ctagtgtagc    3900
cgtagttagg ccaccacttc aagaactctg tagcaccgcc tacatacctc gctctgctaa    3960
tcctgttacc agtggctgct gccagtggcg ataagtcgtg tcttaccggg ttggactcaa    4020
gacgatagtt accggataag gcgcagcggt cgggctgaac ggggggttcg tgcacacagc    4080
ccagcttgga gcgaacgacc tacaccgaac tgagatacct acagcgtgag ctatgagaaa    4140
gcgccacgct tcccgaaggg agaaaggcgg acaggtatcc ggtaagcggc agggtcggaa    4200
caggagagcg cacgagggag cttccagggg gaaacgcctg gtatctttat agtcctgtcg    4260
ggtttcgcca cctctgactt gagcgtcgat ttttgtgatg ctcgtcaggg ggcggagcc     4320 tatggaaaaa cgccagcaac gcggcctttt tacggttcct ggccttttgc tggccttttg    4380
```

```
ctcacatgtt ctt                                                      4393

<210> SEQ ID NO 30
<211> LENGTH: 4541
<212> TYPE: DNA
<213> ORGANISM: Artificial Sequence
<220> FEATURE:
<223> OTHER INFORMATION: Synthetic
<220> FEATURE:
<223> OTHER INFORMATION: pVAX1 A120 Foxp3 (for mock mRNA)

<400> SEQUENCE: 30
gactcttcgc gatgtacggg ccagatatac gcgttgacat tgattattga ctagttatta    60
atagtaatca attacggggt cattagttca tagcccatat atggagttcc gcgttacata   120
acttacggta atggcccgc ctggctgacc gcccaacgac ccccgcccat tgacgtcaat    180
aatgacgtat gttcccatag taacgccaat agggactttc cattgacgtc aatgggtgga   240
ctatttacgg taaactgccc acttggcagt acatcaagtg tatcatatgc caagtacgcc   300
ccctattgac gtcaatgacg gtaaatggcc cgcctggcat tatgcccagt acatgacctt   360
atgggacttt cctacttggc agtacatcta cgtattagtc atcgctatta ccatggtgat   420
gcggttttgg cagtacatca atgggcgtgg atagcggttt gactcacggg gatttccaag   480
tctccacccc attgacgtca atgggagttt gttttggcac caaaatcaac gggactttcc   540
aaaatgtcgt aacaactccg ccccattgac gcaaatgggc ggtaggcgtg tacggtggga   600
ggtctatata agcagagctc tctggctaac tagagaaccc actgcttact ggcttatcga   660
aattaatacg actcactata gggagaccca agctggctag cgtttaaact taagcttggt   720
acctcagacg agacttggaa gacagtcaca tctcagcagc tcctctgccg ttatccagcc   780
tgcctctgac aagaacccaa tgcccaaccc taggccagcc aagcctatgg ctccttcctt   840
ggcccttggc ccatcccag gagtcttgcc aagctggaag actgcaccca gggctcaga    900 acttctaggg accaggggct ctggggacc cttccaaggt cgggacctgc gaagtggggc   960
ccacacctct tcttccttga accccctgcc accatcccag ctgcagctgc ctacagtgcc  1020
cctagtcatg gtggcaccgt ctggggcccg actaggtccc tcaccccacc tacaggcccct  1080 tctccaggac agaccacact tcatgcatca gctctccact gtggatgccc atgcccagac  1140
ccctgtgctc caagtgcgtc cactggacaa cccagccatg atcagcctcc caccaccttc  1200
tgctgccact ggggtcttct ccctcaaggc ccggcctggc ctgccacctg ggatcaatgt  1260
ggccagtctg gaatgggtgt ccaggagcc agctctactc tgcaccttcc cacgctcggg  1320
tacacccagg aaagacagca acctttttgc tgcaccccaa ggatcctacc cactgctggc  1380
aaatggagtc tgcaagtggc ctggttgtga aaggtcttc gaggagccag aagagtttct  1440
caagcactgc caagcagatc atctcctgga tgagaaaggc aaggcccagt gcctcctcca  1500
gagagaagtg gtgcagtctc tggagcagca gctggagctg gaaaaggaga gctgggagc   1560 tatgcaggcc cacctggctg gaagatggc gctggccaag gctccatctg tggcctcaat   1620
ggacaagagc tcttgctgca tcgtagccac cagtactcag ggcagtgtgc tcccggcctg   1680
gtctgctcct cgggaggctc cagacggcgg cctgtttgca gtgcggaggc acctctgggg   1740
aagccatggc aatagttcct tcccagagtt cttccacaac atggactact tcaagtacca   1800
caatatgcga ccccctttca cctatgccac ccttatccga tgggccatcc tggaagcccc   1860
ggagaggcag aggacactca atgaaatcta ccattggttt actcgcatgt tcgcctactt   1920
```

```
cagaaaccac cccgccacct ggaagaatgc catccgccac aacctgagcc tgcacaagtg    1980
ctttgtgcga gtggagagcg agaagggagc agtgtggacc gtagatgaat ttgagtttcg    2040
caagaagagg agccaacgcc ccaacaagtg ctccaatccc tgcccttgac ctcaaaacca    2100
agaaaaggtg ggcggggggag ggggccaaaa ccatgagact gaggctgtgg gggcaaggag    2160
gcaagtccta cgtgtaccta tggaaaccgg aattctgcag aaaaaaaaaa aaaaaaaaa    2220 aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa gcggccgctc gagtctagag    2340
ggcccgttta aacccgctga tcagcctcga ctgtgccttc tagttgccag ccatctgttg    2400 tttgccccte ccccgtgcct tccttgaccc tggaaggtgc cactcccact gtcctttcct    2460
aataaaatga ggaaattgca tcgcattgtc tgagtaggtg tcattctatt ctggggggtg    2520
gggtggggca ggacagcaag ggggaggatt gggaagacaa tagcaggcat gctgggatg    2580 cggtgggctc tatggcttct actgggcggt tttatggaca gcaagcgaac cggaattgcc    2640
agctggggcg ccctctggta aggttgggaa gccctgcaaa gtaaactgga tggctttctc    2700
gccgccaagg atctgatggc caggggatc aagctctgat caagagacag gatgaggatc    2760
gtttcgcatg attgaacaag atggattgca cgcaggttct ccggccgctt gggtggagag    2820
gctattcggc tatgactggg cacaacagac aatcggctgc tctgatgccg ccgtgttccg    2880
gctgtcagcg caggggcgcc cggttctttt tgtcaagacc gacctgtccg gtgccctgaa    2940
tgaactgcaa gacgaggcag cgcggctatc gtggctggcc acgacgggcg ttccttgcgc    3000
agctgtgctc gacgttgtca ctgaagcggg aagggactgg ctgctattgg gcgaagtgcc    3060
ggggcaggat ctcctgtcat ctcaccttgc tcctgccgag aaagtatcca tcatggctga    3120
tgcaatgcgg cggctgcata cgcttgatcc ggctacctgc ccattcgacc accaagcgaa    3180
acatcgcatc gagcgagcac gtactcggat ggaagccggt cttgtcgatc aggatgatct    3240
ggacgaagag catcagggc tcgcgccagc cgaactgttc gccaggctca aggcgagcat    3300
gcccgacggc gaggatctcg tcgtgaccca tggcgatgcc tgcttgccga atatcatggt    3360
ggaaaatggc cgcttttctg gattcatcga ctgtggccgg ctgggtgtgg cggaccgcta    3420
tcaggacata gcgttggcta cccgtgatat tgctgaagag cttggcggcg aatgggctga    3480
ccgcttcctc gtgctttacg gtatcgccgc tcccgattcg cagcgcatcg ccttctatcg    3540
ccttcttgac gagttcttct gaattattaa cgcttacaat ttcctgatgc ggtattttct    3600
ccttacgcat ctgtgcggta tttcacaccg catacaggtg gcacttttcg gggaaatgtg    3660
cgcggaaccc ctatttgttt attttcctaa atacattcaa atatgtatcc gctcatgaga    3720
caataaccct gataaatgct tcaataatag cacgtgctaa aacttcattt ttaatttaaa    3780
aggatctagg tgaagatcct ttttgataat ctcatgacca aaatccctta acgtgagttt    3840
tcgttccact gagcgtcaga ccccgtagaa aagatcaaag gatcttcttg agatcctttt    3900
tttctgcgcg taatctgctg cttgcaaaca aaaaaaccac cgctaccagc ggtggtttgt    3960
ttgccggatc aagagctacc aactcttttt ccgaaggtaa ctggcttcag cagagcgcag    4020
ataccaaata ctgtccttct agtgtagccg tagttaggcc accacttcaa gaactctgta    4080
gcaccgccta catacctcgc tctgctaatc ctgttaccag tggctgctgc cagtggcgat    4140
aagtcgtgtc ttaccgggtt ggactcaaga cgatagttac cggataaggc gcagcggtcg    4200
ggctgaacgg ggggttcgtg cacacagccc agcttggagc gaacgaccta caccgaactg    4260
agatacctac agcgtgagct atgagaaagc gccacgcttc ccgaagggag aaaggcggac    4320
```

| | | |
|---|---|---|
| aggtatccgg taagcggcag ggtcggaaca ggagagcgca cgaggagct tccagggga | | 4380 |
| aacgcctggt atctttatag tcctgtcggg tttcgccacc tctgacttga gcgtcgattt | | 4440 |
| ttgtgatgct cgtcaggggg gcggagccta tggaaaaacg ccagcaacgc ggcctttta | | 4500 |
| cggttcctgg gcttttgctg gccttttgct cacatgttct t | | 4541 |

<210> SEQ ID NO 31
<211> LENGTH: 6612
<212> TYPE: DNA
<213> ORGANISM: Artificial Sequence
<220> FEATURE:
<223> OTHER INFORMATION: Synthetic
<220> FEATURE:
<223> OTHER INFORMATION: AAV6_CB7_Cl-Foxp3 (mock-control)

<400> SEQUENCE: 31

| | | |
|---|---|---|
| gctgcgcgct cgctcgctca ctgaggccgc ccgggcaaag cccgggcgtc gggcgacctt | | 60 |
| tggtcgcccg gcctcagtga gcgagcgagc gcgcagagag ggagtggcca actccatcac | | 120 |
| taggggttcc ttgtagttaa tgattaaccc gccatgctac ttatctacca gggtaatggg | | 180 |
| gatcctctag aactatagct agtcgacatt gattattgac tagttattaa tagtaatcaa | | 240 |
| ttacggggtc attagttcat agcccatata tggagttccg cgttacataa cttacggtaa | | 300 |
| atggcccgcc tggctgaccg cccaacgacc cccgcccatt gacgtcaata atgacgtatg | | 360 |
| ttcccatagt aacgccaata gggactttcc attgacgtca atgggtggac tatttacggt | | 420 |
| aaactgccca cttggcagta catcaagtgt atcatatgcc aagtacgccc cctattgacg | | 480 |
| tcaatgacgg taaatggccc gcctggcatt atgcccagta catgacctta tgggactttc | | 540 |
| ctacttggca gtacatctac gtattagtca tcgctattac catggtcgag gtgagcccca | | 600 |
| cgttctgctt cactctcccc atctcccccc cctccccacc cccaattttg tatttattta | | 660 |
| ttttttaatt attttgtgca gcgatggggg cggggggggg ggggggcgc gcgccaggcg | | 720 |
| gggcggggcg gggcgagggg cggggcgggg cgaggcggag aggtgcggcg gcagccaatc | | 780 |
| agagcggcgc gctccgaaag tttccttta tggcgaggcg gcggcggcgg cggccctata | | 840 |
| aaaagcgaag cgcgcggcgg gcgggagtc gctgcgacgc tgccttcgcc ccgtgccccg | | 900 |
| ctccgccgcc gcctcgcgcc gcccgccccg gctctgactg accgcgttac tcccacaggt | | 960 |
| gagcgggcgg gacggccctt ctcctccggg ctgtaattag cgcttggttt aatgacggct | | 1020 |
| tgtttctttt ctgtggctgc gtgaaagcct tgaggggctc cgggagggcc ctttgtgcgg | | 1080 |
| ggggagcggc tcgggggtg cgtgcgtgtg tgtgtgcgtg gggagcgccg cgtgcggctc | | 1140 |
| cgcgctgccc ggcggctgtg agcgctgcgg gcgcggcgcg gggctttgtg cgctccgcag | | 1200 |
| tgtgcgcgag gggagcgcgg ccggggcgg tgccccgcgg tgcgggggg gctgcgaggg | | 1260 |
| gaacaaaggc tgcgtgcggg gtgtgtgcgt ggggggggtga gcaggggtg tgggcgcgtc | | 1320 |
| ggtcgggctg caaccccccc tgcaccccc tcccgagtt gctgagcacg gcccggcttc | | 1380 |
| gggtgcgggg ctccgtacgg ggcgtggcgc ggggctcgcc gtgccgggcg gggggtggcg | | 1440 |
| gcaggtgggg gtgccgggcg gggcggggcc gcctcgggcc gggagggct cggggagggg | | 1500 |
| gcgcggcggc cccggagcg ccggcggctg tcgaggcgcg cgagccgca gccattgcct | | 1560 |
| tttatggtaa tcgtgcgaga gggcgcaggg acttcctttg tcccaaatct gtgcggagcc | | 1620 |
| gaaatctggg aggcgccgcc gcaccccctc tagcggcgc ggggcgaagc ggtgcggcgc | | 1680 |
| cggcaggaag gaaatgggcg gggagggcct tcgtgcgtcg ccgcgccgcc gtccccttct | | 1740 |

```
ccctctccag cctcggggct gtccgcgggg ggacggctgc cttcgggggg gacgggcag    1800
ggcggggttc ggcttctggc gtgtgaccgg cggctctaga gcctctgcta accatgttca   1860
tgccttcttc ttttcctac  agctcctggg caacgtgctg gttattgtgc tgtctcatca   1920
ttttggcaaa gaattcacgc gtggtacctc agacgagact tggaagacag tcacatctca   1980
gcagctcctc tgccgttatc cagcctgcct ctgacaagaa cccaatgccc aaccctaggc   2040
cagccaagcc tatggctcct ccttggccc  ttggcccatc cccaggagtc ttgccaagct   2100
ggaagactgc acccaagggc tcagaacttc tagggaccag gggctctggg ggacccttcc   2160
aaggtcggga cctgcgaagt ggggcccaca cctcttcttc cttgaacccc ctgccaccat   2220
cccagctgca gctgcctaca gtgccctag  tcatggtggc accgtctggg gcccgactag   2280
gtccctcacc ccacctacag gcccttctcc aggacagacc acacttcatg catcagctct   2340
ccactgtgga tgcccatgcc cagaccctg  tgctccaagt gcgtccactg gacaacccag   2400
ccatgatcag cctcccacca ccttctgctg ccactggggt cttctccctc aaggcccggc   2460
ctggcctgcc acctgggatc aatgtggcca gtctggaatg ggtgtccagg gagccagctc   2520
tactctgcac cttcccacgc tcgggtacac ccaggaaaga cagcaacctt ttggctgcac   2580
cccaaggatc ctacccactg ctggcaaatg gagtctgcaa gtggcctggt tgtgagaagg   2640
tcttcgagga gccagaagag tttctcaagc actgccaagc agatcatctc ctggatgaga   2700
aaggcaaggc ccagtgcctc ctccagagag aagtggtgca gtctctggag cagcagctgg   2760
agctggaaaa ggagaagctg ggagctatgc aggcccacct ggctgggaag atggcgctgg   2820
ccaaggctcc atctgtggcc tcaatggaca agagctcttg ctgcatcgta gccaccagta   2880
ctcagggcag tgtgctcccg gcctggtctg ctcctcggga ggctccagac ggcggcctgt   2940
ttgcagtgcg gaggcacctc tggggaagcc atggcaatag ttccttccca gagttcttcc   3000
acaacatgga ctacttcaag taccacaata tgcgaccccc tttcacctat gccacccta   3060
tccgatgggc catcctggaa gccccggaga ggcagaggac actcaatgaa atctaccatt   3120
ggtttactcg catgttcgcc tacttcagaa accaccccgc cacctggaag aatgccatcc   3180
gccacaacct gagcctgcac aagtgctttg tgcgagtgga gagcgagaag ggagcagtgt   3240
ggaccgtaga tgaatttgag tttcgcaaga agaggagcca acgcccaac  aagtgctcca   3300
atccctgccc ttgacctcaa aaccaagaaa aggtgggcgg gggaggggc  caaaaccatg   3360
agactgaggc tgtgggggca aggaggcaag tcctacgtgt acctatggaa accgctcgag   3420
gacggggtga actacgcctg aggatccgat ctttttccct ctgccaaaaa ttatggggac   3480
atcatgaagc cccttgagca tctgacttct ggctaataaa ggaaatttat tttcattgca   3540
atagtgtgtt ggaattttt  gtgtctctca ctcggaagca attcgttgat ctgaatttcg   3600
accacccata tacccatta  ccctggtaga taagtagcat ggcgggttaa tcattaacta   3660
caaggaaccc ctagtgatgg agttggccac tccctctctg cgcgctcgct cgctcactga   3720
ggccgggcga ccaaaggtcg cccgacgccc gggctttgcc cggcggcct  cagtgagcga   3780
gcgagcgcgc agccttaatt aacctaattc actggccgtc gttttacaac gtcgtgactg   3840
ggaaaaccct ggcgttaccc aacttaatcg ccttgcagca catcccccctt tcgccagctg   3900
gcgtaatagc gaagaggccc gcaccgatcg cccttcccaa cagttgcgca gcctgaatgg   3960
cgaatgggac gcgccctgta gcggcgcatt aagcgcggcg ggtgtggtgg ttacgcgcag   4020
cgtgaccgct acacttgcca gcgccctagc gcccgctcct ttcgctttct tcccttcctt   4080
tctcgccacg ttcgccggct ttccccgtca agctctaaat cggggctcc  ctttagggtt   4140
```

-continued

```
ccgatttagt gctttacggc acctcgaccc caaaaaactt gattagggtg atggttcacg    4200
tagtgggcca tcgccctgat agacggtttt tcgccctttg acgttggagt ccacgttctt    4260
taatagtgga ctcttgttcc aaactggaac aacactcaac cctatctcgg tctattcttt    4320
tgatttataa gggattttgc cgatttcggc ctattggtta aaaaatgagc tgatttaaca    4380
aaaatttaac gcgaatttta acaaaatatt aacgcttaca atttaggtgg cacttttcgg    4440
ggaaatgtgc gcggaacccc tatttgttta tttttctaaa tacattcaaa tatgtatccg    4500
ctcatgagac aataaccctg ataaatgctt caataatatt gaaaaggaa gagtatgagt     4560 attcaacatt tccgtgtcgc ccttattccc ttttttgcgg catttttgcct tcctgttttt   4620 gctcacccag aaacgctggt gaaagtaaaa gatgctgaag atcagttggg tgcacgagtg    4680
ggttacatcg aactggatct caacagcggt aagatccttg agagttttcg ccccgaagaa    4740
cgttttccaa tgatgagcac ttttaaagtt ctgctatgtg gcgcggtatt atcccgtatt    4800
gacgccgggc aagagcaact cggtcgccgc atacactatt ctcagaatga cttggttgag    4860
tactcaccag tcacagaaaa gcatcttacg gatggcatga cagtaagaga attatgcagt    4920
gctgccataa ccatgagtga taacactgcg gccaacttac ttctgacaac gatcggagga    4980
ccgaaggagc taaccgcttt tttgcacaac atgggggatc atgtaactcg ccttgatcgt    5040
tgggaaccgg agctgaatga agccatacca aacgacgagc gtgacaccac gatgcctgta    5100
gcaatggcaa caacgttgcg caaactatta actggcgaac tacttactct agcttcccgg    5160
caacaattaa tagactggat ggaggcggat aaagttgcag gaccacttct gcgctcggcc    5220
cttccggctg gctggtttat tgctgataaa tctggagccg gtgagcgtgg gtctcgcggt    5280
atcattgcag cactggggcc agatggtaag ccctcccgta tcgtagttat ctacacgacg    5340
gggagtcagg caactatgga tgaacgaaat agacagatcg ctgagatagg tgcctcactg    5400
attaagcatt ggtaactgtc agaccaagtt tactcatata ctttagat tgatttaaaa     5460 cttcattttt aatttaaaag gatctaggtg aagatccttt ttgataatct catgaccaaa    5520
atcccttaac gtgagttttc gttccactga gcgtcagacc ccgtagaaaa gatcaaagga    5580
tcttcttgag atcctttttt tctgcgcgta atctgctgct tgcaaacaaa aaaaccaccg    5640
ctaccagcgg tggtttgttt gccggatcaa gagctaccaa ctcttttttcc gaaggtaact    5700 ggcttcagca gagcgcagat accaaatact gttcttctag tgtagccgta gttaggccac    5760
cacttcaaga actctgtagc accgcctaca tacctcgctc tgctaatcct gttaccagtg    5820
gctgctgcca gtggcgataa gtcgtgtctt accgggttgg actcaagacg atagttaccg    5880
gataaggcgc agcggtcggg ctgaacgggg ggttcgtgca cacagcccag cttggagcga    5940
acgacctaca ccgaactgag atacctacag cgtgagctat gagaaagcgc cacgcttccc    6000
gaagggagaa aggcggacag gtatccggta agcggcaggg tcggaacagg agagcgcacg    6060
agggagcttc cagggggaaa cgcctggtat ctttatagtc ctgtcgggtt tcgccacctc    6120
tgacttgagc gtcgattttt gtgatgctcg tcagggggc ggagcctatg gaaaaacgcc    6180
agcaacgcgg cctttttacg gttcctggcc ttttgctggc cttttgctca catgttcttt    6240
cctgcgttat cccctgattc tgtggataac cgtattaccg cctttgagtg agctgatacc    6300
gctcgccgca gccgaacgac cgagcgcagc gagtcagtga gcgaggaagc ggaagagcgc    6360
ccaatacgca aaccgcctct ccccgcgcgt tggccgattc attaatgcag ctggcacgac    6420
aggtttcccg actggaaagc gggcagtgag cgcaacgcaa ttaatgtgag ttagctcact    6480
```

-continued

| | |
|---|---|
| cattaggcac cccaggcttt acactttatg cttccggctc gtatgttgtg tggaattgtg | 6540 |
| agcggataac aatttcacac aggaaacagc tatgaccatg attacgccag atttaattaa | 6600 |
| ggccttaatt ag | 6612 |

<210> SEQ ID NO 32
<211> LENGTH: 6898
<212> TYPE: DNA
<213> ORGANISM: Artificial Sequence
<220> FEATURE:
<223> OTHER INFORMATION: Synthetic
<220> FEATURE:
<223> OTHER INFORMATION: AAV6_CAG_SP-B_DONOR

<400> SEQUENCE: 32

| | |
|---|---|
| gacgcgccct gtagcggcgc attaagcgcg gcgggtgtgg tggttacgcg cagcgtgacc | 60 |
| gctacacttg ccagcgccct agcgcccgct cctttcgctt tcttcccttc ctttctcgcc | 120 |
| acgttcgccg gctttccccg tcaagctcta aatcggggggc tccctttagg gttccgattt | 180 |
| agtgctttac ggcacctcga cccaaaaaaa cttgattagg gtgatggttc acgtagtggg | 240 |
| ccatcgccct gatagacggt ttttcgccct ttgacgttgg agtccacgtt ctttaatagt | 300 |
| ggactcttgt tccaaactgg aacaacactc aaccctatct cggtctattc ttttgattta | 360 |
| taagggattt tgccgatttc ggcctattgg ttaaaaaatg agctgattta caaaaatttt | 420 |
| aacgcgaatt ttaacaaaat attaacgttt acaatttcag gtggcacttt tcggggaaat | 480 |
| gtgcgcggaa cccctatttg tttattttc taaatacatt caaatatgta tccgctcatg | 540 |
| agacaataac cctgataaat gcttcaataa tattgaaaaa ggaagagtat gagtattcaa | 600 |
| catttccgtg tcgcccttat tccctttttt gcggcatttt gccttcctgt ttttgctcac | 660 |
| ccagaaacgc tggtgaaagt aaaagatgct gaagatcagt tgggtgcacg agtgggttac | 720 |
| atcgaactgg atctcaacag cggtaagatc cttgagagtt ttcgccccga agaacgtttt | 780 |
| ccaatgatga gcacttttaa agttctgcta tgtggcgcgg tattatcccg tattgacgcc | 840 |
| gggcaagagc aactcggtcg ccgcatacac tattctcaga atgacttggt tgagtactca | 900 |
| ccagtcacag aaaagcatct tacggatggc atgacagtaa gagaattatg cagtgctgcc | 960 |
| ataaccatga gtgataacac tgcggccaac ttacttctga caacgatcgg aggaccgaag | 1020 |
| gagctaaccg cttttttgca caacatgggg gatcatgtaa ctcgccttga tcgttgggaa | 1080 |
| ccggagctga atgaagccat accaaacgac gagcgtgaca ccacgatgcc tgtagcaatg | 1140 |
| gcaacaacgt tgcgcaaact attaactggc gaactactta ctctagcttc ccggcaacaa | 1200 |
| ttaatagact ggatggaggc ggataaagtt gcaggaccac ttctgcgctc ggcccttccg | 1260 |
| gctggctggt ttattgctga taaatctgga gccggtgagc gtgggtctcg cggtatcatt | 1320 |
| gcagcactgg ggccagatgg taagccctcc cgtatcgtag ttatctacac gacggggagt | 1380 |
| caggcaacta tggatgaacg aaatagacag atcgctgaga taggtgcctc actgattaag | 1440 |
| cattggtaac tgtcagacca gtttactcat atatacttt agattgattt aaaacttcat | 1500 |
| ttttaattta aaaggatcta ggtgaagatc ctttttgata atctcatgac caaaatccct | 1560 |
| taacgtgagt tttcgttcca ctgagcgtca gaccccgtag aaaagatcaa aggatcttct | 1620 |
| tgagatcctt ttttttctgcg cgtaatctgc tgcttgcaaa caaaaaaacc accgctacca | 1680 |
| gcggtggttt gtttgccgga tcaagagcta ccaactcttt ttccgaaggt aactggcttc | 1740 |
| agcagagcgc agataccaaa tactgtcctt ctagtgtagc cgtagttagg ccaccacttc | 1800 |
| aagaactctg tagcaccgcc tacatacctc gctctgctaa tcctgttacc agtggctgct | 1860 |

```
gccagtggcg ataagtcgtg tcttaccggg ttggactcaa gacgatagtt accggataag    1920
gcgcagcggt cgggctgaac gggggggttcg tgcacacagc ccagcttgga gcgaacgacc   1980
tacaccgaac tgagataccct acagcgtgag cattgagaaa gcgccacgct tcccgaaggg   2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg ggcggagcc tatggaaaaa cgccagcaac     2220
gcggcctttt tacggttcct ggcctttttgc tggccttttg ctcacatgtt ctttcctgcg   2280
ttatcccctg attctgtgga taaccgtatt accgcctttg agtgagctga taccgctcgc    2340
cgcagccgaa cgaccgagcg cagcgagtca gtgagcgagg aagcggaaga gcgcctgatg    2400
cggtattttc tccttacgca tctgtgcggt atttcacacc gcagaccagc cgcgtaacct    2460
ggcaaaatcg gttacggttg agtaataaat ggatgccctg cgtaagcggg tgtgggcgga    2520
caataaagtc ttaaactgaa caaaatagat ctaaactatg acaataaagt cttaaactag    2580
acagaatagt tgtaaactga atcagtcca gttatgctgt gaaaaagcat actggactttt    2640 tgttatggct aaagcaaact cttcattttc tgaagtgcaa attgcccgtc gtattaaaga    2700
ggggcgtggc caagggcatg gtaaagacta tattcgcggc gttgtgacaa tttaccgaac    2760
aactccgcgg ccgggaagcc gatctcggct tgaacgaatt gttaggtggc ggtacttggg    2820
tcgatatcaa agtgcatcac ttcttcccgt atgcccaact ttgtatagag agccactgcg    2880
ggatcgtcac cgtaatctgc ttgcacgtag atcacataag caccaagcgc gttggcctca    2940
tgcttgagga gattgatgag cgcggtggca atgccctgcc tccggtgctc gccggagact    3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg gcgtaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
cacggatctg ccctggcttc aggagatcgg aagacctcgg ccgtcgcggc gcttgccggt    3780
ggtgctgacc ccggatgaag tggttcgcat cctcggtttt ctggaaggcg agcatcgttt    3840
gttcgcccag gactctagct atagttctag tggttggcta cattattgaa gcatttatca    3900
gggttattgt ctcagagcat gcctgcaggc agctgcgcgc tcgctcgctc actgaggccg    3960
cccgggcgtc gggcgacctt tggtcgcccg gcctcagtga gcgagcgagc gcgcagagag    4020
ggagtggcca actccatcac taggggttcc tgcggccgca cgcgtcgtct cacatgtggc    4080
gcgccaacat gtctcgagct gcgcgctcgc tcgctcactg aggccgcccg gcaaagccc    4140 gggcgtcggg cgacctttgg tcgcccggcc tcagtgagcg agcgagcgcg cagagaggga    4200
```

```
gtggccaact ccatcactag ggggttcctgt gatagagaaa agtgaaagtc gagctcggta    4260
cccgggtcga ggtaggcgtg tacggtggga ggcctatata agcagagctc gtttagtgaa    4320
ccgtcagatc gcctggagac gccatccacg ctgttttgac ctccatagaa gacaccggga    4380
ccgatccagc ctccgcggcc ccgaattctg cagatatcca gcacagtggc ggccgctagg    4440
gctagcggat cctctagaac tatagctagt cgacattgat tattgactag ttattaatag    4500
taatcaatta cggggtcatt agttcatagc ccatatatgg agttccgcgt tacataactt    4560
acggtaaatg gcccgcctgg ctgaccgccc aacgacccccc gcccattgac gtcaataatg    4620
acgtatgttc ccatagtaac gccaataggg actttccatt gacgtcaatg ggtggactat    4680
ttacggtaaa ctgcccactt ggcagtacat caagtgtatc atatgccaag tacgccccct    4740
attgacgtca atgacggtaa atggcccgcc tggcattatg cccagtacat gaccttatgg    4800
gactttccta cttggcagta catctacgta ttagtcatcg ctattaccat gtcgaggcca    4860
cgttctgctt cactctcccc atctcccccc cctccccacc cccaattttg tatttattta    4920
ttttttaatt attttgtgca gcgatggggg cggggggggg gggcgcgcgc caggcggggc    4980
ggggcggggc gaggggcggg gcggggcgag gcggagaggt gcggcggcag ccaatcagag    5040
cggcgcgctc cgaaagtttc cttttatggc gaggcggcgg cggcggcggc cctataaaaa    5100
gcgaagcgcg cggcgggcgg gagcaagctt tattgcggta gtttatcaca gttaaattgc    5160
taacgcagtc agtgcttctg acacaacagt ctcgaactta agctgcagaa gttggtcgtg    5220
aggcactggg caggtaagta tcaaggttac aagacaggtt taaggagacc aatagaaact    5280
gggcttgtcg agacagagaa gactcttgcg tttctgatag gcacctattg gtcttactga    5340
catccacttt gcctttctct ccacaggtgt ccactcccag ttcaattaca gctcttaagg    5400
ctagagtact aatacgact cactataggc tagcctcgag gccgccatgg ccaagtcgca    5460
cctactgcag tggctactgc tgcttcctac cctctgctgc ccaggtgcag ctatcacgtc    5520
ggcctcatcc ctggagtgtg cacaaggcc tcaattctgg tgccaaagcc tggagcatgc    5580
agtgcagtgc agagccctgg ggcactgcct gcaggaagtc tgggggcatg caggagctaa    5640
tgacctgtgc caagagtgtg aggatattgt ccacctcctc acaaagatga ccaaggaaga    5700
tgctttccag gaagcaatcc ggaagttcct ggaacaagaa tgtgatatcc ttcccttgaa    5760
gctgcttgtg ccccggtgtc gccaagtgct tgatgtctac ctgcccctgg ttattgacta    5820
cttccagagc cagattaacc ccaaagccat ctggaggttg aggattagag tccactagat    5880
ggggatacgc ggaacggtcg ggcgagtcat tagagtcctg gaaccggagg gtttaacgac    5940
ccaggaaccc ctagtgatgg agttggccac tccctctctg cgcgctcgct cgctcactga    6000
ggccgggcga ccaaaggtcg cccgacgccc gggctttgcc cgggcggcct cagtgagcga    6060
gcgagcgcgc agccttaatt aatccggacc acgtgcggac cgagcggccg caggaacccc    6120
tagtgatgga gttggccact ccctctctgc gcgctcgctc gctcactgag gccgggcgac    6180
caaaggtcgc ccgacgcccg gctttgccc gggcggcctc agtgagcgag cgagcgcgca    6240
gctgcctgca ggaagctgta agcttgtcga gaagtactag aggatcataa tcagccatac    6300
cacatttgta gaggttttac ttgctttaaa aaacctccca cacctccccc tgaacctgaa    6360
acataaaatg aatgcaattg ttgttgttaa cttgtttatt gcagcttata atggttacaa    6420
ataaagcaat agcatcacaa atttcacaaa taaagcattt ttttcactgc attctagttg    6480
tggtttgtcc aaactcatca atgtatctta tcatgtctgg atctgatcac tgatatcgcc    6540
taggagatcc gaaccagata agtgaaatct agttccaaac tattttgtca tttttaattt    6600
```

-continued

```
tcgtattagc ttacgacgct acacccagtt cccatctatt ttgtcactct tccctaaata    6660
atccttaaaa actccatttc caccectccc agttcccaac tattttgtcc gcccacagcg    6720
gggcattttt cttcctgtta tgttttaat caaacatcct gccaactcca tgtgacaaac     6780
cgtcatcttc ggctactttt tctctgtcac agaatgaaaa ttttctgtc atctcttcgt     6840 tattaatgtt tgtaattgac tgaatatcaa cgcttatttg cagcctgaat ggcgaatg      6898
```

<210> SEQ ID NO 33
<211> LENGTH: 7026
<212> TYPE: DNA
<213> ORGANISM: Artificial Sequence
<220> FEATURE:
<223> OTHER INFORMATION: Synthetic
<220> FEATURE:
<223> OTHER INFORMATION: AAV6-ZFN 3-LEFT

<400> SEQUENCE: 33

```
gacgcgccct gtagcggcgc attaagcgcg gcgggtgtgg tggttacgcg cagcgtgacc    60
gctacacttg ccagcgccct agcgcccgct cctttcgctt tcttcccttc ctttctcgcc    120
acgttcgccg gctttccccg tcaagctcta atcggggggc tccctttagg gttccgattt    180
agtgctttac ggcacctcga ccccaaaaaa cttgattagg gtgatggttc acgtagtggg    240
ccatcgccct gatagacggt ttttcgccct ttgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaatg agctgattta acaaaaattt    420
aacgcgaatt ttaacaaaat attaacgttt acaatttcag gtggcacttt tcggggaaat    480
gtgcgcggaa cccctatttg tttatttttc taaatacatt caaatatgta tccgctcatg    540
agacaataac cctgataaat gcttcaataa tattgaaaaa ggaagagtat gagtattcaa    600
catttccgtg tcgcccttat ccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacgatggc atgacagtaa gagaattatg cagtgctgcc    960
ataaccatga gtgataacac tgcggccaac ttacttctga caacgatcgg aggaccgaag    1020
gagctaaccg cttttttgca acatgggg gatcatgtaa ctcgccttga tcgttgggaa    1080
ccggagctga atgaagccat accaaacgac gagcgtgaca ccacgatgcc tgtagcaatg    1140
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
caggcaacta tggatgaacg aaatagacag atcgctgaga taggtgcctc actgattaag    1440
cattggtaac tgtcagacca gtttactca tatatacttt agattgattt aaaacttcat    1500
ttttaattta aaaggatcta ggtgaagatc ctttttgata atctcatgac caaaatccct    1560
taacgtgagt tttcgttcca ctgagcgtca gaccccgtag aaaagatcaa aggatcttct    1620
tgagatcctt ttttctgcg cgtaatctgc tgcttgcaaa caaaaaaacc accgctacca    1680
```

```
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacataccte gctctgctaa tcctgttacc agtggctgct    1860
gccagtggcg ataagtcgtg tcttaccggg ttggactcaa gacgatagtt accggataag    1920
gcgcagcggt cgggctgaac ggggggttcg tgcacacagc ccagcttgga gcgaacgacc    1980
tacaccgaac tgagatacct acagcgtgag cattgagaaa gcgccacgct tcccgaaggg    2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg gggcggagcc tatggaaaaa cgccagcaac    2220
gcggcctttt tacggttcct ggccttttgc tggccttttg ctcacatgtt ctttcctgcg    2280
ttatcccctg attctgtgga taaccgtatt accgcctttg agtgagctga taccgctcgc    2340
cgcagccgaa cgaccgagcg cagcgagtca gtgagcgagg aagcggaaga gcgcctgatg    2400
cggtattttc tccttacgca tctgtgcggt atttcacacc gcagaccagc cgcgtaacct    2460
ggcaaaatcg gttacggttg agtaataaat ggatgccctg cgtaagcggg tgtgggcgga    2520
caataaagtc ttaaactgaa caaaatagat ctaaactatg acaataaagt cttaaactag    2580
acagaatagt tgtaaactga atcagtcca gttatgctgt gaaaaagcat actggacttt    2640
tgttatggct aaagcaaact cttcattttc tgaagtgcaa attgcccgtc gtattaaaga    2700
ggggcgtggc caagggcatg gtaaagacta tattcgcggc gttgtgacaa tttaccgaac    2760
aactccgcgg ccgggaagcc gatctcggct tgaacgaatt gttaggtggc ggtacttggg    2820
tcgatatcaa agtgcatcac ttcttcccgt atgcccaact ttgtatagag agccactgcg    2880
ggatcgtcac cgtaatctgc ttgcacgtag atcacataag caccaagcgc gttggcctca    2940
tgcttgagga gattgatgag cgcggtggca atgccctgcc tccggtgctc gccggagact    3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg gcgtaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
cacggatctg ccctggcttc aggagatcgg aagacctcgg ccgtcgcggc gcttgccggt    3780
ggtgctgacc ccgatgaag tggttcgcat cctcggtttt ctggaaggcg agcatcgttt    3840
gttcgcccag gactctagct atagttctag tggttggcta cattattgaa gcatttatca    3900
gggttattgt ctcagagcat gcctgcaggc agctgcgcgc tcgctcgctc actgaggccg    3960
cccgggcgtc gggcgacctt tggtcgcccg gcctcagtga gcgagcgagc gcgcagagag    4020
ggagtggcca actccatcac tagggggttcc tgcggccgca cgcgtggagc tagttattaa    4080
```

```
tagtaatcaa ttacggggtc attagttcat agcccatata tggagttccg cgttacataa    4140
cttacggtaa atggcccgcc tggctgaccg cccaacgacc cccgcccatt gacgtcaata    4200
atgacgtatg ttcccatagt aacgtcaata gggactttcc attgacgtca atgggtggag    4260
tatttacggt aaactgccca cttggcagta catcaagtgt atcatatgcc aagtacgccc    4320
cctattgacg tcaatgacgg taaatggccc gcctggcatt atgcccagta catgacctta    4380
tgggactttc ctacttggca gtacatctac gtattagtca tcgctattac catggtgatg    4440
cggttttggc agtacatcaa tgggcgtgga tagcggtttg actcacgggg atttccaagt    4500
ctccacccca ttgacgtcaa tgggagtttg ttttgcacca aaatcaacgg gactttccaa    4560
aatgtcgtaa caactccgcc ccattgacgc aaatgggcgg taggcgtgta cggtgggagg    4620
tctatataag cagagctctc tggctaacta gagaacccac tgcttactgg cttatcgaaa    4680
ttaatacgac tcactatagg gagacccaag ctggctagcg tttaaactta agctgatcca    4740
ctagtccagt gtggtggaat tcgcctagag atctggcggc ggagagggca gaggaagtct    4800
tctaacctgc ggtgacgtgg aggagaatcc cggccctagg accatggact acaaagacca    4860
tgacggtgat tataaagatc atgacatcga ttacaaggat gacgatgaca gatggcccc    4920 caagaagaag aggaaggtcg gcattcatgg ggtacccgcc gctatggctg agaggccctt    4980
ccagtgtcga atctgcatgc gtaacttcag tgaccagtcc aacctgcgcg cccacatccg    5040
cacccacacc ggcgagaagc ttttgcctg tgacatttgt gggaggaaat ttgcccgcaa    5100
gtccgaccgc atcaagcata ccaagataca cacgggcagc caaaagccct tccagtgtcg    5160
aatctgcatg cgtaagtttg cccgctccga caacctgtcc gtgcatacca agatacacac    5220
gggcgagaag cccttccagt gtcgaatctg catgcgtaac ttcagtgagc gcggcaccct    5280
ggcccgccac atccgcaccc acaccggcga gaagcctttt gcctgtgaca tttgtgggag    5340
gaaatttgcc cgctccgacg ccctgaccca gcataccaag atacacctgc gggatcccca    5400
gctggtgaag agcgagctgg aggagaagaa gtccgagctg cggcacaagc tgaagtacgt    5460
gccccacgag tacatcgagc tgatcgagat cgccaggaac agcacccagg accgcatcct    5520
ggagatgaag gtgatggagt tcttcatgaa ggtgtacggc tacaggggaa agcacctggg    5580
cggaagcaga aagcctgacg gcgccatcta tacagtgggc agcccatcg attacggcgt    5640 gatcgtggac acaaaggcct acagcggcgg ctacaatctg cctatcggcc aggccgacga    5700
gatgcagaga tacgtgaagg agaaccagac ccggaataag cacatcaacc ccaacgagtg    5760
gtggaaggtg taccctagca gcgtgaccga gttcaagttc ctgttcgtga gcggccactt    5820
caagggcaac tacaaggccc agctgaccag gctgaaccgc aaaaccaact gcaatggcgc    5880
cgtgctgagc gtggaggagc tgctgatcgg cggcgagatg atcaaagccg gcaccctgac    5940
actggaggag gtgcggcgca gttcaacaa cggcgagatc aacttctgat aactcgagct    6000
gtgccttcta gttgccagcc atctgttgtt tgcccctccc ccgtgccttc cttgaccctg    6060
gaaggtgcca ctcccactgt cctttcctaa taaaatgagg aaattgcatc gcattgtctg    6120
agtaggtgtc attctattct ggggggtggg gtggggcagg acagcaaggg ggaggattgg    6180
gaagacaata gcaggcatgc tggggatgcg gtgggctcta tggcggaccg agcggccgca    6240 ggaacccta gtgatggagt tggccactcc ctctctgcgc gctcgctcgc tcactgaggc    6300
cgggcgacca aggtcgccc gacgcccggg ctttgcccgg gcggcctcag tgagcgagcg    6360
agcgcgcagc tgcctgcagg aagctgtaag cttgtcgaga agtactagag gatcataatc    6420
```

```
agccatacca catttgtaga ggttttactt gctttaaaaa acctcccaca cctcccctg    6480 aacctgaaac ataaaatgaa tgcaattgtt gttgttaact tgtttattgc agcttataat    6540
ggttacaaat aaagcaatag catcacaaat ttcacaaata aagcattttt ttcactgcat    6600
tctagttgtg gtttgtccaa actcatcaat gtatcttatc atgtctggat ctgatcactg    6660
atatcgccta ggagatccga accagataag tgaaatctag ttccaaacta ttttgtcatt    6720
tttaattttc gtattagctt acgacgctac acccagttcc catctatttt gtcactcttc    6780
cctaaataat ccttaaaaac tccatttcca cccctcccag ttcccaacta ttttgtccgc    6840
ccacagcggg gcattttttct tcctgttatg ttttaatca acatcctgc caactccatg     6900 tgacaaaccg tcatcttcgg ctactttttc tctgtcacag aatgaaaatt tttctgtcat    6960
ctcttcgtta ttaatgtttg taattgactg aatatcaacg cttatttgca gcctgaatgg    7020
cgaatg                                                                7026

<210> SEQ ID NO 34
<211> LENGTH: 7065
<212> TYPE: DNA
<213> ORGANISM: Artificial Sequence
<220> FEATURE:
<223> OTHER INFORMATION: Synthetic
<220> FEATURE:
<223> OTHER INFORMATION: AAV6-ZFN 3-RIGHT

<400> SEQUENCE: 34
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta aatcggggc tcccttagg gttccgattt      180 agtgctttac ggcacctcga cccccaaaaaa cttgattagg gtgatggttc acgtagtggg    240
ccatcgccct gatagacggt ttttcgccct tgacgttgg agtccacgtt ctttaatagt    300
ggactcttgt tccaaactgg aacaacactc aaccctatct cggtctattc ttttgattta    360
taagggattt tgccgatttc ggcctattgg ttaaaaaatg agctgattta acaaaaattt    420
aacgcgaatt ttaacaaaat attaacgttt acaatttcag gtggcacttt tcggggaaat    480
gtgcgcggaa cccctatttg tttatttttc taaatacatt caaatatgta tccgctcatg    540
agacaataac cctgataaat gcttcaataa tattgaaaaa ggaagagtat gagtattcaa    600
catttccgtg tcgcccttat ccctttttt gcggcatttt gccttcctgt ttttgctcac    660
ccagaaacgc tggtgaaagt aaaagatgct gaagatcagt tgggtgcacg agtgggttac    720
atcgaactgg atctcaacag cggtaagatc cttgagagtt ttcgccccga agaacgtttt    780
ccaatgatga gcacttttaa agttctgcta tgtggcgcgg tattatcccg tattgacgcc    840
gggcaagagc aactcggtcg ccgcatacac tattctcaga atgacttggt tgagtactca    900
ccagtcacag aaaagcatct tacggatggc atgacagtaa gagaattatg cagtgctgcc    960
ataaccatga gtgataacac tgcggccaac ttacttctga caacgatcgg aggaccgaag   1020
gagctaaccg cttttttgca acatggggg gatcatgtaa ctcgccttga tcgttgggaa   1080
ccggagctga atgaagccat accaaacgac gagcgtgaca ccacgatgcc tgtagcaatg    1140
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
```

```
caggcaacta tggatgaacg aaatagacag atcgctgaga taggtgcctc actgattaag    1440
cattggtaac tgtcagacca agtttactca tatatacttt agattgattt aaaacttcat    1500
ttttaattta aaaggatcta ggtgaagatc cttttttgata atctcatgac caaaatccct   1560
taacgtgagt tttcgttcca ctgagcgtca gaccccgtag aaaagatcaa aggatcttct    1620
tgagatcctt ttttttctgcg cgtaatctgc tgcttgcaaa caaaaaaacc accgctacca   1680
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacatacctc gctctgctaa tcctgttacc agtggctgct    1860
gccagtggcg ataagtcgtg tcttaccggg ttggactcaa gacgatagtt accggataag    1920
gcgcagcggt cgggctgaac ggggggttcg tgcacacagc ccagcttgga gcgaacgacc    1980
tacaccgaac tgagatacct acagcgtgag cattgagaaa gcgccacgct tcccgaaggg    2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg gggcggagcc tatggaaaaa cgccagcaac    2220
gcggcctttt tacggttcct ggccttttgc tggccttttg ctcacatgtt ctttcctgcg    2280
ttatccctg attctgtgga taaccgtatt accgcctttg agtgagctga taccgctcgc     2340
cgcagccgaa cgaccgagcg cagcgagtca gtgagcgagg aagcggaaga gcgcctgatg    2400
cggtatttc tccttacgca tctgtgcggt atttcacacc gcagaccagc cgcgtaacct     2460
ggcaaaatcg gttacggttg agtaataaat ggatgccctg cgtaagcggg tgtgggcgga    2520
caataaagtc ttaaactgaa caaaatagat ctaaactatg acaataaagt cttaaactag    2580
acagaatagt tgtaaactga aatcagtcca gttatgctgt gaaaaagcat actgactttt    2640
tgttatggct aaagcaaact cttcattttc tgaagtgcaa attgcccgtc gtattaaaga    2700
ggggcgtggc caagggcatg gtaaagacta tattcgcggc gttgtgacaa tttaccgaac    2760
aactccgcgg ccgggaagcc gatctcggct tgaacgaatt gttaggtggc ggtacttggg    2820
tcgatatcaa agtgcatcac ttcttcccgt atgcccaact ttgtatagag agccactgcg    2880
ggatcgtcac cgtaatctgc ttgcacgtag atcacataag caccaagcgc gttggcctca    2940
tgcttgagga gattgatgag cgcggtggca atgcccctgcc tccggtgctc gccggagact   3000
gcgagatcat agatatagat ctcactacgc ggctgctcaa acctgggcag aacgtaagcc    3060
gcgagagcgc caacaaccgc ttcttggtcg aaggcagcaa gcgcgatgaa tgtcttacta    3120
cggagcaagt tcccgaggta atcggagtcc ggctgatgtt gggagtaggt ggctacgtct    3180
ccgaactcac gaccgaaaag atcaagagca gcccgcatgg atttgacttg gtcagggccg    3240
agcctacatg tgcgaatgat gcccatactt gagccaccta actttgtttt agggcgactg    3300
ccctgctgcg taacatcgtt gctgctgcgt aacatcgttg ctgctccata acatcaaaca    3360
tcgacccacg gcgtaacgcg cttgctgctt ggatgcccga ggcatagact gtacaaaaaa    3420
acagtcataa caagccatga aaaccgccac tgcgccgtta ccaccgctgc gttcggtcaa    3480
ggttctggac cagttgcgtg agcgcatacg ctacttgcat tacagtttac gaaccgaaca    3540
ggcttatgtc aactgggttc gtgccttcat ccgtttccac ggtgtgcgtc acccggcaac    3600
cttgggcagc agcgaagtcg aggcatttct gtcctggctg gcgaacgagc gcaaggtttc    3660
ggtctccacg catcgtcagg cattggcggc cttgctgttc ttctacggca aggtgctgtg    3720
```

```
cacggatctg ccctggcttc aggagatcgg aagacctcgg ccgtcgcggc gcttgccggt    3780
ggtgctgacc ccgatgaag tggttcgcat cctcggtttt ctggaaggcg agcatcgttt     3840
gttcgcccag gactctagct atagttctag tggttggcta cattattgaa gcatttatca    3900
gggttattgt ctcagagcat gcctgcaggc agctgcgcgc tcgctcgctc actgaggccg    3960
cccgggcgtc gggcgacctt tggtcgcccg gcctcagtga gcgagcgagc gcgcagagag    4020
ggagtggcca actccatcac tagggggttcc tgcggccgca cgcgtggagc tagttattaa    4080
tagtaatcaa ttacggggtc attagttcat agcccatata tggagttccg cgttacataa    4140
cttacggtaa atggcccgcc tggctgaccg cccaacgacc cccgcccatt gacgtcaata    4200
atgacgtatg ttcccatagt aacgtcaata gggactttcc attgacgtca atgggtggag    4260
tatttacggt aaactgccca cttggcagta catcaagtgt atcatatgcc aagtacgccc    4320
cctattgacg tcaatgacgg taaatggccc gcctggcatt atgcccagta catgacctta    4380
tgggactttc ctacttggca gtacatctac gtattagtca tcgctattac catggtgatg    4440
cggttttggc agtacatcaa tgggcgtgga tagcggtttg actcacgggg atttccaagt    4500
ctccacccca ttgacgtcaa tgggagtttg ttttgcacca aaatcaacgg gactttccaa    4560
aatgtcgtaa caactccgcc ccattgacgc aaatgggcgg taggcgtgta cggtgggagg    4620
tctatataag cagagctctc tggctaacta gagaacccac tgcttactgg cttatcgaaa    4680
ttaatacgac tcactatagg gagacccaag ctggctagct tttaaactta agctgatcca    4740
ctagtccagt gtggtggaat tcgccatgga ctacaaagac catgacggtg attataaaga    4800
tcatgacatc gattacaagg atgacgatga caagatggcc cccaagaaga agaggaaggt    4860
cggcatccac ggggtacccg ccgctatggc tgagaggccc ttccagtgtc gaatctgcat    4920
gcgtaacttc agtcagtcct ccgacctgtc ccgccacatc cgcacccaca ccggcgagaa    4980
gccttttgcc tgtgacattt gtgggaggaa atttgcctgg cgctcctccc tgcgccagca    5040
taccaagata cacacgcatc ccagggcacc tattcccaag cccttccagt gtcgaatctg    5100
catgcgtaac ttcagtcagt ccggcgacct gacccgccac atccgcaccc acaccggcga    5160 gaagccttt gcctgtgaca tttgtgggag gaaatttgcc cgccgcgccg accgcgccaa    5220
gcataccaag atacacacgc acccgcgcgc cccgatcccg aagcccttcc agtgtcgaat    5280
ctgcatgcgt aacttcagtc gctccgacga cctgacccgc cacatccgca cccacaccgg    5340
cgagaagcct tttgcctgtg acatttgtgg gaggaaattt gcccagcgct ccaccctgtc    5400
ctcccatacc aagatacacc tgcggggatc ccagctggtg aagagcgagc tggaggagaa    5460
gaagtccgag ctgcggcaca gctgaagta cgtgcccac gagtacatcg agctgatcga    5520
gatcgccagg aacagcaccc aggaccgcat cctggagatg aaggtgatgg agttcttcat    5580
gaaggtgtac ggctacaggg gaaagcacct gggcggaagc agaaagcctg acggcgccat    5640
ctatacagtg ggcagcccca tcgattacgg cgtgatcgtg gacacaaagg cctacagcgg    5700
cggctacaat ctgcctatcg gccaggccga cgagatggag agatacgtgg aggagaacca    5760
gacccgggat aagcacctca cccccaacga gtggtggaag gtgtaccccta gcagcgtgac    5820 cgagttcaag ttcctgttcg tgagcggcca cttcaagggc aactacaagg cccagctgac    5880
caggctgaac cacatcacca actgcaatgg cgccgtgctg agcgtggagg agctgctgat    5940
cggcggcgag atgatcaaag ccggcaccct gacactggag gaggtgcggc gcaagttcaa    6000
caacggcgag atcaacttca gatcttgata actcgagctg tgccttctag ttgccagcca    6060
tctgttgttt gccccctccc cgtgccttcc ttgaccctgg aaggtgccac tcccactgtc    6120
```

-continued

```
ctttcctaat aaaatgagga aattgcatcg cattgtctga gtaggtgtca ttctattctg    6180
gggggtgggg tggggcagga cagcaagggg gaggattggg aagacaatag caggcatgct    6240
ggggatgcgg tgggctctat ggcggaccga gcggccgcag gaaccccctag tgatggagtt    6300 ggccactccc tctctgcgcg ctcgctcgct cactgaggcc gggcgaccaa aggtcgcccg    6360
acgcccgggc tttgcccggg cggcctcagt gagcgagcga gcgcgcagct gcctgcagga    6420
agctgtaagc ttgtcgagaa gtactagagg atcataatca gccataccac atttgtagag    6480
gttttacttg cttaaaaaaa cctcccacac ctcccctga acctgaaaca taaaatgaat    6540
gcaattgttg ttgttaactt gtttattgca gcttataatg gttacaaata aagcaatagc    6600
atcacaaatt tcacaaataa agcattttt tcactgcatt ctagttgtgg tttgtccaaa    6660
ctcatcaatg tatcttatca tgtctggatc tgatcactga tatcgcctag agatccgaa    6720 ccagataagt gaaatctagt tccaaactat tttgtcattt ttaattttcg tattagctta    6780
cgacgctaca cccagttccc atctattttg tcactcttcc ctaaataatc cttaaaaact    6840
ccatttccac ccctcccagt tcccaactat tttgtccgcc cacagcgggg cattttctt    6900 cctgttatgt ttttaatcaa acatcctgcc aactccatgt gacaaaccgt catcttcggc    6960 tacttttct ctgtcacaga atgaaaattt ttctgtcatc tcttcgttat taatgtttgt    7020
aattgactga atatcaacgc ttatttgcag cctgaatggc gaatg                    7065
```

<210> SEQ ID NO 35
<211> LENGTH: 420
<212> TYPE: PRT
<213> ORGANISM: Artificial Sequence
<220> FEATURE:
<223> OTHER INFORMATION: Synthetic
<220> FEATURE:
<223> OTHER INFORMATION: ZFN LEFT

<400> SEQUENCE: 35

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Met Ala Glu Arg Pro Phe Gln Cys
        35                  40                  45

Arg Ile Cys Met Arg Asn Phe Ser Gln Ser Ser Asp Leu Ser Arg His
    50                  55                  60

Ile Arg Thr His Thr Gly Glu Lys Pro Phe Ala Cys Asp Ile Cys Gly
65                  70                  75                  80

Arg Lys Phe Ala Trp Arg Ser Ser Leu Arg Gln His Thr Lys Ile His
                85                  90                  95

Thr His Pro Arg Ala Pro Ile Pro Lys Pro Phe Gln Cys Arg Ile Cys
            100                 105                 110

Met Arg Asn Phe Ser Gln Ser Gly Asp Leu Thr Arg His Ile Arg Thr
        115                 120                 125

His Thr Gly Glu Lys Pro Phe Ala Cys Asp Ile Cys Gly Arg Lys Phe
    130                 135                 140

Ala Arg Arg Ala Asp Ala Lys His Thr Lys Ile His Thr His Pro
145                 150                 155                 160

Arg Ala Pro Ile Pro Lys Pro Phe Gln Cys Arg Ile Cys Met Arg Asn
                165                 170                 175

Phe Ser Arg Ser Asp Asp Leu Thr Arg His Ile Arg Thr His Thr Gly
```

```
                180             185             190
Glu Lys Pro Phe Ala Cys Asp Ile Cys Gly Arg Lys Phe Ala Gln Arg
            195                 200                 205

Ser Thr Leu Ser Ser His Thr Lys Ile His Leu Arg Gly Ser Gln Leu
        210                 215                 220

Val Lys Ser Glu Leu Glu Lys Lys Ser Glu Leu Arg His Lys Leu
225             230                 235                 240

Lys Tyr Val Pro His Glu Tyr Ile Glu Leu Ile Glu Ile Ala Arg Asn
                245                 250                 255

Ser Thr Gln Asp Arg Ile Leu Glu Met Lys Val Met Glu Phe Phe Met
            260                 265                 270

Lys Val Tyr Gly Tyr Arg Gly Lys His Leu Gly Gly Ser Arg Lys Pro
            275                 280                 285

Asp Gly Ala Ile Tyr Thr Val Gly Ser Pro Ile Asp Tyr Gly Val Ile
            290                 295                 300

Val Asp Thr Lys Ala Tyr Ser Gly Gly Tyr Asn Leu Pro Ile Gly Gln
305                 310                 315                 320

Ala Asp Glu Met Glu Arg Tyr Val Glu Glu Asn Gln Thr Arg Asp Lys
                325                 330                 335

His Leu Asn Pro Asn Glu Trp Trp Lys Val Tyr Pro Ser Ser Val Thr
            340                 345                 350

Glu Phe Lys Phe Leu Phe Val Ser Gly His Phe Lys Gly Asn Tyr Lys
            355                 360                 365

Ala Gln Leu Thr Arg Leu Asn His Ile Thr Asn Cys Asn Gly Ala Val
            370                 375                 380

Leu Ser Val Glu Glu Leu Leu Ile Gly Gly Glu Met Ile Lys Ala Gly
385                 390                 395                 400

Thr Leu Thr Leu Glu Glu Val Arg Arg Lys Phe Asn Asn Gly Glu Ile
                405                 410                 415

Asn Phe Arg Ser
            420

<210> SEQ ID NO 36
<211> LENGTH: 381
<212> TYPE: PRT
<213> ORGANISM: Artificial Sequence
<220> FEATURE:
<223> OTHER INFORMATION: Synthetic
<220> FEATURE:
<223> OTHER INFORMATION: ZFN RIGHT

<400> SEQUENCE: 36

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Met Ala Glu Arg Pro Phe Gln Cys
            35                  40                  45

Arg Ile Cys Met Arg Asn Phe Ser Asp Gln Ser Asn Leu Arg Ala His
        50                  55                  60

Ile Arg Thr His Thr Gly Glu Lys Pro Phe Ala Cys Asp Ile Cys Gly
65                  70                  75                  80

Arg Lys Phe Ala Arg Lys Ser Asp Arg Ile Lys His Thr Lys Ile His
                85                  90                  95

Thr Gly Ser Gln Lys Pro Phe Gln Cys Arg Ile Cys Met Arg Lys Phe
            100                 105                 110
```

```
Ala Arg Ser Asp Asn Leu Ser Val His Thr Lys Ile His Thr Gly Glu
        115                 120                 125
Lys Pro Phe Gln Cys Arg Ile Cys Met Arg Asn Phe Ser Glu Arg Gly
    130                 135                 140
Thr Leu Ala Arg His Ile Arg Thr His Thr Gly Glu Lys Pro Phe Ala
145                 150                 155                 160
Cys Asp Ile Cys Gly Arg Lys Phe Ala Arg Ser Asp Ala Leu Thr Gln
                165                 170                 175
His Thr Lys Ile His Leu Arg Gly Ser Gln Leu Val Lys Ser Glu Leu
            180                 185                 190
Glu Glu Lys Lys Ser Glu Leu Arg His Lys Leu Lys Tyr Val Pro His
        195                 200                 205
Glu Tyr Ile Glu Leu Ile Glu Ile Ala Arg Asn Ser Thr Gln Asp Arg
    210                 215                 220
Ile Leu Glu Met Lys Val Met Glu Phe Phe Met Lys Val Tyr Gly Tyr
225                 230                 235                 240
Arg Gly Lys His Leu Gly Gly Ser Arg Lys Pro Asp Gly Ala Ile Tyr
                245                 250                 255
Thr Val Gly Ser Pro Ile Asp Tyr Gly Val Ile Val Asp Thr Lys Ala
            260                 265                 270
Tyr Ser Gly Gly Tyr Asn Leu Pro Ile Gly Gln Ala Asp Glu Met Gln
        275                 280                 285
Arg Tyr Val Lys Glu Asn Gln Thr Arg Asn Lys His Ile Asn Pro Asn
    290                 295                 300
Glu Trp Trp Lys Val Tyr Pro Ser Ser Val Thr Glu Phe Lys Phe Leu
305                 310                 315                 320
Phe Val Ser Gly His Phe Lys Gly Asn Tyr Lys Ala Gln Leu Thr Arg
                325                 330                 335
Leu Asn Arg Lys Thr Asn Cys Asn Gly Ala Val Leu Ser Val Glu Glu
            340                 345                 350
Leu Leu Ile Gly Gly Glu Met Ile Lys Ala Gly Thr Leu Thr Leu Glu
        355                 360                 365
Glu Val Arg Arg Lys Phe Asn Asn Gly Glu Ile Asn Phe
    370                 375                 380
```

PERMANENT GENE CORRECTION BY MEANS OF NUCLEOTIDE-MODIFIED MESSENGER RNA

CROSS-REFERENCES TO RELATED APPLICATIONS

This application is a continuation of copending U.S. application Ser. No. 15/094,926 filed on Apr. 8, 2016, which claims priority to International Patent Application PCT/EP2014/071343 filed on Oct. 6, 2014 and designating the United States of America, which was published in English, and claims priority of Germany Patent Application DE 10 2013 111 099.1 filed on Oct. 8, 2013, which are all incorporated herein by reference in their entireties.

SUBMISSION OF SEQUENCE LISTING ON ASCII.TXT FILE

The content of the following submission on ASCII.txt file is incorporated herein by reference in its entirety: a computer readable form (CRF) of the Sequence Listing (file name: 4567-2012702_SeqList.txt, date recorded: Jun. 24, 2016, size: 88,787 bytes).

FIELD

The present invention concerns a nucleotide-modified messenger RNA for the permanent correction of a genetic alteration on a DNA. The invention further concerns a nucleotide-modified messenger RNA in combination with a repair template. It also concerns a pharmaceutical composition. It finally relates to methods for the correction of a genetic alteration on a DNA.

BACKGROUND

The gene therapy refers to the insertion of nucleic acids such as DNA or RNA into somatic cells of an individual, e.g. in order to treat a disease. By doing so, usually an intact gene should be inserted into the genome of the target cell in order to replace a defective gene which is causally related to the development of the disease. Basically a gene therapy has chances of success only for such diseases which are based on the alteration of only one or a few number of genes.

Surfactant protein B deficiency and cystic fibrosis (CF) are severe, congenital, fatal diseases for which currently no satisfying therapies do exist. Surfactant protein B deficiency is rare and occurs in about one out of one million newborns. Surfactant protein B (SP-B) is a pulmonary surfactant associated protein that plays an essential role in the alveolar stability by lowering the surface tension at the air-liquid interface in the lung. Mutations of the SP-B encoding gene (SFTPB) results in a rapidly fatal respiratory failure associated with alveolar proteinosis, within the first year of life. The cystic fibrosis is the most prevalent life-limiting autosomal-recessive disease in Caucasian populations. It can be found in one out of 2,500 newborns and affects more than 70,000 people world-wide. Mutations in the gene coding for the "cystic fibrosis transmembrane conductance regulator" (CFTR), a chloride channel, result in an impaired anion secretion and hyperabsorption of sodium across epithelia. The chronic lung disease is the major factor contributing to mortality and morbidity in CF patients. Even with the current therapy, the mean survival is only between 30 and 40 years.

RELATED PRIOR ART

Current gene therapeutic efforts with DNA-based or viral vectors remain largely unsuccessful in treating these fatal illnesses. As the airways evolved in direct contact to the environment, their inherent defense mechanisms present a significant barrier for the delivery of foreign vectors into the lung. In addition, the use of most of the viral vectors presents a health risk since they can act as oncogenes.

Kormann et al. (2011), Expression of therapeutic proteins after delivery of chemically modified mRNA in mice, Letters to Nature Biotechnology, pages 1-6, describe a therapeutic approach for the treatment of SP-B deficiency where a functional nucleotide modified messenger RNA (mRNA) encoding SP-B is introduced into alveolar cells of the mouse. This is affected by intratracheal high pressure application of the SP-B mRNA. Through the nucleotide modification 25% of the uridine and cytidine were replaced by 2-thiouridine (s2U) and 5-methylcytidine (m5C), respectively. As a result the modified mRNA has less immunogenicity and is more stable than its unmodified counter-part. However, this approach has the disadvantage that the nucleotide modified mRNA can compensate the SP-B deficiency only for a limited time period, i.e. until it will be degraded by RNases so that a detectable effect will soon disappear. A permanent gene supplementation or gene correction cannot be realized.

McCaffrey et al. (2013), Targeted genome engineering with zinc-finger nucleases, TALENs and CRISPR. The buzz on the cut: from dream to reality, an internet article posted on Jul. 1, 2013, in *Therapeutics* and tagged gene engineering, genome editing, mRNA (on: zon.trilinkbiotech.com), suggests the use of the ZFN and TALEN nucleases encoded by synthetic mRNAs for transient expression in genome engineering. He mentions that mRNAs could be made less immunogenic and non-toxic by substitution of cytosine and uridine with 5-methylcytosine and pseudouridine.

US 2013/0117870A1 discloses the use of mRNA encoding the TALEN nuclease for producing genetically modified or transgenic animals, respectively. It also discloses the transfection of swine fibroblasts with TALEN encloding nucleotide-modified mRNA.

SUMMARY OF THE INVENTION

Against this background it is an object of the present invention to provide a new substance which can be used as a tool within the framework of the gene therapy. With this substance the preconditions should be established for a permanent correction of a genetic alteration on a DNA.

This measure is realized by the provision of a nuclease encoding nucleotide-modified messenger RNA (nec-mRNA).

The inventors have surprisingly recognized that by the gene therapeutically use of a nec-mRNA the preconditions are established to correct a genetic alteration on the DNA in a permanent manner. For that purpose the nec-mRNA is transfected into the cytoplasm of a target cell and will there be translated into a nuclease. The nuclease is then transported into the nucleus. In the nucleus it can bind to the DNA which comprises the genetic alteration and can initiate a double-strand break (DSB). The DSB as a repair mechanism stimulates a homologous recombination, thus establishing the precondition for an exchange of the genetic alteration against e.g. the wild type sequence of the corresponding DNA section. Here the temporarily existing nuclease activity is advantageous, especially in contrast to any DNA or virus encoded nuclease activities where there is the risk of an integration into the genome of the host, and gives additional therapeutic safety for the system according to the invention.

This finding was surprising. In the art so far nucleotide-modified mRNA is mostly used for the direct substitution of the deficient gene or protein, respectively. For example Kormann et al. (cit. loc.) describe a nucleotide-modified mRNA which encodes the red fluorescent protein (RFP), the mouse erythropoietin (mEpo) or the surfactant protein B. The WO 2011/012316 also describes nucleotide-modified mRNA which encodes the surfactant protein B.

Karikó et.al. (2012), Increased Erythropoiesis in Mice Injected With Submicrogram Quantities of Pseudouridine-containing mRNA Encoding Erythropoietin, Molecular Therapy, Vol. 16, No. 11, pages 1833-1844, describe the use of nucleotide-modified mRNA for the synthesis of erythropoietin in a mouse model and propose the therapeutic use of nucleotide-modified mRNA.

The use of nec-mRNA as a molecular tool for establishing a permanent gene correction is not described in the prior art.

According to the invention "nucleotide-modified messenger RNA" refers to such an mRNA, where a part of the nucleotides, or nucleosides or nucleobases is modified, i.e. changed. In this respect the terms "nucleotides" and "nucleosides" are used interchangeably. Preferably it is referred to a chemical modification. This modification has the result that the mRNA is more stable and has less immunogenicity. Nucleotide-modified messenger RNA is generally known in the prior art, cf. for example WO 2011/012316. The content of the before-mentioned publication is incorporated herein by reference. Examples for chemically-modified nucleotides or nucleosides are pseudouridine (ψ), 5-methylcytidine (m5C), N6-methyladenosine (m6A), 5-methyluridine (m5U) or 2-thiouridine (s2U).

According to the invention the use of a nec-mRNA also encompasses the use of different nec-mRNAs, such as a pair of nec-mRNAs, where each nec-mRNA could encode different nucleases. For example, one nuclease might bind and cleave upstream and the other nuclease downstream of the genetic alteration and, in doing so, create the optimum preconditions for a homologous recombination.

A "genetic alteration" refers to any change of the sequence on the DNA in comparison to the wild type, e.g. caused by a mutation or a polymorphism. Preferably the genetic alteration can be found in a gene resulting in a loss of function of the encoded protein or even in a complete knockout.

A "correction" of a genetic alteration on the DNA or a "gene correction" refers to a permanent exchange of the genetic alteration or the genetically altered gene for a nucleic acid section without such alteration, for example of the wild type.

According to a preferred embodiment up to including approx. 100% of the uridine nucleotides and/or up to including approx. 100% of the cytidine nucleotides, preferably up to including approx. 70% of the uridine nucleotides and/or up to including approx. 70% of the cytidine nucleotides, further preferably up to including approx. 50% of the uridine nucleotides and/or up to including approx. 50% of the cytidine nucleotides, further preferably up to including approx. 25% of the uridine nucleotides and/or up to including approx. 25% of the cytidine nucleotides, and highly preferably approx. 10% of the uridine nucleotides and/or approx. 10% of the cytidine nucleotides of the nec-mRNA are modified, further preferably by exchanging uridine for 2-thiouridine (s2U) and/or pseudouridine (ψ) and/or by exchanging cytidine for 5-methylcytidine (m5C).

This measure has the advantage that through the prescribed content of nucleotide modifications an mRNA is provided which is significantly stable and little immunogenic. Even more, the inventors could surprisingly realize that it is sufficient if only up to including about 10% of the cytidines are replaced by 5-methylcytidine (m5C) and/or up to including approx. 10% of the uridines are replaced by 2-thiouridine (s2U). The inventors could provide evidence that also such slightly modified nec-mRNA is stable and little immunogenic. Since the nucleotide modification is complex, this has the advantage that the nec-mRNA according to the invention, because of the low concentration of nucleotide modifications, can be produced in a cost-saving manner. Besides of reducing costs, the lowering of the portion of modified nucleotides has also the advantage that the efficiency of the translation is increased. This is because very high portions of specifically modified nucleotides, such as 2-thiouridine (s2U), significantly interfere with the translation of the modified mRNA. However, with lower portions an optimum translation can be observed.

According to a preferred embodiment the genetic alteration is located in a lung protein, preferably in a surfactant protein, further preferably in the surfactant protein B (SP-B), further preferably a receptor protein including cystic fibrosis transmembrane and conductance regulator (CFTR), further preferably a transcription factor including Foxp3.

This measure has the advantage that the invention can be used as a therapeutic tool in the therapy of lung diseases for which currently no satisfying therapies do exist.

According to a preferred embodiment the nec-mRNA encodes a nuclease which is configured to bind to the DNA upstream and/or downstream of the genetic alteration.

This measure has the advantage that the encoded nuclease binds next to the genetic alteration, there catalyzes a double-strand break (DSB), thereby initiate cellular repair mechanisms including a homologous recombination (HR). In this way only the genetic alteration can be replaced in a targeted manner, e.g. by the wild type.

The nuclease is preferably selected from the group consisting of: zinc-finger nucleases (ZFNs), transcription activator-like effector nucleases (TALEN), CRISPR/Cas9, and dimeric CRISPR RNA guided FokI nucleases.

Zinc-finger nucleases (ZFNs) and transcription activator-like effector nucleases (TALEN) are artificial endonucleases which bind to specific sequences upstream and/or downstream of the genetic alteration on the DNA via DNA-binding polypeptides. The targeted configuration, the structure and the functionality of these nucleases are known to the person skilled in the art. Reference is made in this connection to the document of Carlson et al. (2012), Targeting DNA with fingers and TALENs, Molecular Therapy-Nucleic Acids 1, e3. "Cas" stands for "CRISPR associated". CRISPR stands for "Clustered Regularly Interspaced Short Palindromic Repeats". Cas9 is a nuclease which has originally discovered in bacteria, which binds in a targeted manner to distinct sections of the DNA via the CRISP/Cas system by means of a short complementary single-stranded RNA; cf. Mail et al. (2013), RNA-guided human genome engineering via Cas9, Science 339(6121), pages 823-826 and Cong et al. (2013), Multiplex genome engineering using CRISPR/Cas systems, Science 339(6121), pages 819-823; and Tsai et al. (2014), Dimeric CRISPR RNA-guided FokI nucleases for highly specific genome editing, Nature Biotechnology 32, p. 569-576. These publications are incorporated herein by reference.

According to a preferred embodiment of the invention the nec-mRNA is coupled to an aptamer.

This measure has the advantage that the binding site of the nec-mRNA can be adjusted to defined target cells by a sequence-specific design of the aptamer. In this way it can be ensured that the nec-mRNA corrects the genetic alteration in a targeted manner only in specific cells where it is necessary. If, for example, the correction of a lung protein is intended, such aptamers are coupled to the nec-mRNA which selectively bind to cells of the lung tissue. Cells which are not affected by the genetic alteration remain untouched. This measure results in additional therapeutic safety. By the so-called SELEX method such aptamer sequences can be enriched which bind to the desired cell or the desired cell membrane structure, respectively.

According to a preferred embodiment the nec-mRNA is packed into nanoparticles.

This measure has the advantage that the absorption of the nec-mRNA into the cell is significantly improved, in particular into cells of the lung tissue. In particular, nanoparticle associated or packed nec-mRNA can be administered intravenously (i. v.) and still can reach the lung cells. Such a lung-cell targeted i.v. administration probably won't be possible without using nanoparticles. Examples for appropriate nanoparticles are the lipid GL67/DOPE and biocompatible chitosan-coated nanoparticles. In this connection "nanoparticle" refers to a particle between approx. 1 and approx. 300 nanometers in size (hydrodynamic diameter), preferably between approx. 50 nm and approx. 250 nm, further preferably between approx. 75 nm and approx. 200 nm, further preferably between approx 100 nm and approx. 175 nm, and highly preferably between approx. 150 nm and approx. 160 nm.

According to a preferred embodiment the nanoparticle is coated with chitosan.

This measure has the advantage that the respirability is further increased. In addition, chitosan has been proven as being particularly biocompatible resulting in an increase of the tolerance of the nec-mRNA by a living being.

Another subject matter of the present invention is the nec-mRNA according to the invention in combination with a repair template.

A "repair template" refers to a nucleic acid molecule, such as a DNA fragment, which comprises a nucleotide section which should be exchanged by homologous recombination (HR) for the section on the DNA comprising the genetic alteration. For example, this nucleotide section corresponds to the wild type or the "healthy gene", respectively, which does not comprise the genetic alteration. Upstream and downstream of the genetic alteration the repair template comprises sections which are significantly homologous to the DNA that a hybridization and homologous recombination can take place after the nuclease has induced a double-strand break.

The combination according to the invention of the nec-mRNA and the repair template allows a permanent correction of the genetic alteration by a lifelong expression of the corrected protein. As a consequence, nec-mRNA and repair template are in this way a "gene correction set" according to the invention.

It goes without saying that the repair template can comprise an inducible promoter by means of which the expression of the repaired gene can be controlled in a targeted manner.

According to a preferred embodiment of the invention the repair template is packed into an adeno-associated viral vector (AAV), and/or is encoded by a plasmid DNA, and/or is packed into a lentiviral vector, and/or is packed into a protein-capped adenoviral vector (AdV).

This measure has the advantage that it is made use of an established principle of the introduction of genetic information into the cell. AAV, lentiviral and AdV vectors have been proven successful in the practice of gene transfer because of the absence of gene toxic side effects.

Another subject matter of the present invention is a pharmaceutical composition comprising a nec-m RNA, preferably the before-mentioned nec-m RNA according to the invention, and further preferably in addition a repair template. Furthermore, the pharmaceutical composition is provided for the treatment of a lung disease which might be surfactant protein B deficiency and/or cystic fibrosis (CF) and/or Asthma and/or chronic obstructive pulmonary disease (COPD).

The features, characteristics and advantages of the nec-mRNA according to the invention also apply to the composition according to the invention.

Also disclosed is a method for the correction of a genetic alteration on a DNA comprising the following steps: (1) introducing a repair template into a DNA-containing cell, which comprises the genetic alteration to be corrected, (2) introducing a nec-mRNA into the cell. The cell can preferably be a lung cell and the introduction is preferably realized by means of high pressure application of the repair template and the nec-mRNA into the lung.

Both, the repair template, preferably packed into a AAV vector, as well as the nec-mRNA, preferably packed into nanoparticles, can be administered systemically or intravenously, respectively. This is of particular advantage if an application into the respiratory tract is not possible because of a mucus obstruction of the lung.

Another subject-matter of the present invention relates to a method for the correction of a genetic alteration on a DNA comprising the following steps: (1) introducing a repair template into a living being having a genetically altered DNA to be corrected, (2) introducing a nec-mRNA into the living being. The living being can be preferably a human being, and the introduction is preferably realized by means of high pressure application of the repair template and the nec-mRNA into the lung of the living being.

The features, advantages, further developments, embodiments disclosed in relation to the nec-mRNA, combination and pharmaceutical composition according to the invention apply to the methods according to the invention in equal measure.

It goes without saying that the before-mentioned features and those to be explained in the following embodiments cannot only be used in the combination specifically indicated but also in other combinations or in isolated manner without departing from the scope of the invention.

The invention will now be explained on the basis of embodiments resulting in further advantages, characteristics and features.

Reference is made to the enclosed figures which show the following:

BRIEF DESCRIPTION OF THE FIGURES

FIG. 4 shows the homology directed repair of the SP-B locus in mouse fibroblasts in vitro by TALEN, encoded by modified mRNA.

FIG. 9 Z3 pair amino acid sequence. Amino acid sequence of FLAG-tagged a, left Z3 arm (SEQ ID no. 35) and b, right Z3 arm (SEQ ID no. 36).

FIG. 11 3xFLAG+Clara cells 24 h after i.t. administration of PBS or unmodified or differently modified Z3 nec-mRNA, with or without NPs. Z3 protein expression was quantified viai flow cytometry against 3xFLAG (n=5 mice per group). Percentages of 3xFLAG+Clara cells *, P<0.05 versus unmodified mRNA; **, P<0.01 versus "without NP". Boxes represent medians±IQRs. Whiskers represent the minimum and maximum observations.

FIG. 19 Representative photographs of the lungs from groups +Doxy, A and B, before and after perfusion and lung function measurements. n=3 mice per group were examined.

FIG. 20 Representative photographs of the lungs from groups C to F, before and after perfusion and lung function measurements. n=3 mice per group were examined.

FIG. 24 3xFLAG expression score (combined semiquantitative analysis of the immunohistochemistry shown in FIG. 2h). Boxes represent medians±IQRs (interquartile range). *, $P<0.05$ versus Doxy-control and group A. The lavage was harvested 20 d after doxycycline removal.

DESCRIPTION OF PREFERRED EMBODIMENTS

1. Optimizing the nec-mRNA

Figure 1:
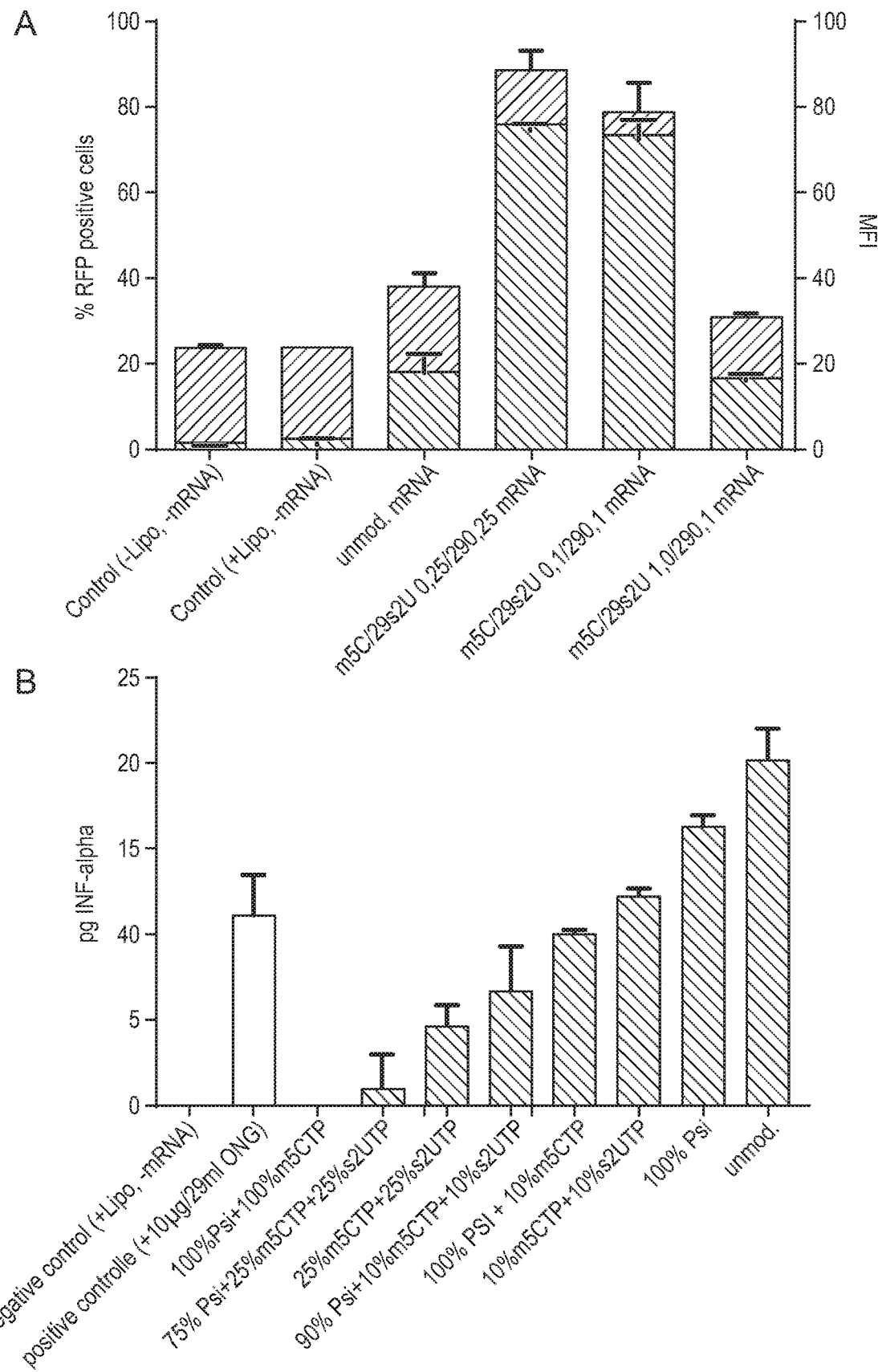
FIG. 1 shows the optimizing of the nec-mRNA by varying the portion of modified nucleotides.

In Kormann et al. (2011; cit. loc.) it is described that the replacement of 25% of each uridine and cytidine in the mRNA by 2-thiouridine and 5-methylcytidine in the SP-B deficient mouse results in a significantly stable and low immunogenic SP-B mRNA. The inventors have tested in an experiment whether the portion of modified nucleotides can be further reduced. The result of such an experiment is shown in FIG. 1.

In a first approach the inventors have manufactured an mRNA encoding the red fluorescent protein (RFP), where different levels of uridine and cytidine were replaced by 2-thiouridine (s2U) and 5-methylcytidine (m5C), namely 25% of each, 10% of each, and 100% of m5C and 10% of s2U. With these RNA molecules A-549 cells were transfected and after 24 hours the median of the fluorescence intensity (MIT) as the size of the transfection efficiency and a positive expression were measured. The result is shown in FIG. 1A. It can be seen that with a substitution of each of 25% or 10% an optimum expression is detectable; cf. 4th and 5th column.

In a further approach the immunogenicity of the modified mRNA molecules was examined. For this purpose, in addition to the s2U and m5C modified mRNAs also pseudouridine (Psi) modified mRNA molecules were manufactured which all encode zinc-finger nucleases (ZFN-5; both directions). With the chemically-modified mRNAs PBMCs were transfected via liposome fusion (Lipofectamin-2000). In the following, in an ELISA the expression of IFN-alpha was measured as a rate for the immunogenicity. The result is shown in FIG. 1B. Here it becomes evident that the use of an unmodified mRNA results in a very strong immunoreaction (column far right). When using 10% of each m5C/s2U (6th approach) and 25% of each m5C/s2U (5th approach), the immunogenicity is significantly reduced.

The low replacement of modified nucleotides has the advantage that the nec-mRNA is producible in a significantly cheaper manner than the nucleotide-modified mRNAs of the prior art where considerably higher portions of the nucleotides are replaced. It has further the advantage that the efficiency of the translation is optimized.

2. Principle of the Permanent Gene Correction by the Use of nec-mRNA

Figure 2:
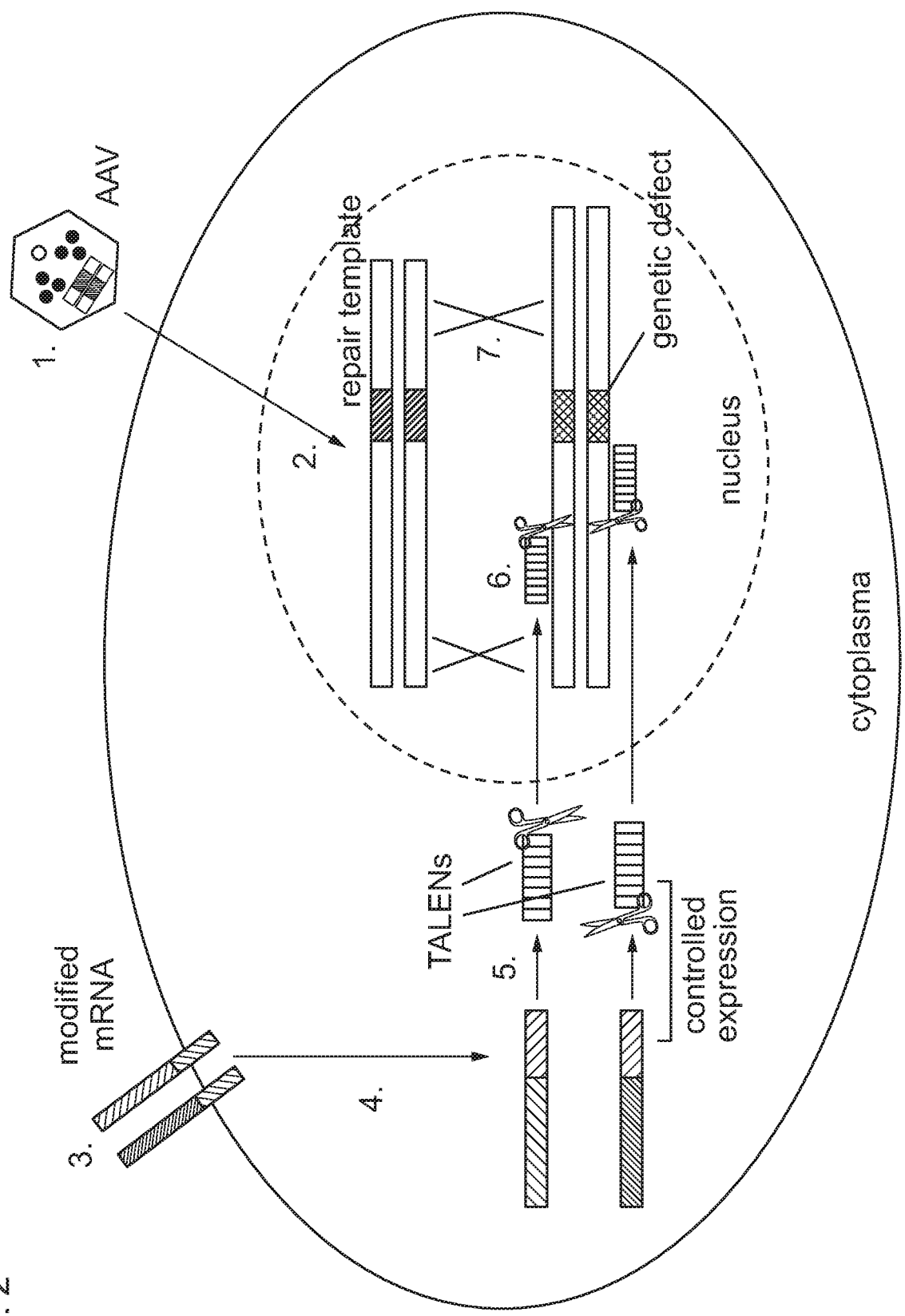
FIG. 2 shows the principle of the permanent gene correction by the use of nec-mRNA.

The inventors have developed a system to achieve a permanent correction of the gene loci which are present in mutated form in several diseases such as severe congenital lung diseases, in order to allow a stable lifelong expression of the corrected protein. This system is shown in FIG. 2. A lung efficient AAV vector (1.) shuttles the repair template into the cell and the nucleus (2.). Subsequently, a modified, aptamer-coupled mRNA encoding a specific nuclease pair (3.) is transfected into the cytoplasm of the target cell (4.), where it is translated into the nuclease pair proteins. The duration and strength of the expression can be influenced or controlled by means of different chemical modifications (5.). The nuclease pair is transported into the nucleus, where it binds to the target region and creates a double-strand break (DSB) (6.). The DSB stimulates a HR as a repair mechanism, exchanging the genetic defect for the corrected repair template (7.).

3. In Vivo Gene Correction at the SP-B Locus of the Mouse by nec-mRNA

Next, it was examined whether a modified mRNA encoding a nuclease can catalyze an effective gene correction in the lung cell of the mouse in vivo. For this purpose, experiments were performed with a mouse having SP-B deficiency. The employed mouse model is described in detail in Kormann et al. (2011; cit. loc.).

Figure 3:
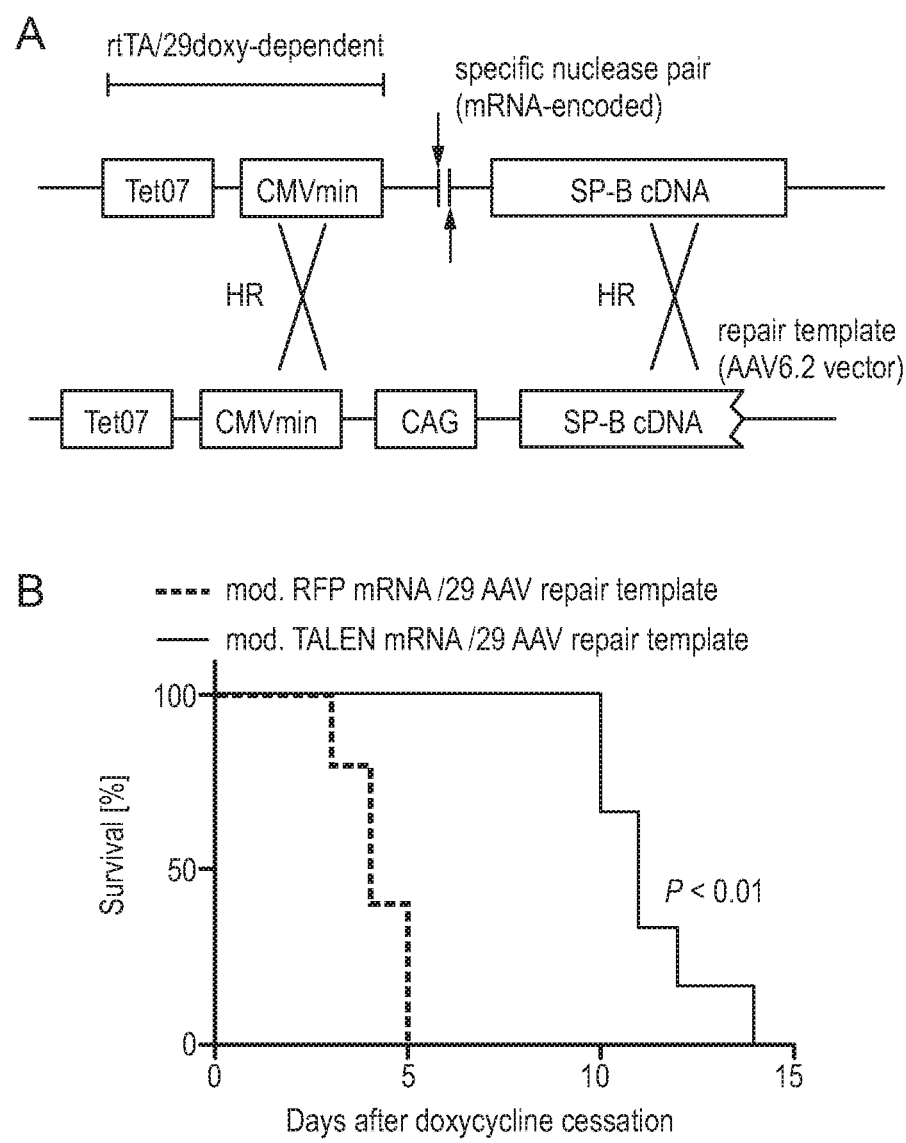
FIG. 3 shows the in vivo gene correction at the SP-B locus of a SP-B knockout mouse by means of a nec-mRNA and the resulting increase of the life span of the mouse.

To this end, the inventors designed an mRNA encoding a TALEN pair which is specific for the SP-B locus. Furthermore, a repair template was designed which is encoded by an adeno-associated viral vector (AAV). It comprises a constitutive promoter upstream of the SP-B cDNA to make the gene expression independent from doxycycline. The repair template is schematically shown in FIG. 3a. The repair template which carries a fully-functional CAG promoter with $TetO_7$-CMV and a truncated SP-B cDNA as homology arms is integrated into the genome via homologous recombination (HR) to overcome doxycycline dependency.

The nucleotide-modified mRNA (25% s2U/m5C) and the vector-encoded repair template were administered into the lung of the mice via a singular high pressure application. In the following, the delivery of doxycycline was stopped which causes acute respiratory failure in the mice and, as a consequence, determines the life span of the mice. The result is shown in FIG. 3b. It turns out, mice which were treated with a combination of 25% of s2U/m5C modified SP-B locus specific TALEN mRNA and the repair template (n=6) survive significantly longer than the controls; cf. continuous right curve in comparison to the left dotted curve. The controls were treated with a corresponding nucleotide modified mRNA which encodes the read fluorescent protein (RFP) (n=5, Kaplan Meier survival curves, Wilcoxon-Gehan test).

4. TALEN-Encoding Nucleotide-Modified mRNA Induces Homology-Directed Repair In Vitro In a further experiment it should be examined whether and to which extent a replacement or a correction of the genetic alteration on the DNA can be obtained. For this purpose, the DNA of SP-B fibroblasts was cleaved by TALEN, encoded by modified mRNA, and a repair template with a NheI restriction site was introduced. In the following, the extent of the homologous recombination was measured. The result is shown in FIG. 4. It becomes evident that a homologous recombination of 31% was reached which demonstrates the suitability of the combination of nec-mRNA and repair template according to the invention.

5. Material and Methods

Figure 7:
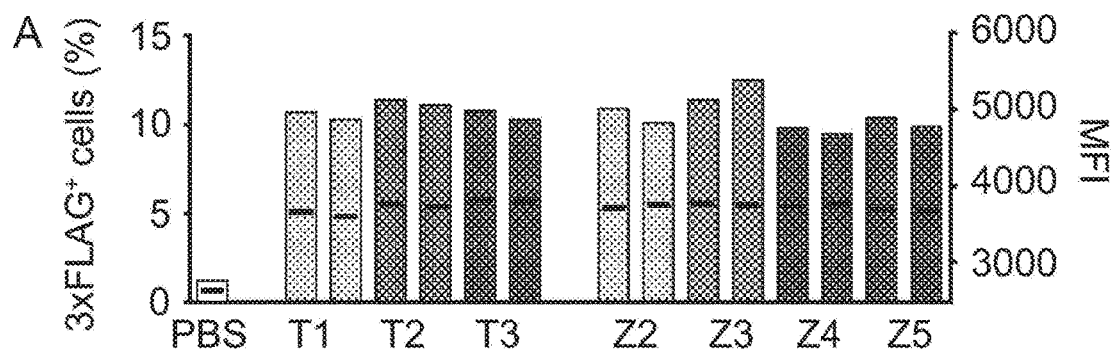
FIG. 7 Expression of FLAG-tagged TALENs and ZFNs in MLE12 cells. a, MLE12 cells (murine ATII cells) were transfected with 1 µg of each TALEN and ZFN plasmid (left bar=left TALEN/ZFN, right bar=right TALEN/ZFN) or untransfected (control). After 24 h the expression was determined by flow cytometry. Transfection efficiency (% 3xFLAG expression, left y axis) and median fluorescence intensity (right axis, blue lines) from three pooled samples each are shown. b, Representative FACS dot plots of MLE12 cells expressing 3xFLAG. MLE12 cells were transfected with plasmids encoding for TALEN (T) 1, 2, 3, and ZFN (Z) 2, 3, 4 and 5. L, left arm. R, right arm. All assays were performed in biological triplicates.
Figure 7:
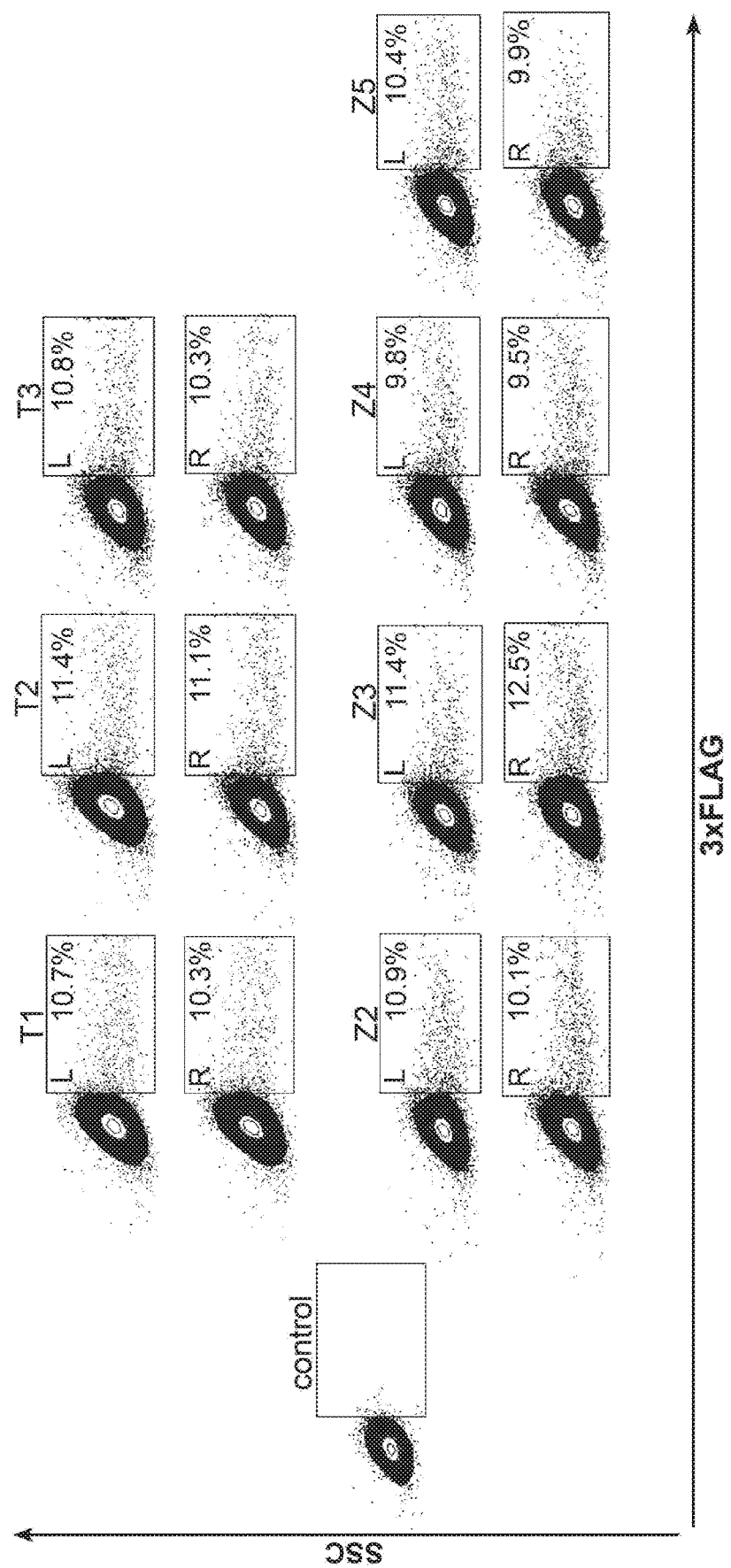

TALEN and ZFN reagents. TALENs and ZFNs targeting the transgenic SP-B cassette were screened by Dual Luciferase Single Strand Annealing Assay (DLSSA) and assembled using an archive of zinc-finger proteins, as previously described; Urnov, F.D. et al. *Nature* 435, 646-651 (2005). The full amino acid sequences of the Z3 pair are shown in FIG. 7. The ZFN expression vector was assembled as previously described; Doyon, Y. et al. Nat Biotechnol 26, 702-708 (2008).

Dual Luciferase Single Strand Assay (DLSSA). ZFNs were screened using a luciferase-based reporter system. This reporter-based assay system is composed of four mammalian expression vectors each under the control of the cytomegalovirus (CMV) immediate early promoter. The vectors are (1) ZFN1, (2) ZFN2, (3) pDLSSA-Firefly, and (4) pDLSSA-Renilla. pDLSSA-Firefly vector contains a Firefly luciferase gene derived from the pGL3-Promoter vector (www.promega.com) with an internal ~600 bp duplication of the middle part of the Firefly luciferase gene. DNA fragments that contain individual ZFN pair binding sites are inserted between these duplicated regions. pDLSSA-Renilla is derived from pRL-TK (www.promega.com) and expresses the Renilla luciferase gene. One day before transfection, 20,000 mouse Neruo2A cells (www.atcc.org) are seeded in a 96-well plate with Dulbecco's Modified Eagle Medium (DMEM; www.cellgro.com) plus 5 mM L-glutamine and 10% FBS. The four expression vectors described above (6.25 ng each) are co-transfected using Lipofectamine 2000 (Life Technologies). ZFN cleavage of the target plasmid followed by 5' to 3' end resection generates single-stranded DNA from the duplicated portion of the Firefly luciferase gene. Annealing of this complementary DNA and subsequent DNA repair creates an intact Firefly luciferase gene that reports the activity of the test ZFNs. Detection of Renilla luciferase serves as an internal control and allows for normalization of intra-transfection variability. Cells are harvested 24-hours post-transfection and the activities of both Firefly and Renilla luciferase are measured using the Dual-Glo Luciferase System (www.promega.com). ZFN activity is scored as the ratio of Firefly luciferase activity to Renilla luciferase activity.

Targeting vectors. The targeting vector carrying the CAG promoter was assembled from synthetic oligonucleotides (www.lifetechnologies.com) and PCR products, and was verified by sequencing. The NheI RFLP donor plasmid was constructed by removing the CAG promoter from the targeting vector by NheI digestion, leaving a single NheI restriction site, which was used in the RFLP assays.

Cell culture and transfection. For the T7 and HDR assays $1\times10^6$ fibroblasts in 6-well plates were transfected as indicated in the respective figure legends using the Neon electroporation system (www.lifetechnologies.com) with 100 µl tips. The electroporation settings were 1,650 Volts, 20 ms, 1 pulse. A549 cells (human ATII cells, the cell type responsible for SP-B expression in the lungs) were maintained at 37° C. under 5% $CO_2$ and grown in minimal essential medium (www.lifetechnologies.com), supplemented with 10% FCS, 1% penicillin-streptomycin. One day before transfection, 50,000 or 80,000 cells/well/500 µl were plated in 24-well plates. The cells (70-90% confluent) were transfected with 5 µg (T7 assays, fragment analyses and RFLP) or 1 µg Z3 pair nec-mRNA (time-course experiment) using Neon electroporation (www.lifetechnologies.com) with a transfection mix volume of 100 µl according to manufacturer's instructions or transduced with MOI of $1\times10^5$ v.g. of each Z3 AAV6. For transfection experiments demonstrated in FIG. 6d, we equilibrated the DNA amounts by adding inert (empty vector) DNA to a total of 9 µg each. For transduction, the cells were washed once with PBS and cultured in Opti-MEM; 6 h after transduction 10% FCS was supplied. After 24 h the medium was removed, the cells washed once with PBS and fresh culture medium was added. Primary fibroblasts from transgenic SP-B mice were obtained by removing the dorsal skin, followed by separation of epidermis from the dermis using dispase. After further digestion of the dermis using collagenase, the suspension was passaged through a 70 µm strainer. After wash and centrifugation steps, the cell pellet was resuspended in fibroblast culture medium (DMEM/Ham's F-12 medium with L-glutamine, 10% MSC grade Fetal Calf Serum, 1× MEM non-essential amino acids, 1× sodium pyruvate, 1% penicillin/streptomycin, 0.1 mM 2-mercaptoethanol). For the time course experiments: after 1, 2, 3, 4, 5, and 14 days after transfection the A549 cells were harvested, permeabilized using BD Cytofix/Cytoperm plus (www.bd.com), stained with APC anti-DYKDDDK clone L5 (www.biolegend.com) antibody, and analysed on an LSR-I flow cytometer (www.bd.com) and data were analysed with BD FACS-Diva software (www.bd.com).

Generation of (nec-)mRNA. To generate templates for in vitro transcription the 3xFLAG-tagged T1 and Z3 were cut out of their original vectors and subcloned into a PolyA-120 containing pVAX1 (www.lifetechnologies.com). The plasmids were linearized with XbaI and transcribed in vitro using the MEGAscript T7 Transcription kit (www.lifetechnologies.com), incorporating 25% 2-thio-UTP and 25% 5-methyl-CTP or 100% PseudoUTP and 100% 5-methyl-CTP (all from www.trilink.com). The anti reverse CAP analog (ARCA) capped synthesized nec-mRNAs were purified using the MEGAclear kit (www.lifetechnologies.com) and analyzed for size on agarose gels and for purity and concentration on a NanoPhotometer (www.implen.com).

T7 nuclease assay. Genomic DNA was extracted from fibroblasts using the DNeasy Blood & Tissue Kit (www.qiagen.com). A 50 µl PCR reaction was set up using 100 ng of gDNA derived from fibroblasts previously transfected with 5 µg T1 or Z3 pair, 0.5 µM primers (for T1: fwd, GTAGGCGTGTACGGTGGGAG [SEQ ID No. 1]; rev, CAGCAGAGGGTAGGAAGCAGC [SEQ ID No. 2]; for Z3: fwd, TGTACGGTGGGAGGCCTAT [SEQ ID No. 3]; rev, CCTGGCAGGTGATGTGG [SEQ ID No. 4]), and AmpliTaq Gold 360 Mastermix (www.lifetechnologies.com). Another PCR reaction was performed using the same primer sets, but with gDNA from untransfected cells. The PCR products were run on agarose gels to verify size and sufficient amplification, pooled, purified by ethanol precipitation, dissolved in 20 µl water and the DNA concentration was measured on a NanoPhotometer. 2 µl NEBuffer 2 (www.neb.com), 2 µg purified PCR product and water were brought to a total volume of 19 µl. The DNA was hybridized in a thermocycler according to the following protocol: 95° C. for 5 min, 95-85° C. at −2° C./sec, 85-25° C. at −0.1° C./sec, hold at 4° C. 1 µl (10 U) of T7E1 (www.neb.com, M0302L) was added and incubated at 37° C. for 15 min. The reaction was stopped by adding 2 µl of 0.25 M EDTA. The reaction was again purified by ethanol precipitation and dissolved in 15 µl water. The nuclease specific cleavage products were determined on agarose gels. The band intensities were quantified using ImageJ (http://rsb.info.nih.gov/ij/).

For measuring off-target effects, A549 cells were transfected 5 µg mRNA or transduced with 1×10$^5$v.g. AAV6-Z3. PCR and T7 was performed as described above (primers: off-target 1: fwd, GCAAGTTTGGCGTCGCTCCA [SEQ ID No. 5]; rev, AGAGGAAGGCGCGGCAGG [SEQ ID No. 6]; off-target 2: fwd, TTCTTGCTCCAGTGACTCTCTTA [SEQ ID No. 7]; rev, AGCCTAGTAAAGACAACACTAGTG [SEQ ID No. 8]; off-target 3: fwd, CAACGTGACCTGCGAGCG [SEQ ID No. 9]; rev, GTGCACGCTCCACTTCTCG [SEQ ID No. 10]; off-target 4: fwd, CTGGAGATGCATCCTTGTCTGT [SEQ ID No. 11]; rev, GAGGGTGAAGACTTTTGGAGCT [SEQ ID No. 12]; off-target 5: fwd, CAGCACCAGATGTTCCCTGTTA [SEQ ID No. 13]; rev, TGGAAAGCAATAGTTCTAGGATGA [SEQ ID No. 14]).

HDR/RFLP assay. Genomic DNA was extracted from fibroblasts or lung tissue using the DNeasy Blood & Tissue Kit (www.qiagen.com). T1 or Z3 target loci were amplified by PCR (40 cycles, 58° C. annealing and 30s elongation at 72° C.; 5 min at 72° C. to assure completion of amplicons) using 0.5 µM of primers P1 (CCTGGCAGGTGATGTGG [SEQ ID No. 15]) and P3 (TGTACGGTGGGAGGCCTAT [SEQ ID No. 16]) with AmpliTaq Gold 360 Mastermix. In addition, in-out PCR reactions were performed using primers P1 and P2 (AGGCACTGGGCAGGTAAGTA [SEQ ID No. 17]).

Flow Cytometry. Harvested lungs were digested at 37° C. for 1 hour on a rotating shaker in 1 mg/ml collagenase type I (www.lifetechnologies.com), 1% (500 U) DNase (www.epibio.com) solution. Digested lung was passed through a 40-µm nylon cell strainer and erythrocytes were lysed using ACK Lysing Buffer (www.lifetechnologies.com). PE anti-CD45 clone 30-F11, PE anti-CD31 clone C13.3, APC anti-mouse Ly-6A (Sca-1) clone D7 (www.biolegend.com), FITC anti-FLAG M2 and anti-clara cell secretory protein (www.sigmaaldrich.com) were used to stain lung cells. After staining for extracellular markers, cells were fixed and permeabilized using BD Cytofix/Cytoperm plus (www.bd.com), then stained with intracellular antibodies. Flow cytometer analyses were performed on a LSR-I flow cytometer (www.bd.com) and data were analysed with BD FACS-Diva software (www.bd.com). ATII and Clara cells sorting were performed with a FACSAria (www.bd.com).

Nanoparticles. Chitosan (83% deacetylated (Protasan UP CL 113, www.novamatrix.biz)) coated PLGA (Poly-d,l-lactide-co-glycolide 75:25 (Resomer RG 752H, www.evonik.de) nanoparticles (short: NPs) were prepared by using emulsion-diffusion-evaporation15 with minor changes. In brief, 100 mg PLGA was dissolve in ethyl acetate and added dropwise to an aqueous 2.5% PVA solution (Polyvinyl alcohol, Mowiol 4-88, www.kuraray.eu) containing 15 mg Chitosan. This emulsion was stirred (1.5 h at RT) and followed by homogenization at 17,000 rpm for 10 min using a Polytron PT 2500E (www.kinematica.ch). These positive charged NPs were sterile filtered and characterized by Malvern ZetasizerNano ZSP (hydrodynamic diameter: 157.3±0.87 nm, PDI 0.11, zeta potential +30.8±0.115 mV). After particle formation they were loaded with mRNA by mixing (weight ratio: 25:1).

Transgenic SP-B cassette, mRNA templates and AAVs. AAV serotype 6 vectors from the Z3 pair and the donor sequence were produced and purchased from Virovek (www.virovek.com). The sequence information can be retrieved from the Sequence Listing at SEQ ID nos. 24-34 and from FIG. 14.

Transgenic SP-B cassette (before gene manipulation): the sequence at nucleotide positions 427-450 of SEQ ID no. 24 is deleted when transgene integration occurs.

AAV6_CAG_SP-B_donor: 5' AAV ITR: 3933-4051 (119 bp); ZFN3-repair-template: 4087-6074 (1988 bp); 3' AAV ITR: 6112-6241 (130 bp)

AAV6-ZFN 3-LEFT: 5' AAV ITR: 3933-4051 (119 bp); CMV Promoter: 4060-4638 (579 bp); 3Flag-NLS-38561-Fok-KKR: 4844-5992 (1149 bp); bGHpA: 5999-6223 (225 bp); 3' AAV ITR: 6240-6369 (130 bp).

AAV6-ZFN 3-RIGHT: 5' AAV ITR: 3933-4051 (119 bp); CMV Promoter: 4060-4638 (579 bp); 3Flag-NLS-38558-Fok-ELD: 4766-6031 (1266 bp); bGHpA: 6038-6262 (225 bp); 3' AAV ITR: 6279-408 (130 bp).

Animal experiments. 6-8 week old BALB/c mice (www.criver.com) and transgenic SP-B mice6 [SP-C rtTA/(teto)$_7$ SP-B/SP-B$^{-/-}$] were maintained under specific pathogen-free conditions and were kept with a 12 h/12 h light/dark cycle. All animals were provided with food and water ad libitum, and were acclimatized for at least 7 d before the start of the respective experiment. Transgenic SP-B mice were fed with doxycycline containing food until cessation (day 0 of the control and main groups). All animal procedures were approved and controlled by the local ethics committee and carried out according to the German law of protection of animal life.

Intratracheal injection. BALB/c or transgenic SP-B mice were anesthetized intraperitoneally with a mixture of medetomidine (0.5 mg/kg), midazolam (5 mg/kg) and fentanyl (50 µg/kg), and suspended on a mouse intubation platform (www.penncentury.com, Model MIP) at a 45° angle by the upper teeth. A small animal laryngoscope (www.penncentury.com) was used to provide optimal illumination of the trachea. A Microsprayer Aerosolizer—Model IA-1C connected to a FMJ-250 High Pressure Syringe (both from www.penncentury.com) was endotracheally inserted and PBS, 20 µg Z3 (nec-)mRNA naked or complexed with Nanoparticles or AAV6 (www.virovek.com) (was applied in a volume of 100 μl. The Microsprayer tip was withdrawn after 10 s, antidot was injected subcutaneously (atipamezol (50 μg/kg), flumazenil (10 μg/kg) and naloxon (24 μg/kg)), and the mouse was taken off the support after 2 min.

Airway compliance. Compliance was determined by using the ex vivo model of the isolated perfused lung as described previously (IPL, Harvard Apparatus). In short, in situ mouse lungs were placed in a thorax chamber and mice were ventilated via a tracheal cannula. Ventilation rate was set to 90 breaths per minute with negative pressure ventilation between −2.8 cm $H_2O$ and 8.5 cm $H_2O$. To prevent atelectasis a hyperinflation was triggered every 5 minutes (−25 cm $H_2O$). Perfusion of lungs was done with a 4% hydroxyethyl starch containing perfusion buffer via the pulmonary artery (flow 1 ml/min). Lung function parameters were recorded automatically and compliance calculated by HSE-HA Pulmodyn W Software (Harvard Apparatus). For graphical and statistical analysis, the mean compliance values were calculated from the last 10 timestamps (40 sec) of each 5-minute period (between two hyperinflations).

Airway resistance. Airway resistance in response to methacholine (MCh, acetyl-β-methylcholine chloride; Sigma-Aldrich) was again determined using the ex vivo model of the isolated perfused lung (IPL, Harvard Apparatus). In brief, after a 20-minutes baseline measurement, lungs were perfused with increasing concentrations of MCh (0.1 pM, 1 μM, 10 μM, and 100 μM) for 10 minutes each, separated by a 10-minute washout period with perfusion buffer. Lung function parameters were recorded automatically and airway resistance was recorded by HSE-HA Pulmodyn W Software (Harvard Apparatus). For graphical and statistical analysis, the mean resistance values were calculated from the last 10 timestamps (40 sec) of each 10-minute MCh exposure.

Histopathology. Mouse lungs were fixed in 4.5% Histofix (www.carlroth.com) at 4° C. overnight. Fixed lungs were embedded in paraffin, and slices were stained with either H&E or Surfactant Protein-B DAB (mouse monoclonal anti-SP-B antibody (www.abcam.com, ab3282), Zytochem Plus HRP One-Step Polymer anti-mouse/rabbit/rat (www.zytomed.com, ZUC53-006) and DAB substrate kit for peroxidase (www.vectorlabs.com, SK-4100). 3xFLAG FITC fluorescence staining (monoclonal anti-FLAG M2-FITC antibody (www.sigma-aldrich.com, F4049) and DAPI counterstaining (www.applichem.com, A1001) was examined using a Zeiss Axio Imager. For 3xFLAG Cy3 fluorescence staining, rabbit polyclonal to DDDDK tag antibody (www.abcam.com, ab21536) was used as primary antibody and goat anti rabbit Cy3 antibody (www.jackson-immuno.com, 111-165-144) was used as secondary antibody together with DAPI (www.applichem.com, A1001).

Western Blot. Protein from BALF was separated on NuPAGE 10% Bis-Tris Plus gels and a NuPAGE Mini Gel Tank (all from www.lifetechnologies.com), and immunoblotting was performed by standard procedures according to manufacturer's instructions using the XCell II Mini-Cell and blot modules (www.lifetechnologies.com). After blocking for 2 hours at room temperature, primary antibody against SP-B (kindly provided by Prof. Griese, Munich) or ANTI-FLAG M2 (www.sigmaaldrich.com) was incubated overnight, HRP-conjugated secondary antibodies (anti rabbit from www.dianova.com) were incubated for 1 hour. Blots were processed by using ECL Prime Western Blot Detection Reagents (www.gelifesciences.com). Semiquantitative analysis was performed with the Quantity One software (www.bio-rad.de).

Target-site sequencing. Genomic DNA from primary fibroblasts (in vitro transfected/transduced) or sorted ATII cells (after in vivo transfection/transduction) was isolated using the NucleoSpin Tissue Kit (www.mn-net.com) according to the manufacturer's protocol. Amplicons were derived from PCR with Primers P1 and P2 (sequences see above) using the following conditions: AmpliTaq Gold 360 master mix (www.lifetechnologies.com) at 95° C. for 10 min, 95° C. for 30 sec, 60° C. for 30 sec., 72° C. for 60 sec, with in total 35 cycles and a final extension step at 72° C. for 7 min. The amplicons were cloned into the pCR-TOPO vector (www.lifetechnologies.com) and sequenced using the primers M13forward (GTAAAACGACGGCCAGTG [SEQ ID No. 18]) and M13reverse (CAGGAAACAGCTATGAC-CATG [SEQ ID No. 19]). The alignments have been performed with Geneious R6 (www.biomatters.com) using the "multiple align" function, choosing a cost matrix of 65% similarity (5.0/−4.0), a gap open penalty of 12 and a gap extension penalty of 3.

RealTime RT PCR. The lung cell separations were washed vigorously three times with PBS to avoid carrying over RNA not taken up by lung cells (the third supernatant was later tested for RNA contamination using the qPCR procedure described below). RNA was then isolated with the RNeasy purification kit (www.qiagen.com). Reverse transcription of 50 ng RNA was carried out using iScript cDNA synthesis kit (www.bio-rad.com). Detection of Z3 cDNA was performed by SYBR-Green based quantitative Real-Time PCR in 20 μl reactions on a ViiA7 (www.lifetechnologies.com). Reactions were incubated for 10 min at 95° C., followed by 40 cycles of 15 sec at 95° C. and 2 min at 50° C. (annealing and extension), followed by standard melting curve analysis. The following primer pairs were used: Z3 left fwd: TGTACGGCTACAGGGGAA [SEQ ID No. 20], Z3 left rev GCCGATAGGCAGATTGTA [SEQ ID No. 21]; optimal determined house-keeping gene beta-actin: fwd TAGGCACCAGGGTGATG [SEQ ID No. 22], rev GCCATGTTCAATGGGGTACT [SEQ ID No. 23].

Statistics. Differences in mRNA expression between groups were analyzed by pair-wise fixed reallocation randomization tests with REST 2009 software17. All other analyses were performed using the Wilcoxon-Mann-Whitney test with SPSS 21 (www.ibm.com). Data are presented as mean±s.e.m. or as the median±IQR (interquartile ranges) and P<0.05 (two-tailed) was considered statistically significant. For survival studies Log-rank tests were performed. Statistics for lung compliance was performed using 2way ANOVA with Bonferroni-post tests with GraphPad Prism 5.0 software. Lung function data are presented as mean±s.d. and P<0.05 (two-tailed) was considered statistically significant. No randomization was used for animal experiments. In all cases but at administration of AAV6/mRNA i.t., the investigators were blinded when assessing outcomes.

6. Results

Nuclease-mediated genome editing holds enormous potential to knockout unwanted genes or repair disease-causing mutations. An ideal nuclease delivery vehicle is (i) short-lived, (ii) non-integrating, and (iii) able to enter target cells efficiently. A variety of vectors have been utilized to deliver nuclease pairs, however, to date, none have achieved direct in vivo gene correction while simultaneously being transient and non-integrating.

The inventors have used modified mRNA as an alternative to traditional viral vectors, one which naturally avoids genomic integration and provides a transient pulse of protein expression. By using nucleotide-modified mRNA, the inventors reached therapeutic protein expression levels in vivo in mouse models of surfactant protein B (SP-B) deficiency and experimental asthma. Here, the inventors utilize modified mRNA to deliver site-specific nucleases to the lung to demonstrate the value of "nec-mRNA" as a tool for in vivo genome editing.

Figure 5:
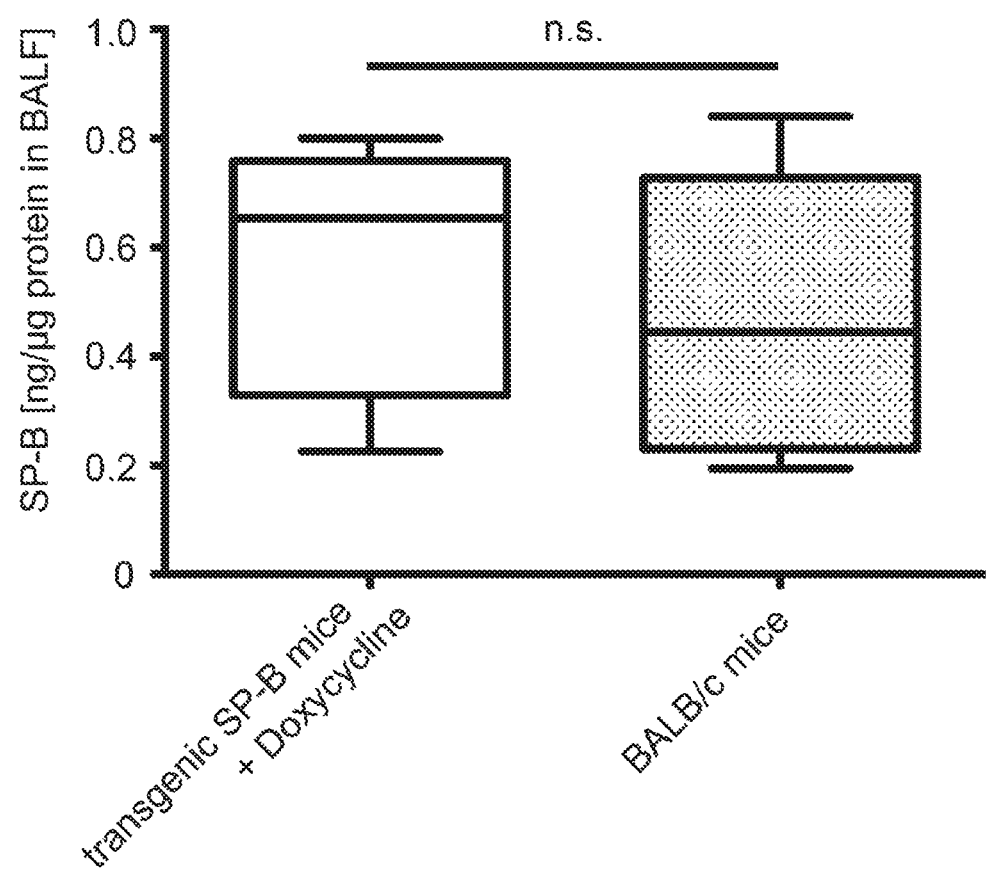
FIG. 5 SP-B expression in lung BALF. The difference in SP-B expression levels per µg total protein in BALF between transgenic SP-B mice on Doxycycline and BALB/c mice was not significant (n.s.). Boxes represent medians±IQRs (interquartile ranges). n=4 mice per group.

To illustrate the effectiveness of nec-mRNA as a nuclease-delivery vehicle, the inventors chose a well-established transgenic mouse model of SP-B deficiency, where SP-B cDNA is under the control of a Tetracycline-inducible promoter. Administration of doxycycline drives SP-B expression levels comparable to those observed in wild-type mice (FIG. 5). Following cessation of doxycycline, this model closely mimics the phenotypic changes seen in the human version of the disease: thickened alveolar walls, heavy cellular infiltration, increased macrophages and neutrophils, interstitial edema, augmented cytokines in the lavage, a significant drop in lung function, and fatal respiratory distress leading to death within days. Here, the inventors insert a constitutive CAG promoter immediately upstream of the SP-B cDNA to allow doxycycline-independent expression and prolonged life in treated mice.

Figure 6:
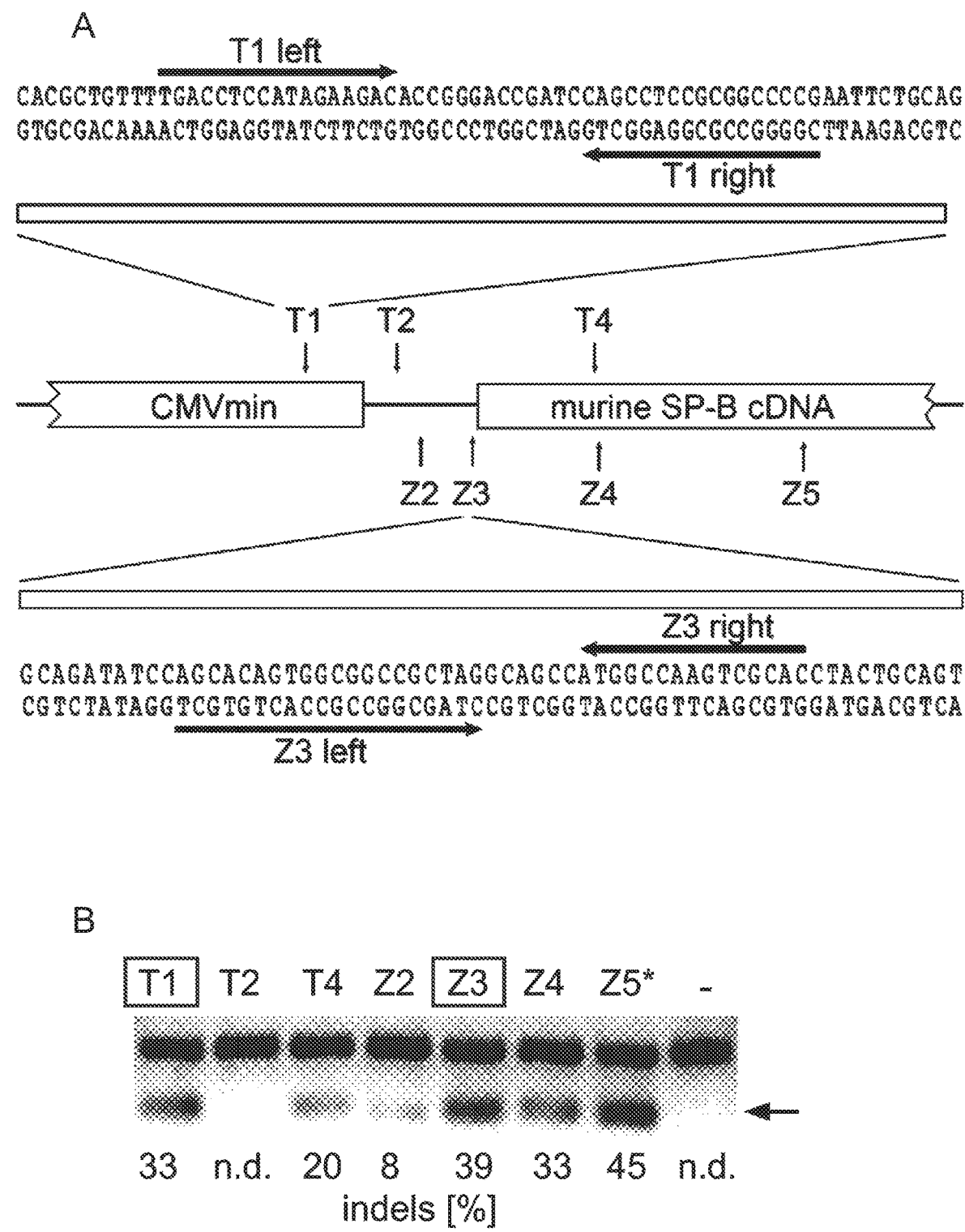
FIG. 6 nec-mRNA cleaves the SP-B cassette, induces HDR in vitro, and is expressed in lung cells in vivo. (a) TALEN and ZFN candidates relative to the transgenic SP-B cassette. Transgenic SP-B mice-derived fibroblasts were used for (b-d); n.d., not detectable. (b) T7 assays to determine the frequency of TALEN- and ZFN-induced indels in genomic DNA harvested 3 d post-transfection (5 µg/cell). (c) T1- and Z3-induced indels following delivery as either mRNA or pDNA (0.5 or 5 µg). (d) Percent HDR 3 d following co-transfection of 5 µg T1 or Z3 mRNA (or pDNA) with 0-4 µg donor plasmid. Arrows denote NheI-sensitive cleavage products resulting from HDR. (e) Time-course showing kinetics and stability of 3xFLAG-tagged Z3 mRNA versus Z3 AAV in A549 cells (n=3). (f) Anti-3xFLAG flow cytometry shows protein expression in total lung cells and ATII cells. Boxes, medians±IQRs; whiskers, minimum and maximum; *, P<0.05 versus unmodified;  and *, P<0.01 and P<0.001 versus no NPs. (g) Immunostaining for 3xFLAG in lung sections from mice described in f. Scale bar, 50 µm. Arrows indicate 3xFLAG expression.
Figure 6:
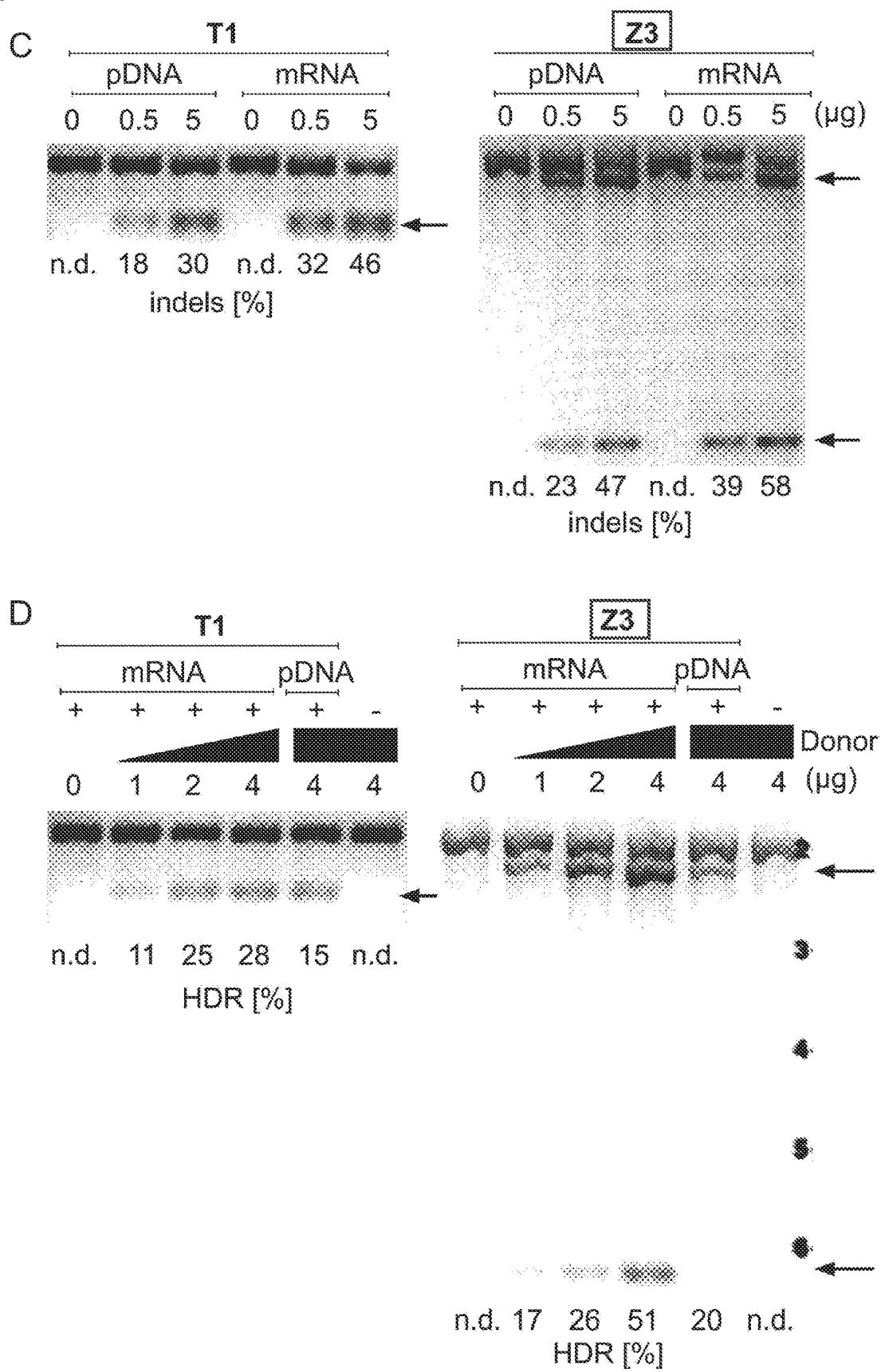
Figure 6:
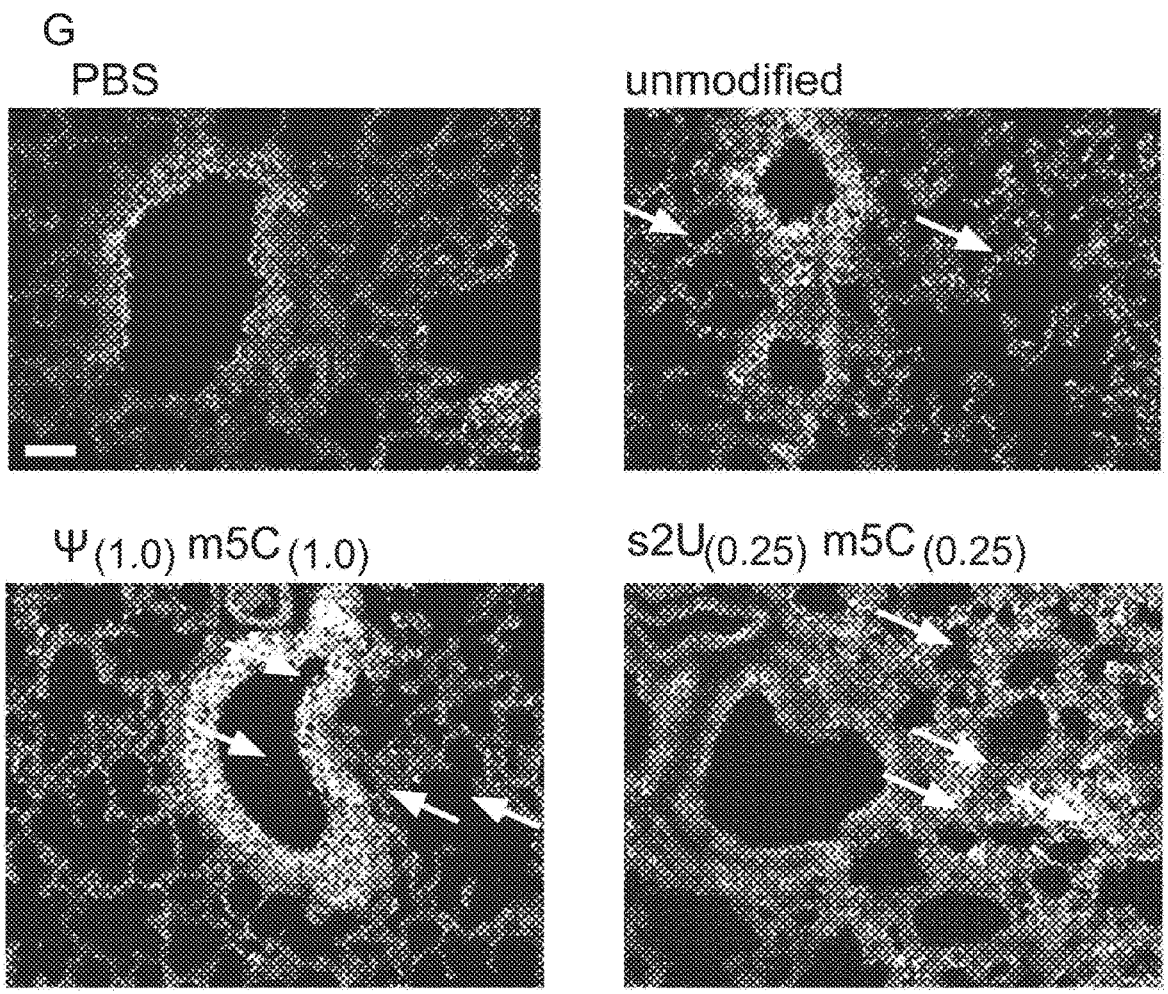
Figure 8:
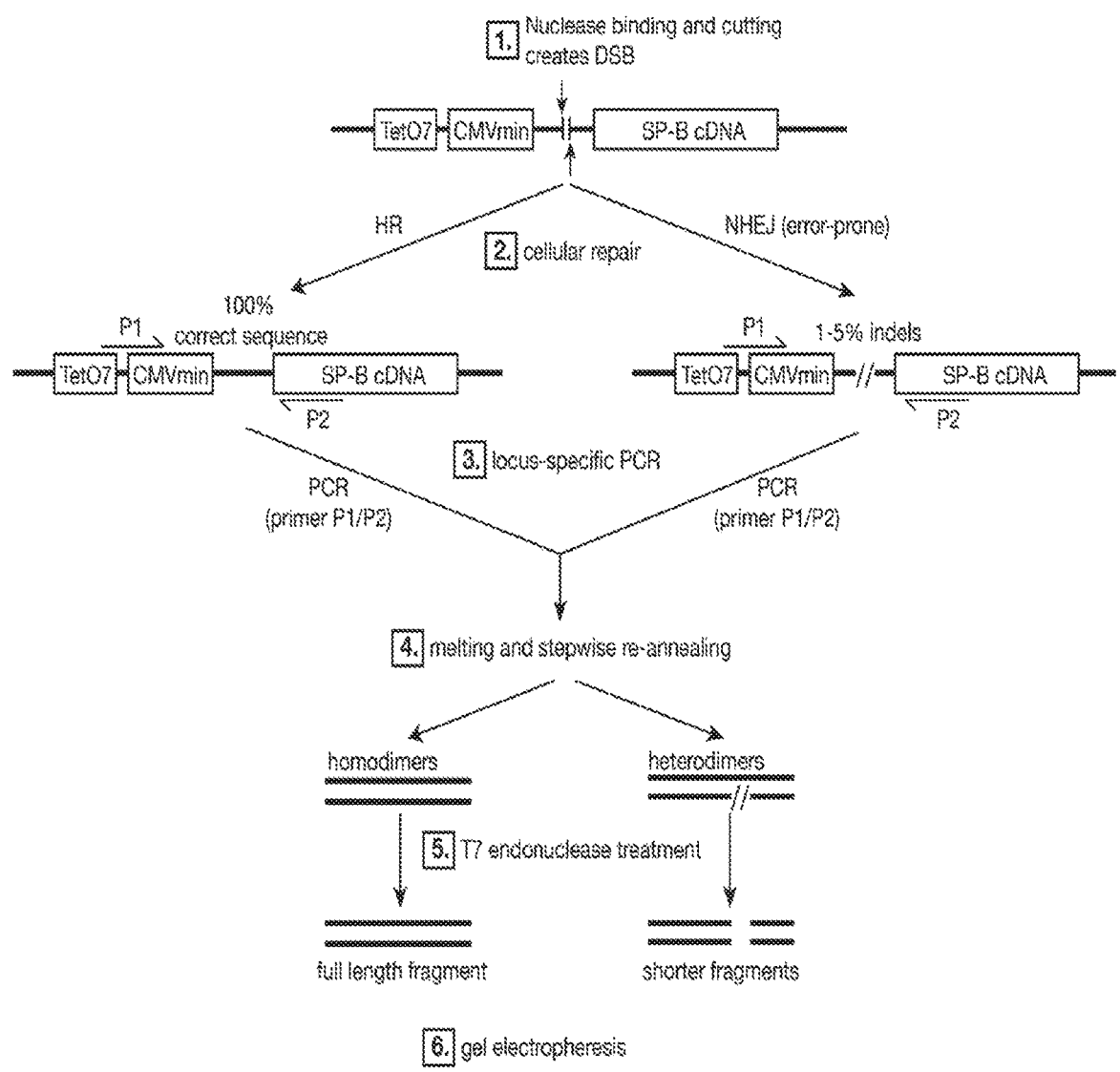
FIG. 8 Schematic of the T7 assay to prove cleavage of the transgenic SP-B promoter region. Fibroblasts from transgenic SP-B mice were transfected with TALEN or ZFN plasmid pairs (5 µg) (1.), leading to cellular repair, with NHEJ leading to approximated 1-5% indels (insertions and/or deletions) (2.). Genomic DNA was harvested 4 d after transfection and a locus-specific PCR was performed (3.). PCR products were melted at 95° C., re-annealed at gradually decreasing temperatures (4.) and treated with T7 endonuclease (5.). T7 endonuclease only cuts heteroduplex at sites of mismatch, resulting in smaller fragments which then can be visualized on agarose gels (6.) to determine the frequency of nuclease-induced indels in the samples.
Figure 9:
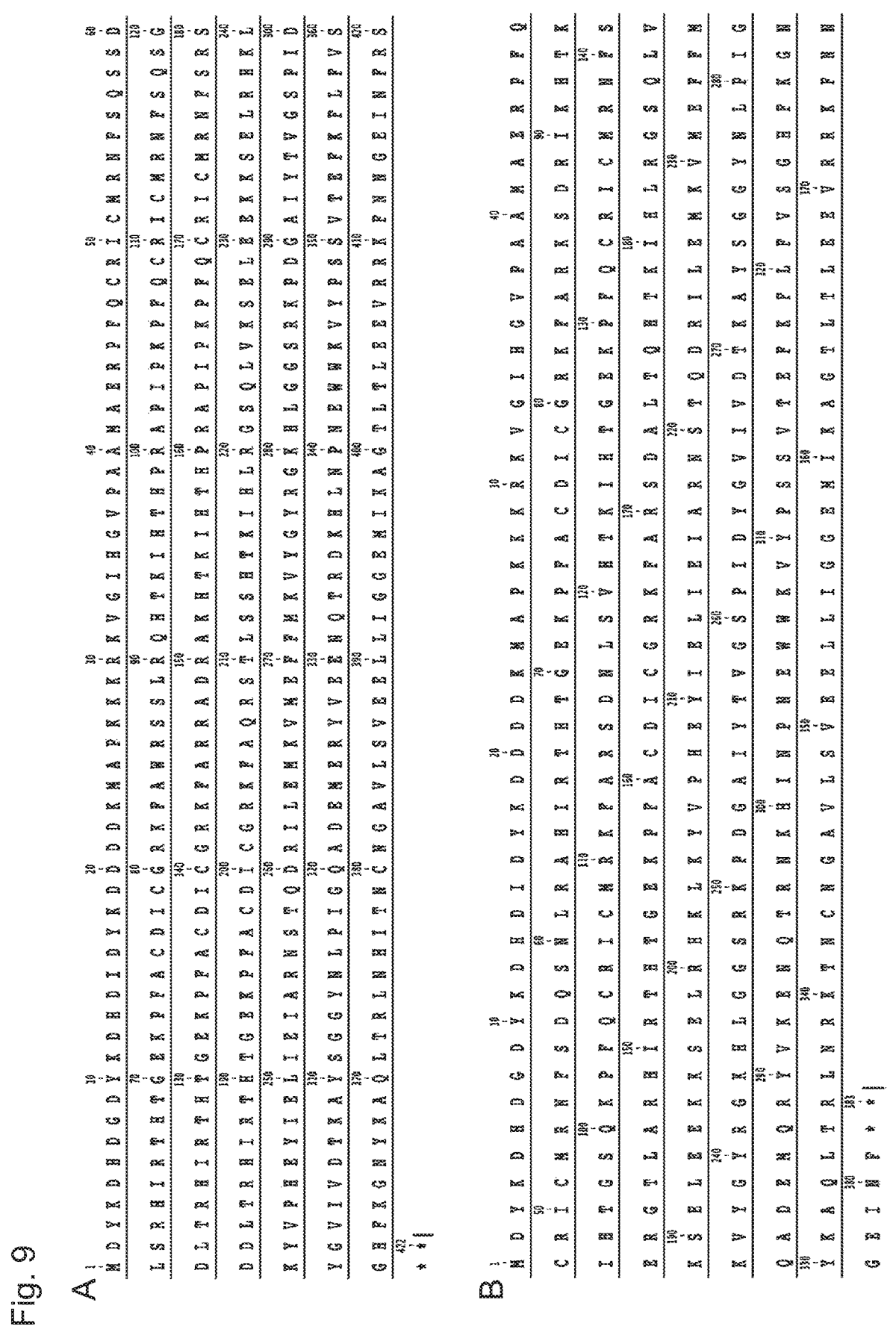

First, a panel of ZFNs and TALENs was customized to target the transgenic SP-B cassette (FIG. 6a and FIG. 7). Due to their high activity and proximity to the desired site of promoter integration, TALEN #1 (T1) and ZFN #3 (Z3) were selected (FIG. 6a,b). In comparison to plasmid DNA, T1 and Z3 delivered as mRNA showed a significant increase in both DSB-induction (FIG. 6c FIG. 8; P<0.05) and homology directed repair (HDR) (FIG. 6d, P<0.05). As Z3 mRNA was more efficient than T1 mRNA in both cases, Z3 was chosen for further experimentation (amino acid sequences in FIG. 9; SEQ ID nos. 35 and 36). Comparison with a Z3-encoding AAV vector ("Z3 AAV") highlights the short-lived expression pattern of Z3 mRNA (FIG. 6e), limiting the time during which off-target cleavage activity could occur.

Figure 10:
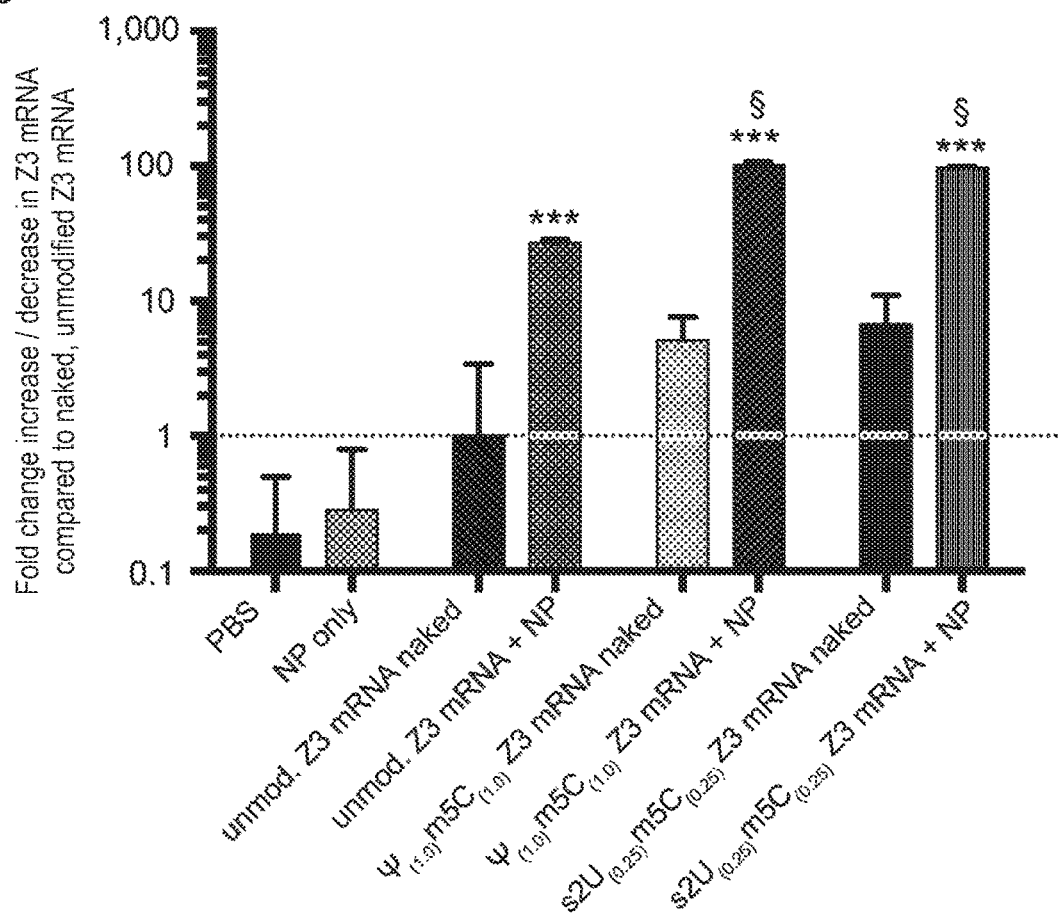
FIG. 10 Z3 nec-mRNA is efficiently deposited in the lung in vivo. 100 µl PBS, 20 µg unmodified Z3 mRNA, or 20 µg Z3 nec-mRNA containing a 5' 3xFLAG tag (naked or complexed with nanoparticles, 100 µl total volume) were i.t. administered to BALB/c mice (n=5 mice per group). After 24 h, total RNA was extracted from lungs, reverse transcribed, and Z3 mRNA was quantified by qPCR. Mean+SD ist shown. ***, P<0.001 versus "unmod. Z3 mRNA naked"; §, P<0.05 versus "unmod. Z3 mRNA+NP".
Figure 11:
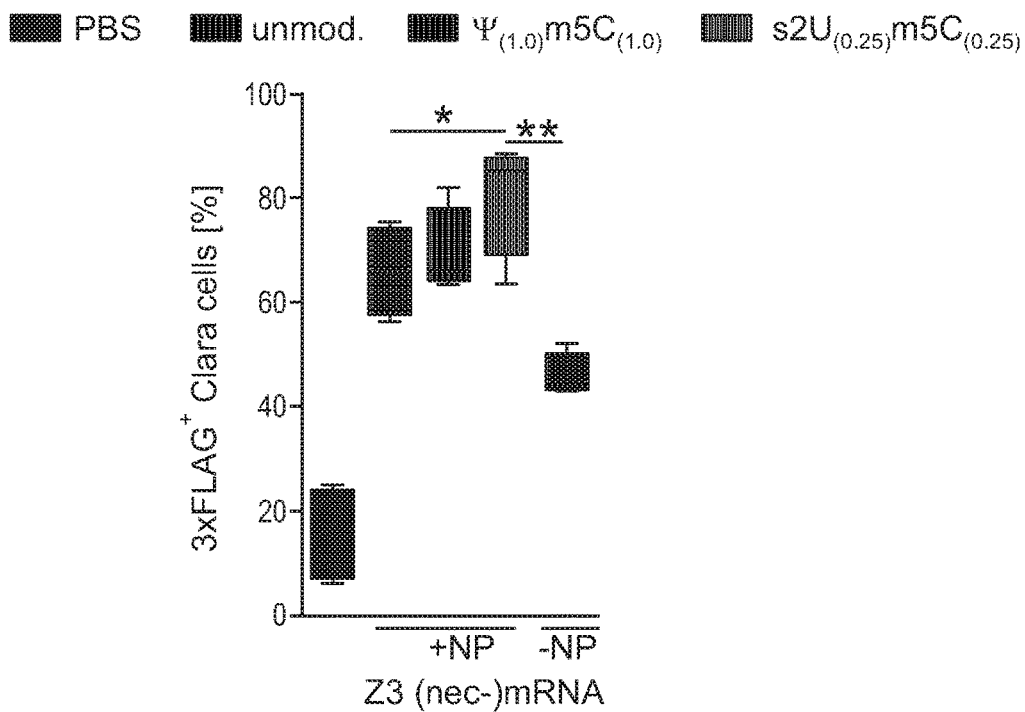
Figure 12:
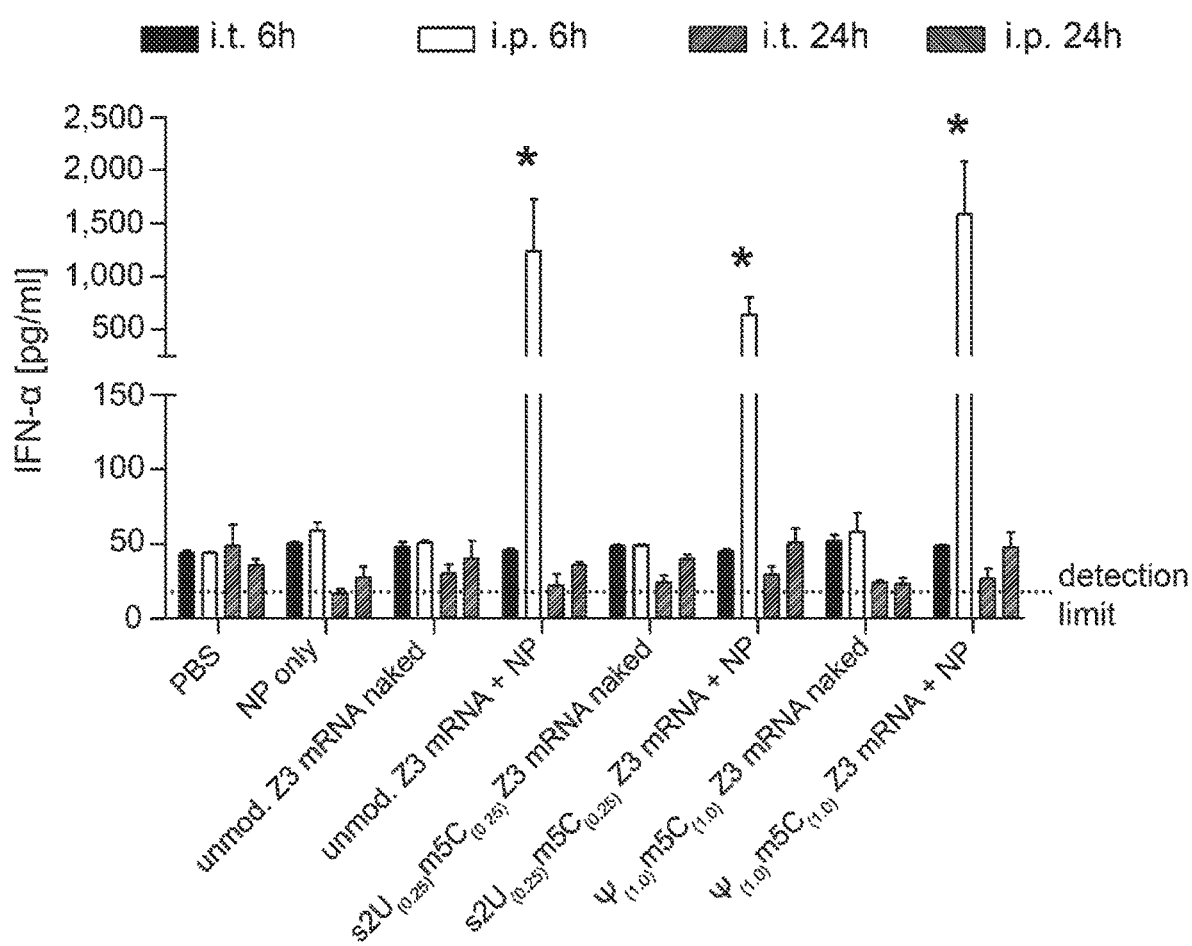
FIG. 12 In vivo immune reaction to nec-mRNA. 1 µg of Z3 mRNA panel i.v. or i.p. injected into mice (n=3 per group). 6 h and 24 h post-injection, IFN-α was measured by ELISA in duplicates. Relative mRNA deposition amounts were determined by RT-qPCR of isolated lung tissue. *, P<0.05 versus "NP only".

To optimize Z3 expression in the lung, the inventors administered a panel of 3xFLAG-tagged Z3 mRNAs with various modification schemes, with or without mRNA-complexation to nanoparticles (NPs); cf. Nafee, N., Taetz, S., Schneider, M., Schaefer, U. F. & Lehr, C. M. Nanomedicine 3, 173-183 (2007). Following intratracheal (i.t.) delivery, NP-complexing significantly increased mRNA expression levels (FIG. 10). 3xFLAG protein expression was most robust for the s2U$_{0.25}$/m5C$_{0.25}$-modified, NP-complexed group (FIG. 6f,g and FIG. 11), and no immune activation was observed following i.t. delivery (FIG. 12). Hence, subsequent in vivo studies utilized i.t. delivery of this candidate, referred to as "Z3 nec-mRNA-NP".

Figure 13:
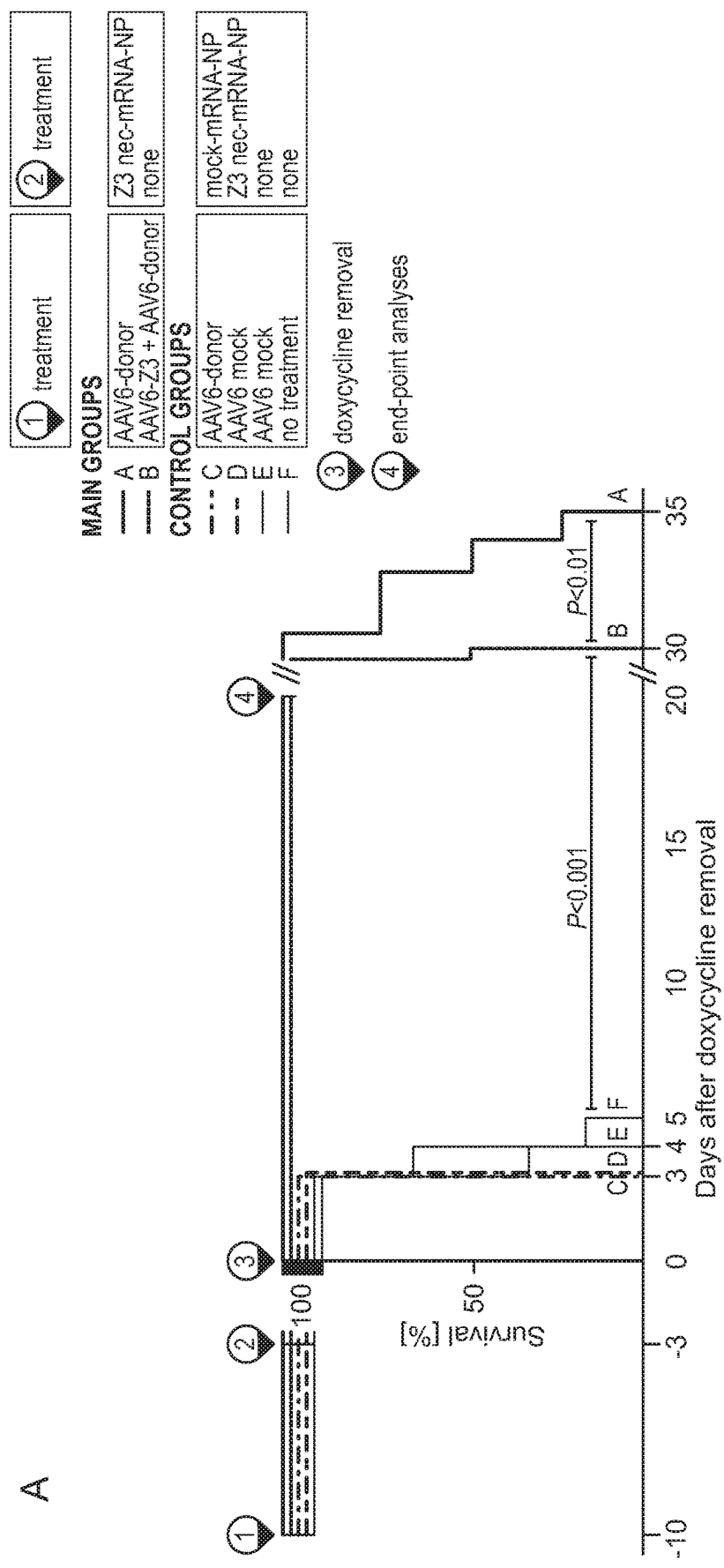
FIG. 13 Rescue of SP-B deficient mice by in vivo gene manipulation. (a) Treatment scheme and Kaplan-Meier survival curves of transgenic SP-B mice treated i.t. with donor ($2.5 \times 10^{11}$ v.g. AAV6-donor, AAV6-mock, or none) and nuclease (20 µg Z3 nec-mRNA-NP, mock-mRNA-NP, $5 \times 10^{10}$ v.g. Z3 AAV, or none), then withdrawn from doxycycline. Groups C-F, n=6; groups A and B, n=13, reduced to n=4 20 d post-doxycycline removal. Log-rank tests were performed. (b,c) Representative SP-B expression (brown) in lung tissue (c) and anti-SP-B blots on cell-free BALF supernatant (10 µg total protein/lane) (c) from mice described in a. Scale bar, 50 µm. Lavages and tissue were harvested 20 days after doxycycline removal. (d) Lung compliance normalized to respective body weight (n=4), 20 d after doxycycline removal. Baseline measurement performed for 20 min; values calculated prior to each hyperinflation. ***, P<0.001 versus groups C-F; §, §§, and §§§, P<0.05, P<0.01, and P<0.001 versus group D. (e,f) PCR on lung-isolated DNA from groups A and B or untargeted lungs; each lane represents an individual mouse. Samples were taken 20 d after doxycycline removal. (e) PCR of the targeted locus followed by T7 assays. Arrows show expected bands. (f) PCR using P1/P3 or P1/P2, followed by gel electrophoresis. #, untargeted control; §, DNA pool of groups A and B. Arrow indicates band resulting from HDR. (g) Schematic of the transgenic SP-B cassette, CAG integration and primer (P1, P2 and P3) locations for in-out PCRs. (h) Representative immunohistochemistry for groups A, B, and a doxycycline-control group (+Doxy) using two different anti-3xFLAG antibodies. Scale bar, 50 µm. Tissue was collected 20 d after doxycycline removal.
Figure 13:
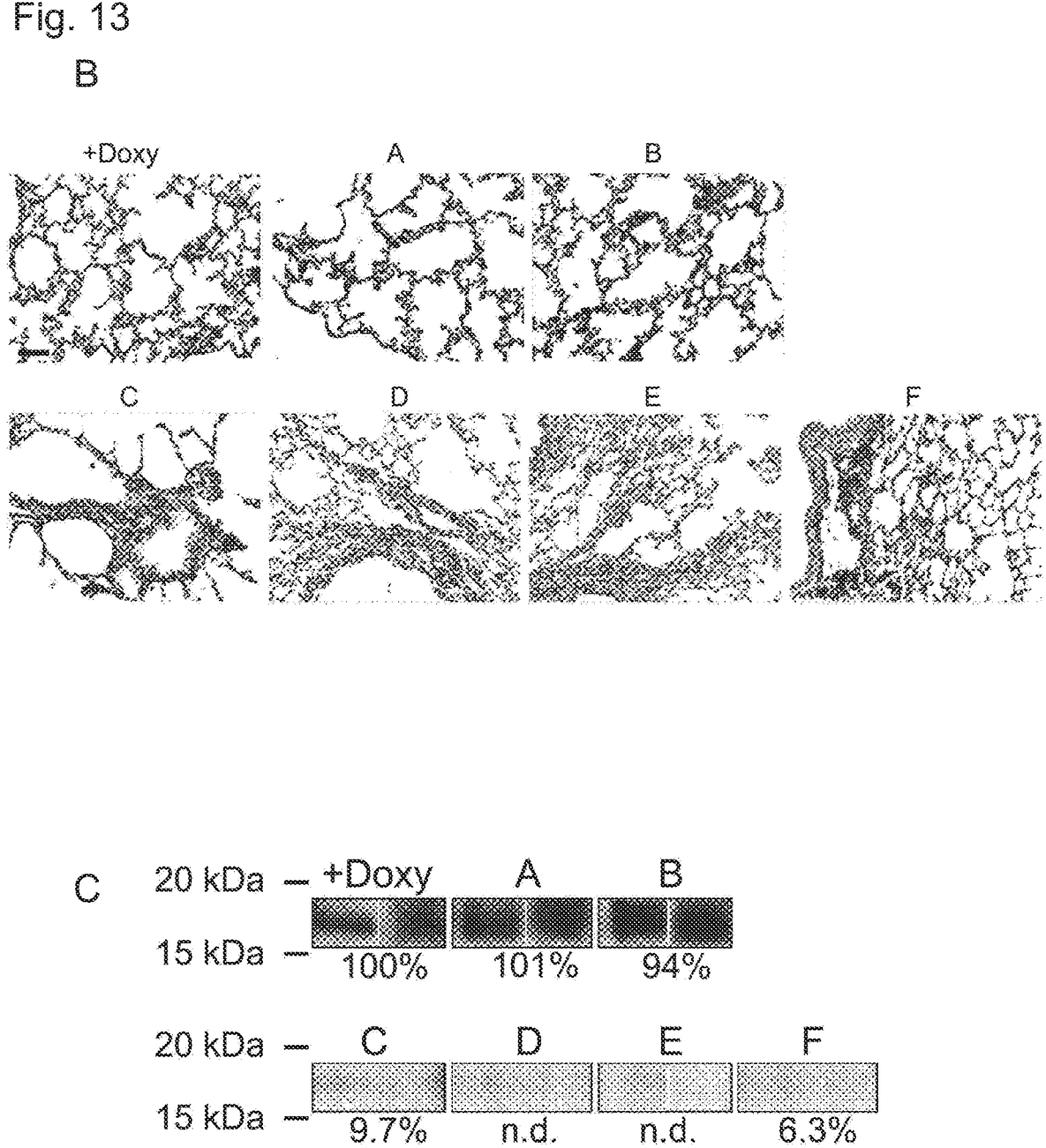
Figure 14:
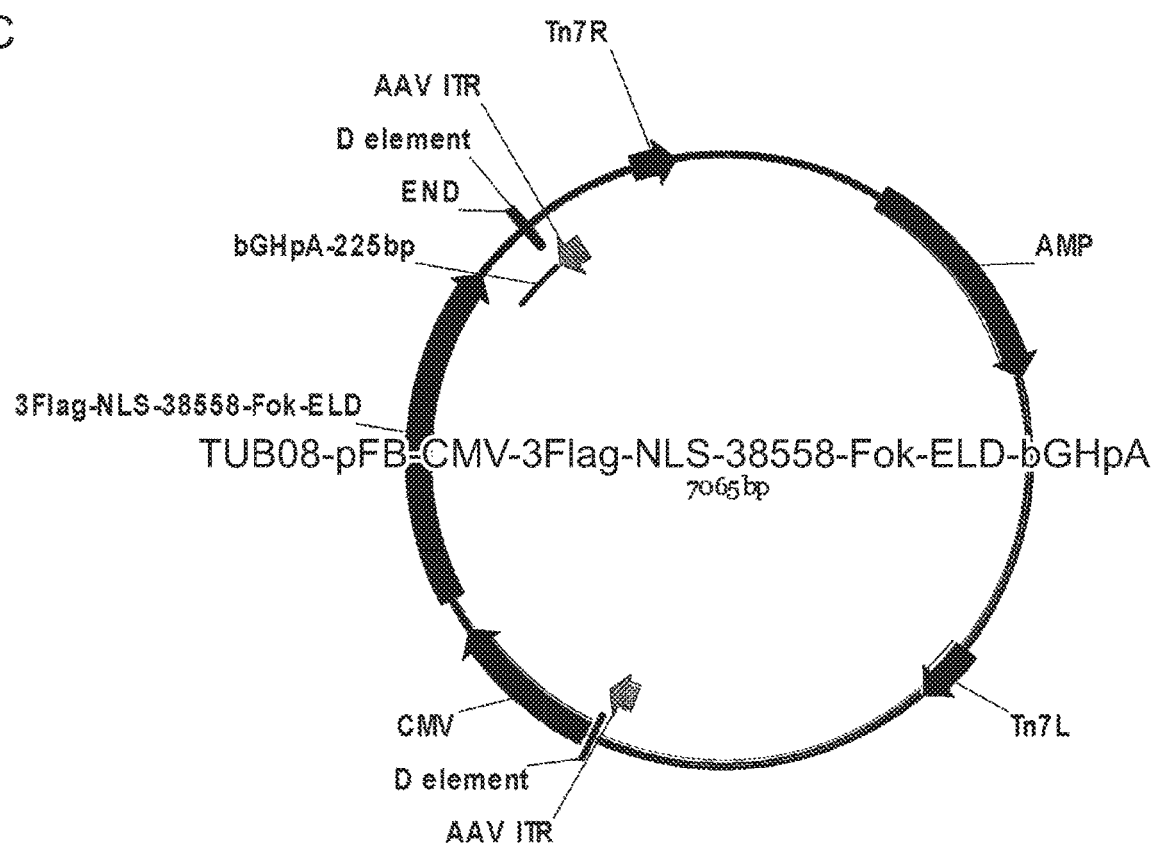
FIG. 14 Structures of TUB07-pFB-ZFN3-repair-template (A), TUB09-pFB-CMV-3Flag-NLS-38561-Fok-KKR-bGHpA (B), and TUB08-pFB-CMV-3Flag-NLS-38558-Fok-ELD-bGHpA (C).
Figure 15:
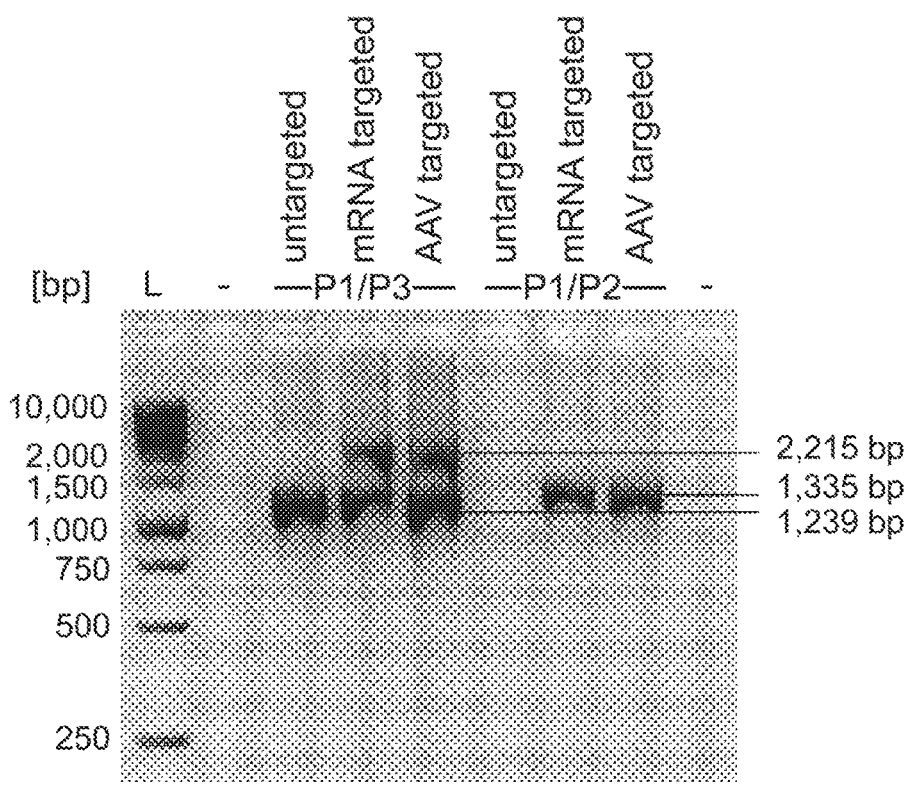
FIG. 15 Ex vivo transgene integration. Fibroblasts, derived from transgenic SP-B mice, were transduced with $2.5 \times 10^5$ v.g. of AAV6-donor and either a mock control ("untargeted"), 2 µg Z3 nec-mRNA ("mRNA targeted") or $1 \times 10^5$ v.g. AAV6-Z3 ("AAV targeted"). L, ladder. Lanes marked with "−" are the respective no-template negative controls. Given are the expected amplicon sizes.

Next, a complementary donor template was designed to insert a constitutive CAG promoter at the Z3 nec-mRNA-NP cut site, upstream of the transgenic SP-B cDNA (FIG. 13g and FIG. 14). Successful site-specific HDR would allow mice to survive and produce SP-B in the absence of doxycycline. As it is critical to deliver the donor template in excess to ensure it is favored over the homologous chromosome during HDR, for this proof-of-principle, the inventors utilized a vector known to transduce lung cells with high efficiency, AAV-serotype 6 (integration-deficient lentiviruses will be tested in future studies). Ex vivo delivery of the AAV6-donor with Z3 nec-mRNA-NP resulted in successful HDR in primary fibroblasts (FIG. 15).

Figure 16:
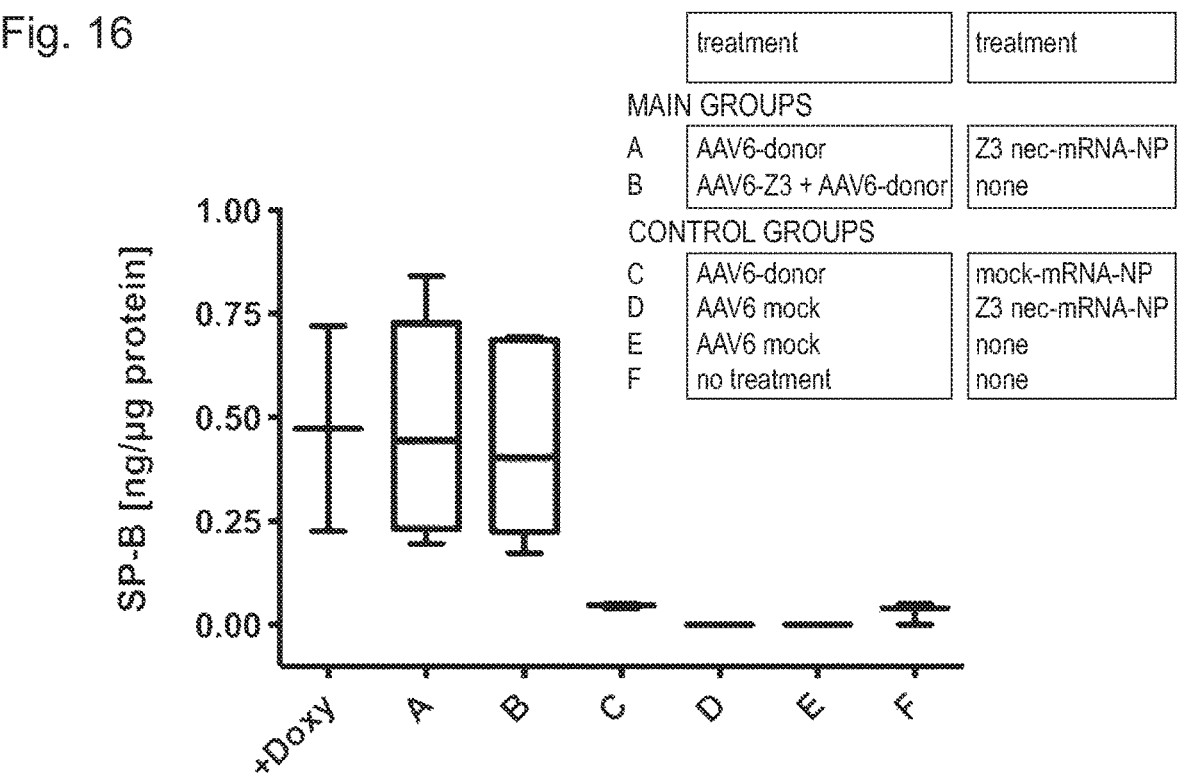
FIG. 16 SP-B expression in mouse experimental groups A-F as measured by Western blot. SP-B expression in ng/µg total protein was determined by Quantity One software (www.bio-rad.de). Boxes represent medians±IQRs (interquartile ranges). Whiskers represent the minimum and maximum observations. n=6 mice per group were used.
Figure 17:
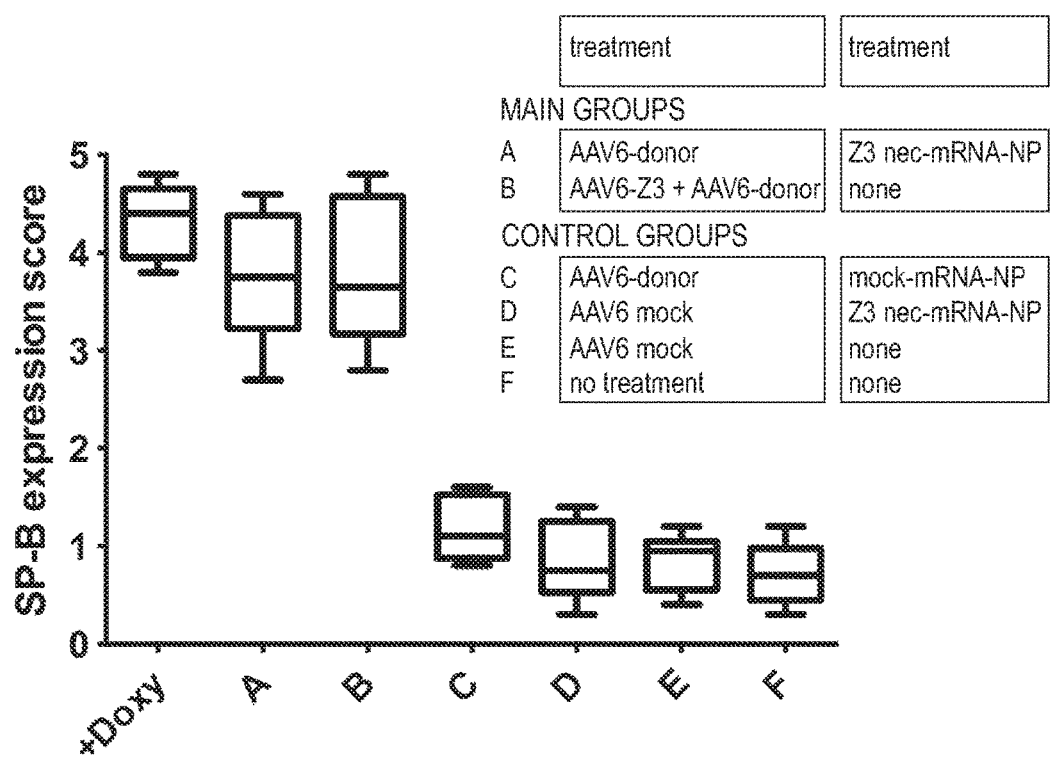
FIG. 17 Semiquantitative analysis of the immunohistochemistry shown in FIG. 2b). Boxes represent medians±IQRs (interquartile range). n=6 mice per group were used.

Moving in vivo, AAV6-donor and Z3 nec-mRNA-NP (or a Z3 AAV positive control) were then delivered to the lung of transgenic SP-B mice, followed by cessation of doxycycline (FIG. 13a). Notably, mice in these groups lived significantly longer in comparison to matched controls groups (FIG. 13a, P<0.001), while maintaining SP-B expression levels comparable to mice receiving doxycycline, as far as 20 d post-doxycycline-removal (FIG. 13b,c and FIGS. 16 and 17).

Figure 18:
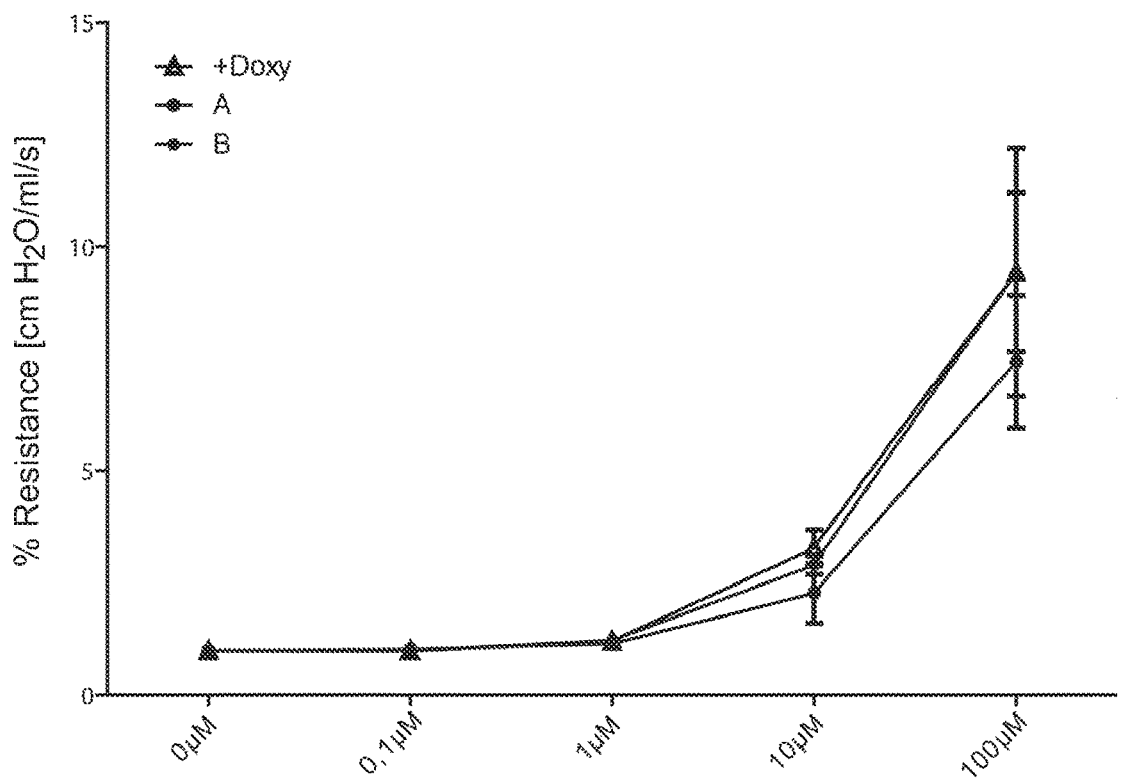
FIG. 18 % Resistance of mouse lungs after gene manipulation. Calculated by dividing the mean resistance values at the end of challenge by mean values at end of each washout period of the +Doxy group and main groups A and B, challenged with methacholine in rising concentrations over time to determine airway hyper responsiveness. n=3 mice per group were used.
Figure 21:
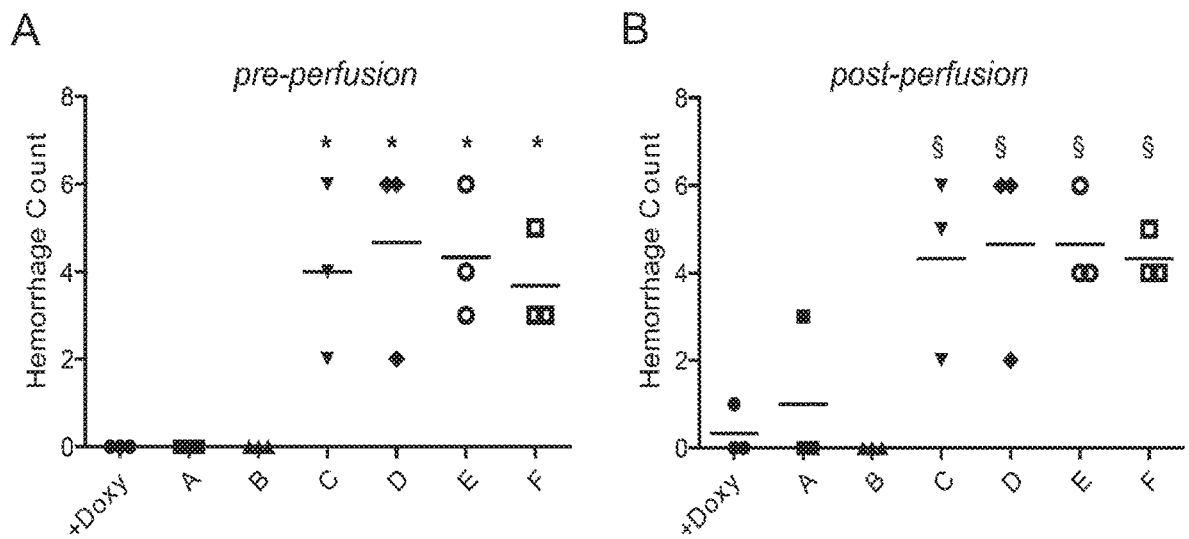
FIG. 21 Comparison of hemorrhagic counts (semiquantitive analysis of data from Supplementary FIGS. 14 and 15). If left lung showed partial hemorrhage it was counted as 1, when more than half of the left lung area was hemorrhagic it was counted as 2. For all four right lung lobes, signs of hemorrhage were counted as 1 (resulting in an maximum count of 6). The straight lines represent the means. a, hemorrhage count before perfusion; b, hemorrhage count after perfusion. *, $P<0.05$ versus Doxy-control, groups A and B; , $P<0.05$ versus Doxy-control and group B. (Mann-Whitney test, two-sided, asymptotic significance).
Figure 22:
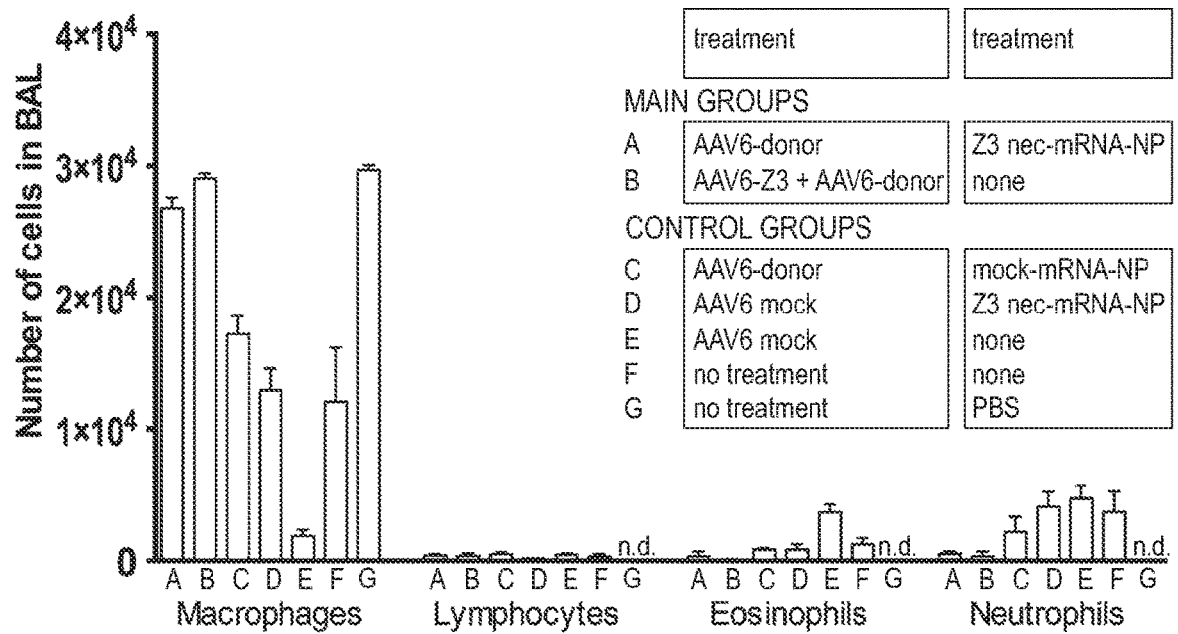
FIG. 22 Differential cell counts. Cells from lung lavages were stained with May-Grüwald/Giemsa, counted and related to 1 ml of BALF, 20 d after doxycycline removal.
Figure 23:
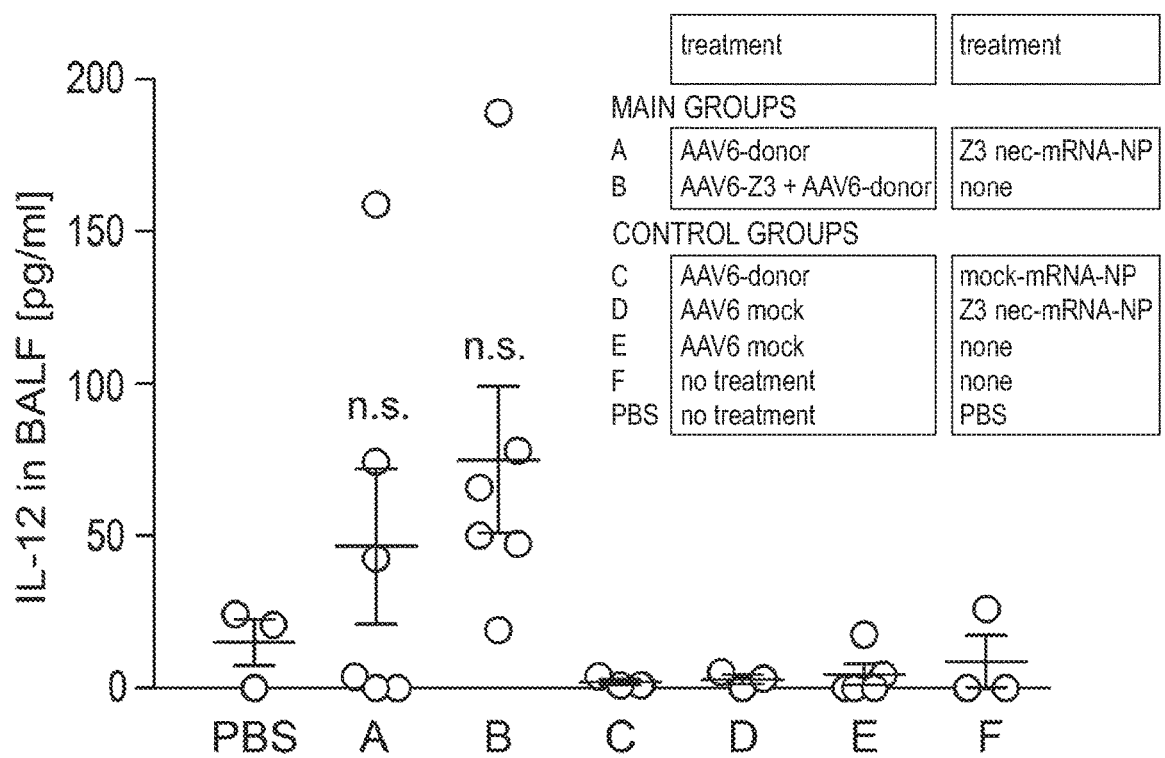
FIG. 23 IL-12 ELISA in BALF. Cytokine levels were quantified in mice BALF by ELISA at sacrificing date (mean±s.e.m); n.s., not significant. Serum was tested 20 days after doxycycline removal.
Figure 24:
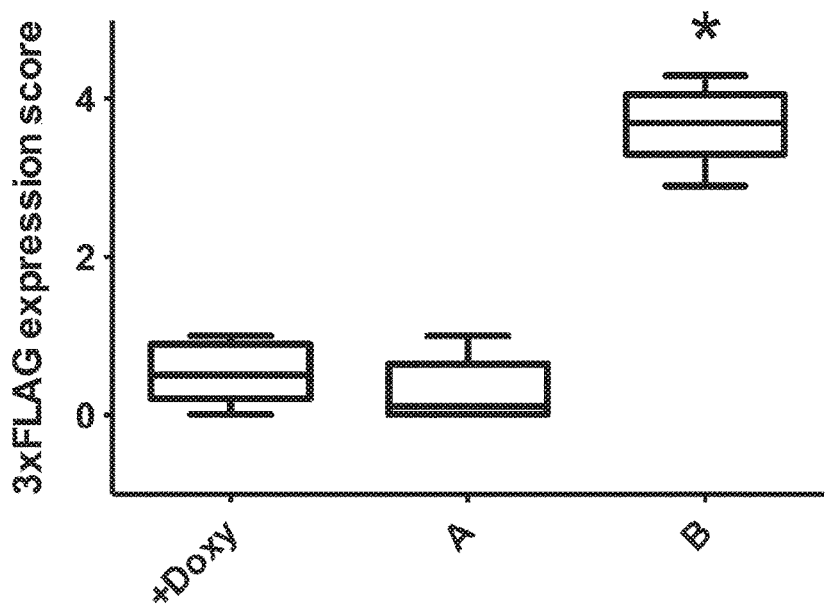
Figure 25:
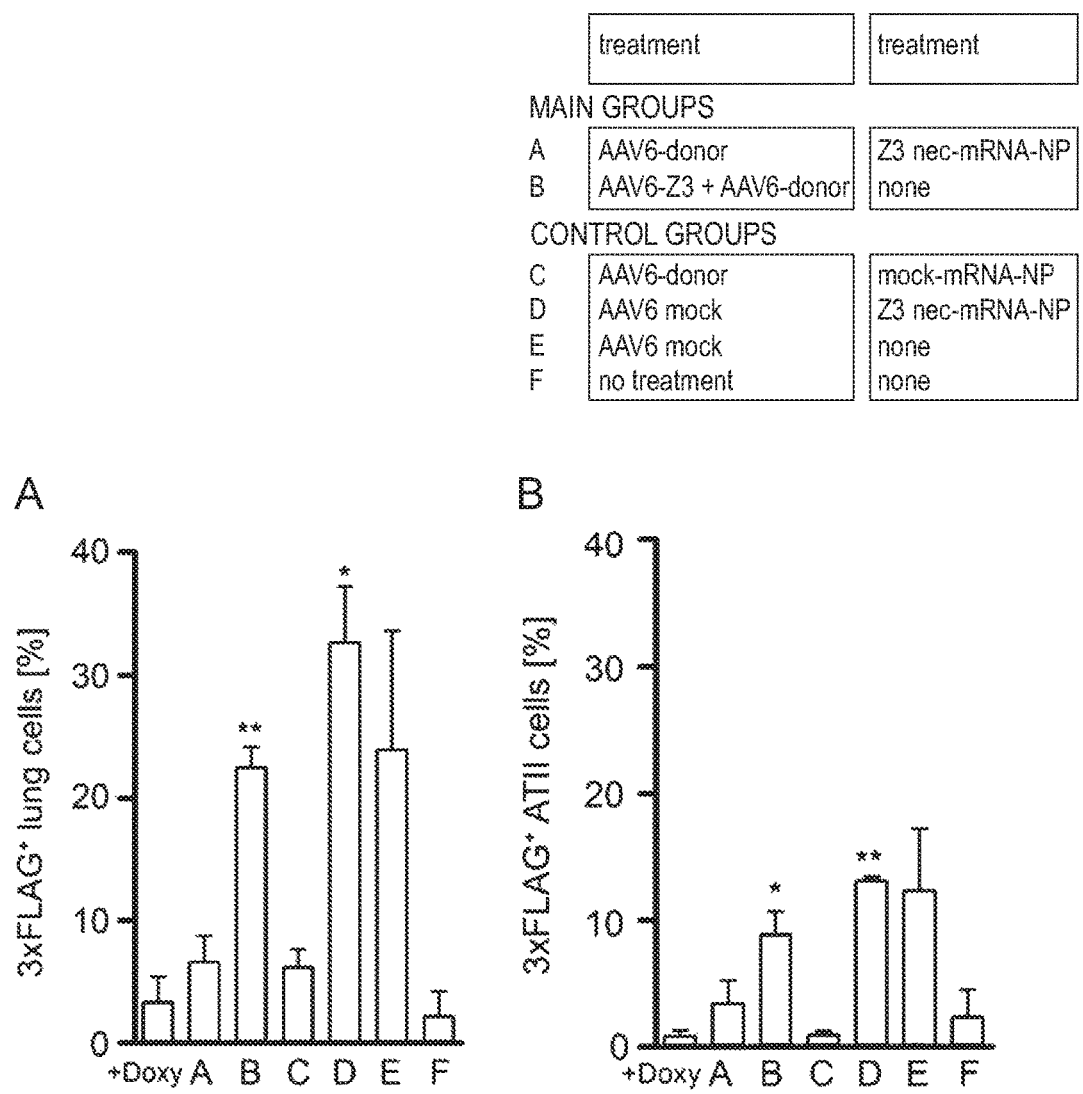
FIG. 25 Expression of 3xFLAG+in a) total lung cells and b) ATII cells. *, $P<0.05$ versus Doxy-control; **, $P<0.01$ versus Doxy-control. The tissue was harvested 20 d after doxycycline removal.
Figure 26:
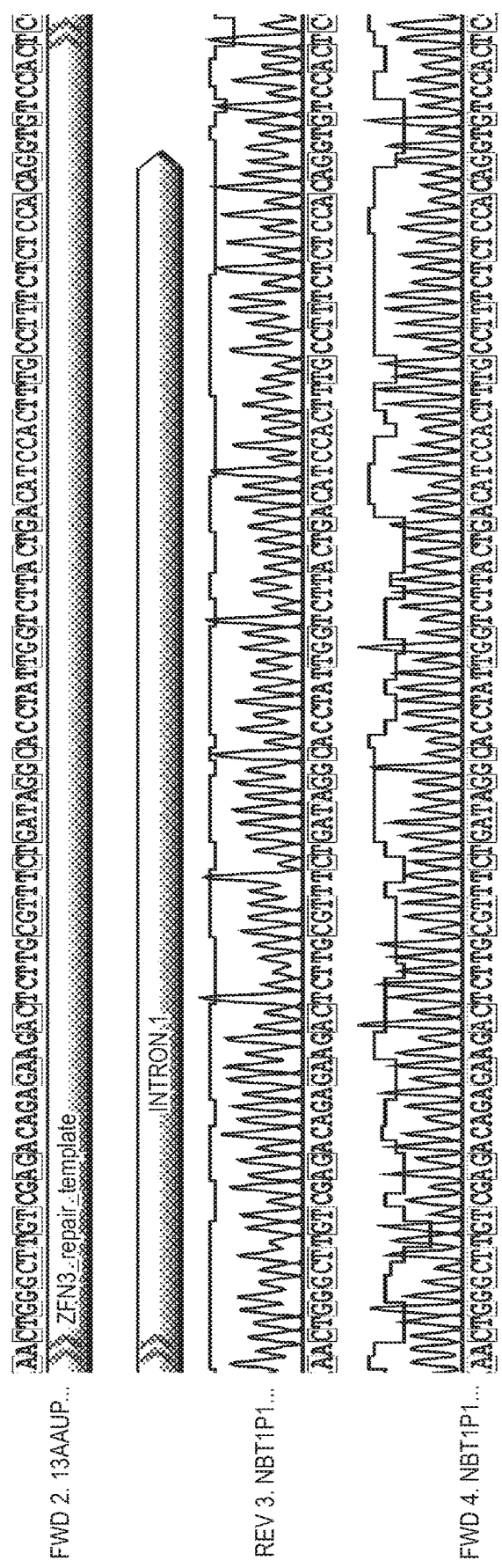
FIG. 26 Target site sequencing. We pooled sorted AT II cell samples within different experimental groups (A-F), one pool per group, performed single-cell separation, cloned PCR amplicons of the DNA (P1/P2) from those single cells in TOPO vectors, and sequenced the amplicons with primers P1 and P2. Subsequently, we performed an alignment of the sequences with the donor reference sequence, thereby identifying corrected cells (lower lanes depicting part of intron 1 (named "rev 3. NBT1P1 . . . " and "fwd 4. NBT1P1 . . . ").

Phenotypically, combining gene correction with AAV6-donor and Z3 nec-mRNA-NP (or Z3 AAV) prevented the significant drop in lung function (FIG. 13d and FIG. 18), severe hemorrhagic infiltrations and large-scale edema (FIGS. 19-21), and neutrophilia (FIG. 22) observed in the lungs of negative controls. A non-significant increase of IL-12 was observed in nec-mRNA-NP- versus PBS-treated mice (FIG. 13), however, no IFN-α elevation was detected (data not shown). DSBs and HDR rates (the latter determined by in-out PCR, see FIG. 13g) were concomitant with successful gene manipulation (FIG. 13e,f), which was also determined by target site sequencing (FIG. 26). If achieved in humans, HDR rates of ~9% would likely be sufficient to avoid severe disease progression (see Discussion). Results also confirmed that nuclease expression was longer-lived if administered via AAV, rendering nec-mRNA-NP a more favorable delivery vehicle (FIG. 13h and FIGS. 24 and 25).

Inherent key limitations of our approach are (i) the co-transfection of an AAV-DNA donor template in conjunction with nec-mRNA, (ii) the temporal delimitation of our curative in vivo treatment, probably owing to the natural turnover of the transfected lung cell populations, and (iii) the engineering of an artificial, transgenic cassette compared to humanized models. However, the use of nec-mRNA will have immediate implications for all nuclease platforms, including CRISPR/Cas9 systems, targeted gene knockout, as well as therapeutic gene correction strategies for the treatment of SP-B deficiency and other diseases, such as cancer. The inventors will test this technology in humanized models when available and are confident to move nec-mRNA and nec-mRNA-NP (for efficient lung transfection) finally to the clinic.

Overall, the inventors conclude that co-delivery of Z3 nec-mRNA-NP and AAV6-donor results in successful site-specific genome editing in vivo, documenting the first report of life-prolonging gene correction in the lung.

7. Discussion

This proof-of-principle in a transgenic model of SP-B deficiency demonstrates that nec-mRNA can achieve therapeutic levels of gene correction in vivo, while possessing the three main criteria of an optimal genome editing reagent: (i) transience, (ii) an inability to integrate, and (iii) sufficient transfection of target cells. As lung cell turnover likely prevented survival beyond 30-35 days in this model, animals in future studies will undergo repeated nec-mRNA administration to target additional differentiated cells of the lung.

The inventors made sure that the truncated SP-B gene fragment in the right homology arm does not express functional SP-B protein by testing the administration of AAV6 donor w/o functional nucleases (FIG. 13a, group C): all mice died within three days. Although there was still some residual SP-B detectable in the Western Blot (about 10%, which the inventors usually see if lavages are tested only three days after Doxycycline cessation (data not shown)), it is highly unlikely that this signal is derived from the donor construct as the molecular weight of the band is normal (and therefore inconsistent with any truncated form).

The ability to target and correct lung progenitor cells will also be the subject of ongoing investigation. The inventors also want to emphasize that the main safety gain by our nec-mRNA technology concerns the reduction of nuclease-derived off-target effects; it does not eliminate the integration of donor template. Since SP-B acts extracellularly in the alveolar space, modification of a small number of cells could functionally correct a larger area of lung tissue. The inventors found in vivo HDRs of about 9%: in humans 5-10% of SP-B levels in the lung are sufficient and show only a mild disease (in humans there are SNPs in the SP-B gene causing about 10% of normal SP-B levels, and many of those people were completely healthy. Also, there is no linear correlation between achieved HDR in lung cells (see FIG. 13f) and SP-B expression in the lungs (see FIGS. 13b,c and FIG. 17); together supporting the notion that an in vivo HDR of ~9%—if achievable—should have therapeutic effects in human.

Though AAV vectors have not been associated with genotoxicity, further development of nec-mRNA-mediated gene correction approaches may also benefit from pairing with a non-viral or integration-deficient lentiviral donor template. The inventors chose to not look for AAV donor integration for several reasons: a) the inventors wanted the vector to be as coherent as possible and AAV donor integration measurements are at best mere estimations; b) any experiment that uses a transgene donor will require the use of a DNA-based donor and therefore has some risk of insertional mutagenesis. Consequently, it is not possible to achieve HDR in vivo, while avoiding background vector integration. A multitude of papers describing use of AAV and lentivirus have been published in NBT, all of which have necessarily had some background level of donor integration; however no pathological effects of AAV utilization could be demonstrated in extensive murine studies; and c) the big advantage of the inventors' work is that mRNA delivery prevents the persistent expression of the nucleases. This is a far larger worry than background AAV integration.

Off-target cleavage in vitro on the top five in silico predicted sites was a minor issue with an average of only 0.78% indels at day 14 of transfected or transduced A549 cells (data not shown).

Figure 27:
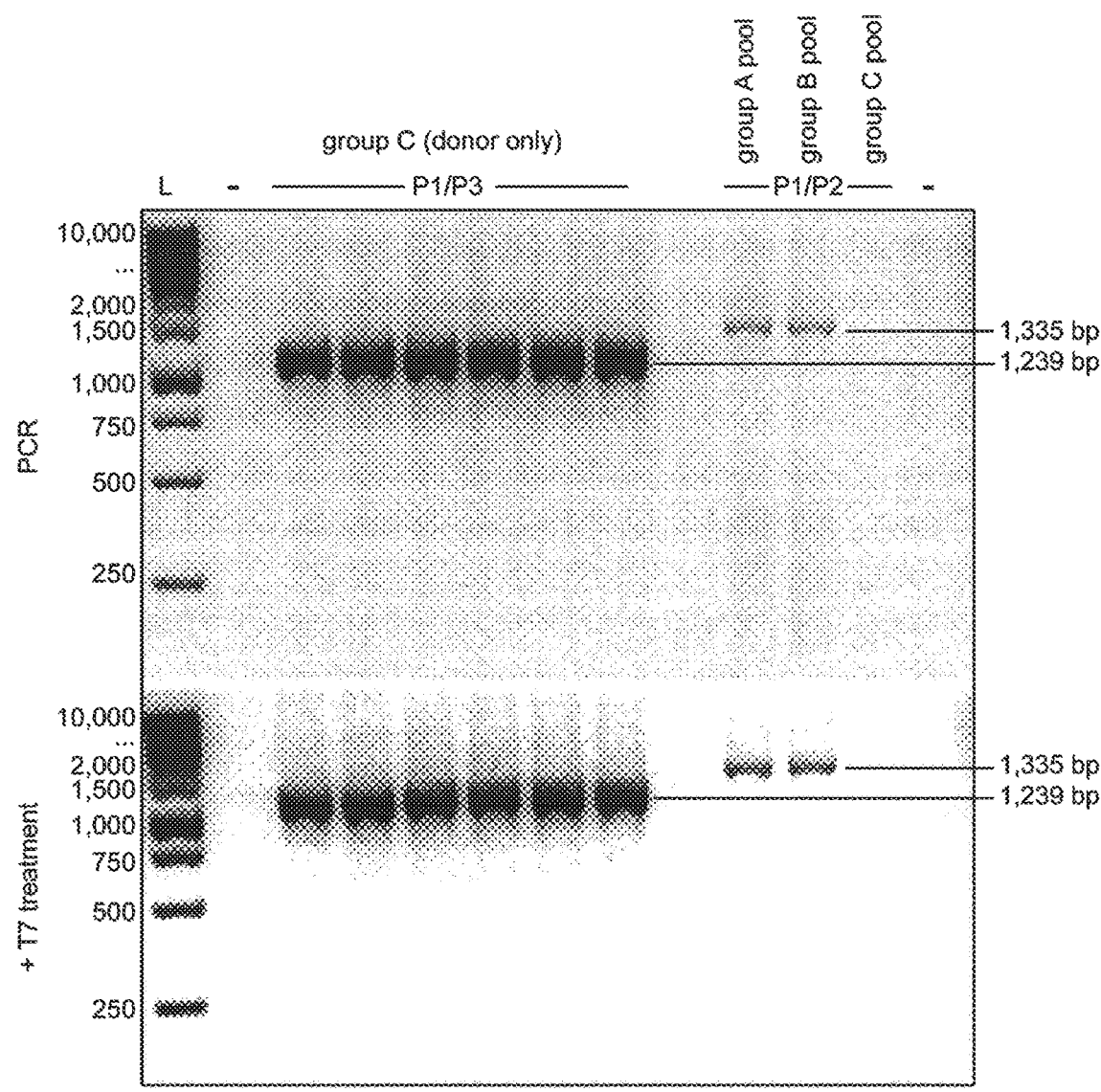
FIG. 27 In-out PCRs and T7 assays on DNA samples from donor only treated mice (group C). The non-appearance of any secondary band(s) demonstrates that no TI accidentally took place in the donor only group C. L, ladder. Lanes marked with "−" are the respective non-template negative controls.

We found it also important to perform in/out PCRs (and T7 endonuclease reactions) on lung samples of mice that received only AAV6-donor (group C). This is important because, given the large overlap between the donor and the chromosome in our case, recombination can occur in the PCR itself. Therefore, we did control PCRs (P1/P3, P1/P2) and T7 reactions on all mice (P1/P3, group C) or pooled samples (P1/P2, groups A, B and C) and could strengthen the positive results found in groups A and B, as no HDR event could have been detected in DNA samples from group C (FIG. 27).

With respect to human SP-B deficiency, it is important to note that the site-specific nucleases designed to target the transgenic locus in this mouse model will not be directly applicable to the human condition. Also, the CAG promoter is very strong, so manipulated cells likely produce significantly higher amounts of SP-B than normal, endogenous cells. Further, the PCR assay used for quantification likely underestimates the true amount of CAG promoter integration. Despite this, the inventors feel that transgenic SP-B deficient mice serve as an excellent proof-of-principle model for several reasons: first, cessation of doxycycline results in phenotypic changes closely modeling those observed in the human condition. Second, administration of doxycycline drives SP-B expression levels comparable to wild-type mice; and finally, the outcome of survival in this model is a definitive measure of efficacy. Together with Chitosan-coated NP's, nec-mRNA presents a strong tool to approach lung diseases still currently uncorrectable in the human system. Combining nec-mRNA with other structured NPs (cf. Young C. et al. Nat Prot 9, 1900-1915 (2014); incorporated herein by reference) may expand the capabilities of gene manipulation to other large disease fields such a cancer therapeutics.

8. Conclusion

The inventors were able to demonstrate in an impressive manner by means of a mouse model that by using a nuclease-encoding nucleotide-modified messenger RNA (nec-mRNA) a genetic alteration on a DNA can be permanently corrected. The nec-mRNA is administered together with a repair template which comprises the genetic information to be inserted or to be replaced, respectively.

What is claimed is:

1. A nuclease-encoding nucleotide-modified messenger RNA (nec-mRNA) configured for preconditioning the correction of a genetic alteration on a DNA that encodes a lung protein, wherein
   in the nec-mRNA approximately 25% of the uridine nucleotides and approximately 25% of the cytidine nucleotides are modified by exchanging uridine for 2-thiouridine (s2U) or pseudouridine (ψ), and by exchanging cytidine for 5-methylcytidine (m5C), and
   the nec-mRNA is packed into a nanoparticle, and
   the nec-mRNA has an expression level that is higher than the expression level of a comparable nec-mRNA wherein approximately 100% of the cytidine nucleotides are modified by exchanging cytidine for 5-methylcytidine (m5C), and
   the nec-mRNA is coupled to an aptamer that targets the nec-mRNA to a lung cell.

2. The nec-mRNA of claim 1, wherein the genetic alteration exists in a surfactant protein.

3. The nec-mRNA of claim 1, wherein the genetic alteration exists in a lung protein selected from the group consisting of surfactant protein B (SP-B), cystic fibrosis transmembrane and conductance regulator (CFTR), and Foxp3.

4. The nec-mRNA of claim 1, wherein the nuclease is configured in such a way that it can bind upstream or downstream of the genetic alteration on the DNA.

5. The nec-mRNA of claim 1, wherein the nuclease is selected from the group consisting of zinc-finger nucleases (ZFNs), transcription activator-like effector nucleases (TALEN), CRISPR/Cas9, and dimeric CRISPR RNA guided FokI nucleases.

6. The nec-mRNA of claim 1, wherein the nanoparticle is coated with chitosan.

7. The nec-mRNA of claim 1 associated with a repair template.

8. The nec-mRNA of claim 7, wherein the repair template comprises a nucleotide section which is exchangeable by homologous recombination (HR) against a section on the DNA comprising the genetic alteration.

9. The nec-mRNA of claim 8, wherein the repair template is one of the following: packed into an adeno-associated viral vector (AAV), encoded by a plasmid DNA, packed into a lentiviral vector, and packed into a protein-capped adenoviral vector (AdV).

10. The nec-mRNA of claim 1, wherein the genetic alteration exists in a lung protein that is Foxp3.

11. A pharmaceutical composition comprising the nuclease-encoding nucleotide-modified messenger RNA (nec-mRNA) of claim 1.

12. The pharmaceutical composition of claim 11, which further comprises a repair template.

13. The pharmaceutical composition of claim 12 that is configured for the treatment of a lung disease selected from the group consisting of surfactant protein B deficiency, cystic fibrosis (CF), asthma, and chronic obstructive pulmonary disease (COPD).

14. The pharmaceutical composition of claim 11, which comprises the nec-mRNA of claim 1, wherein the nec-mRNA encodes a nuclease which is configured in such a way that it can bind upstream or downstream of the genetic alteration on the DNA.

15. The pharmaceutical composition of claim 14, wherein the nanoparticle is coated with chitosan.

16. The pharmaceutical composition of claim 15, which further comprises a repair template.

17. The pharmaceutical composition of claim 11, which comprises the nec-mRNA of claim 1, wherein the nuclease is selected from the group consisting of zinc-finger nucleases (ZFNs), transcription activator-like effector nucleases (TALEN), CRISPR/Cas9, and dimeric CRISPR RNA guided FokI nucleases.

18. The pharmaceutical composition of claim 17, wherein the nanoparticle is coated with chitosan.

19. The pharmaceutical composition of claim 18, which further comprises a repair template.

20. The pharmaceutical composition of claim 11, wherein the nanoparticle is coated with chitosan.

21. The pharmaceutical composition of claim 20, which further comprises a repair template.

22. A method for the correction of a genetic alteration on a DNA that encodes a lung protein comprising the following steps:
   (1) introducing a repair template into a DNA-containing lung cell, which comprises the genetic alteration to be corrected, and
   (2) introducing the nec-mRNA of claim 1 into the lung cell.

23. The method of claim 22, wherein the introduction is realized by means of high pressure application of the repair template and the nec-mRNA into the lung.

24. The method of claim 23, wherein the nec-mRNA is the nec-mRNA of claim 7.

25. A method for the correction of a genetic alteration on a DNA that encodes a lung protein comprising the following steps:
   (1) introducing a repair template into a living being having a genetically altered DNA to be corrected, and
   (2) introducing the nec-mRNA of claim 1 into the living being.

26. The method of claim 25, wherein the introduction is realized by means of high pressure application of the repair template and the nec-mRNA into the lung of the living being.

27. The method of claim 26, wherein the nec-mRNA is the nec-mRNA of claim 7.

* * * * *